(12) United States Patent
Cao et al.

(10) Patent No.: US 12,357,834 B2
(45) Date of Patent: Jul. 15, 2025

(54) HIS-PURKINJE SYSTEM CAPTURE DETECTION

(71) Applicant: Medtronic, Inc., Minneapolis, MN (US)

(72) Inventors: Jian Cao, Shoreview, MN (US); Wade M. Demmer, Coon Rapids, MN (US); Elizabeth A. Mattson, Eagan, MN (US); Todd J. Sheldon, North Oaks, MN (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 680 days.

(21) Appl. No.: 17/533,005

(22) Filed: Nov. 22, 2021

(65) Prior Publication Data

US 2022/0080210 A1    Mar. 17, 2022

Related U.S. Application Data

(63) Continuation-in-part of application No. 16/901,110, filed on Jun. 15, 2020, now Pat. No. 11,607,550.

(60) Provisional application No. 62/866,037, filed on Jun. 25, 2019.

(51) Int. Cl.
*A61N 1/37* (2006.01)
*A61N 1/372* (2006.01)

(52) U.S. Cl.
CPC ....... *A61N 1/3706* (2013.01); *A61N 1/37247* (2013.01); *A61N 1/37282* (2013.01)

(58) Field of Classification Search
CPC ....... A61N 1/365; A61N 1/371; A61N 1/3712
See application file for complete search history.

(56) References Cited

U.S. PATENT DOCUMENTS

| 6,148,234 | A  | 11/2000 | Struble |
| 6,353,761 | B1 | 3/2002  | Conley et al. |
| 6,609,027 | B2 | 8/2003  | Kroll et al. |
| 6,768,924 | B2 | 7/2004  | Ding et al. |
| 7,184,815 | B2 | 2/2007  | Kim et al. |

(Continued)

FOREIGN PATENT DOCUMENTS

| EP | 3431135 A1    | 1/2019 |
| WO | 2019089510 A1 | 5/2019 |

OTHER PUBLICATIONS

PCT/US2020/039102) PCT Notification of Transmittal of the International Search Report and the Written Opinion of the International Searching Authority, Mailed Oct. 5, 2020, 9 pages.

(Continued)

*Primary Examiner* — Allen Porter

(57) ABSTRACT

A medical device is configured to receive a cardiac signal and determine a morphology matching score from the cardiac signal and a capture detection morphology template that corresponds to a first type of cardiac pacing capture that includes capture of at least a first portion of the His-Purkinje system. The device is configured to detect a second type of cardiac pacing capture in response to the morphology matching score being less than the first match threshold. The second type of cardiac pacing capture is different than the first type of cardiac pacing capture and may include capture of the ventricular myocardium and/or a second portion of the His-Purkinje system different than the first portion.

17 Claims, 23 Drawing Sheets

(56) References Cited

U.S. PATENT DOCUMENTS

| | | |
|---|---|---|
| 7,412,287 B2 | 8/2008 | Yonce et al. |
| 8,027,722 B1 * | 9/2011 | Nabutovsky .......... A61N 1/3622 607/9 |
| 8,527,050 B2 | 9/2013 | Stadler et al. |
| 8,565,865 B2 | 10/2013 | Belk et al. |
| 8,761,880 B2 | 6/2014 | Maskara et al. |
| 9,002,454 B2 | 4/2015 | Ghosh et al. |
| 9,168,382 B2 | 10/2015 | Shuros et al. |
| 9,227,073 B2 | 1/2016 | Bohn et al. |
| 9,789,319 B2 | 10/2017 | Sambelashvili |
| 10,881,862 B2 | 1/2021 | Ghosh |
| 11,007,369 B2 | 5/2021 | Sheldon et al. |
| 11,027,136 B2 | 6/2021 | Mangual-Soto et al. |
| 2002/0091330 A1 * | 7/2002 | MacAdam .......... A61B 5/7445 600/509 |
| 2011/0264158 A1 | 10/2011 | Dong et al. |
| 2012/0101542 A1 | 4/2012 | Arcot-Krishnamurthy et al. |
| 2019/0022378 A1 | 1/2019 | Prillinger et al. |
| 2019/0083800 A1 | 3/2019 | Yang et al. |
| 2019/0111270 A1 | 4/2019 | Zhou |
| 2019/0126049 A1 | 5/2019 | Casavant et al. |
| 2019/0134404 A1 | 5/2019 | Sheldon et al. |
| 2019/0134405 A1 | 5/2019 | Sheldon et al. |
| 2019/0192860 A1 | 6/2019 | Ghosh et al. |
| 2020/0353266 A1 | 11/2020 | Min et al. |
| 2020/0406041 A1 | 12/2020 | Cao et al. |
| 2021/0016097 A1 | 1/2021 | Mangual-Soto et al. |
| 2021/0308465 A1 | 10/2021 | Galarneau et al. |

OTHER PUBLICATIONS

Saini et al., Novel Method for Assessment of His Bundle Pacing Morphology Using Near Field and Far Field Device Electrograms, retrieved at: https://www.ahajournals.org/doi/10.1161/CIRCEP.118.006878, Feb. 1, 2019, 24 pages.

PCT/IB2022/060249) PCT Notification of Transmittal of the International Search Report and the Written Opinion of the International Searching Authority, Mailed Jan. 18, 2023, 9 pages.

Adachi et al, "QRS Complex Widening Due to Loss of Left Bundle Branch Capture: Pitfall of Para-Hisian Pacing", Journal of Interventional Cardiac Electrophysiology 2009, 4 pages.

Deshmukh et al., "Permanent, Direct HIS-Bundle Pacing: A Novel Approach to Cardiac Pacing in Patients with Normal HIS-Purkinje Activation", Circulation, American Heart Association, Inc., vol. 101, No. 8, Feb. 29, 2000, 9 pages.

Dandamudi et al., "How to Perform Permanent His Bundle Pacing in Routine Clinical Practice", 2016, Heart Rhythm Society, 5 pages.

Yuyun et al., "HIS Bundle Pacing: State of the Art", US Cardiology, vol. 12, No. 1, Jan. 2017, 10 pages.

* cited by examiner

HIS-PURKINJE SYSTEM CAPTURE DETECTION

REFERENCE TO RELATED APPLICATIONS

This application is a Continuation-in-Part of U.S. patent application Ser. No. 16/901,110, filed on Jun. 15, 2020 and entitled "His-Purkinje System Capture Detection," which claims the benefit of provisional U.S. Patent Application No. 62/866,037, filed on Jun. 25, 2019 and entitled "His Bundle Capture Detection," both of which are incorporated herein by reference in their entirety.

TECHNICAL FIELD

This disclosure relates to a medical device and method for determining the type of cardiac capture following delivery of a pacing pulse.

BACKGROUND

During normal sinus rhythm (NSR), the heartbeat is regulated by electrical signals produced by the sino-atrial (SA) node located in the right atrial wall. Each intrinsic atrial depolarization signal produced by the SA node spreads across the atria, causing the depolarization and contraction of the atria, and arrives at the atrioventricular (AV) node. The AV node responds by propagating a ventricular depolarization signal through the Purkinje of His (or "His bundle") of the ventricular septum and thereafter to the Purkinje branches and the Purkinje muscle fibers of the right and left ventricles. This native conduction system including the His bundle, right and left branches (sometimes referred to as the right and left bundle branches) and the Purkinje fibers may be referred to as the "His-Purkinje conduction system" or "His-Purkinje system."

Patients with a conduction system abnormality, e.g., poor AV node conduction, poor SA node function, or other conduction abnormalities, may receive a pacemaker to restore a more normal heart rhythm and AV synchrony. Ventricular pacing may be performed to maintain the ventricular rate in a patient having atrioventricular conduction abnormalities. A single chamber ventricular pacemaker may be coupled to a transvenous ventricular lead carrying electrodes placed in the right ventricle, e.g., in the right ventricular apex. The pacemaker itself is generally implanted in a subcutaneous pocket with the transvenous ventricular lead tunneled to the subcutaneous pocket. Intracardiac pacemakers have been introduced or proposed for implantation entirely within a patient's heart, eliminating the need for transvenous leads. An intracardiac pacemaker may provide sensing and pacing from within a chamber of the patient's heart, e.g., from within the right ventricle in a patient having AV conduction block or other conduction abnormalities to provide ventricular rate support.

Dual chamber pacemakers are available which include a transvenous atrial lead carrying electrodes which are placed in the right atrium and a transvenous ventricular lead carrying electrodes that are placed in the right ventricle via the right atrium. A dual chamber pacemaker senses atrial electrical signals and ventricular electrical signals and can provide both atrial pacing and ventricular pacing as needed to promote a normal atrial and ventricular rhythm and promote AV synchrony when SA and/or AV node or other conduction abnormalities are present.

Cardiac pacing of the His-Purkinje system has been proposed to provide ventricular pacing along the heart's native His-Purkinje conduction system. Chronic ventricular pacing via electrodes at or near the right ventricular apex may be associated with increased risk of atrial fibrillation or heart failure. Alternative pacing sites have been investigated or proposed, such as pacing the at or near the His bundle. Pacing the ventricles via the His-Purkinje system allows recruitment along the heart's natural conduction system and is hypothesized to promote more physiologically normal cardiac activation than other pacing sites, such as the ventricular apex.

SUMMARY

The techniques of this disclosure generally relate to determining cardiac capture, and in some instances the type of cardiac capture, achieved by cardiac pacing pulses delivered via pacing electrodes positioned to pace the His-Purkinje system. The pacing and sensing electrodes may be carried by a lead, e.g., a transvenous endocardial lead. In other examples, the pacing and sensing electrodes may be housing-based electrodes along the housing of a leadless pacemaker. Among the types of capture that may be achieved during His-Purkinje system pacing are selective His-Purkinje system capture during which only the His-Purkinje system is captured, non-selective His-Purkinje system capture during which both portions of the His-Purkinje system and the ventricular myocardium are captured, ventricular myocardial capture only without capture of the His-Purkinje system, and loss of ventricular capture. The type of capture may depend on the location of the electrodes relative to the His-Purkinje system, the pacing pulse energy and other factors. A medical device operating according to the techniques disclosed herein may determine the type of capture following a pacing pulse and determine various capture thresholds for different types of capture such as selective His-Purkinje system capture and ventricular myocardial capture. The medical device may respond to determination of the capture type or determination of loss of capture by adjusting a pacing pulse control parameter such as pacing pulse amplitude or performing a capture threshold search. The medical device may be configured to monitor for capture during cardiac pacing delivered to the His-Purkinje system to detect a change in capture type or loss of capture and provide an appropriate response.

In one example, the disclosure provides a medical device including a memory configured to store a capture detection morphology template corresponding to a first type of cardiac pacing capture that includes capture of a first portion of the His-Purkinje system. The medical device includes a processing circuit configured to receive a cardiac electrical signal and determine a morphology matching score from the cardiac electrical signal and the capture detection morphology template. The processing circuit is configured to determine when the morphology matching score is less than a match threshold and detect a second type of cardiac pacing capture in response to the morphology matching score being less than the match threshold. The second type of cardiac pacing capture is different than the first type of cardiac pacing capture.

In another example, the disclosure provides a method performed by a medical device including storing a capture detection morphology template corresponding to a first type of cardiac pacing capture that includes capture of a first portion of the His-Purkinje system. The method further includes receiving a cardiac electrical signal, determining a morphology matching score from the cardiac electrical signal and the capture detection morphology template, determining that the morphology matching score is less than a match threshold, and detecting a second type of cardiac pacing capture in response to the morphology matching score being less than the match threshold. The second type of cardiac pacing capture is different than the first type of cardiac pacing capture.

In yet another example, the disclosure provides a non-transitory, computer-readable storage medium comprising a set of instructions which, when executed by a control circuit of a medical device, cause the medical device to store a capture detection morphology template corresponding to a first type of cardiac pacing capture that includes capture of a first portion of the His-Purkinje system. The instructions may further cause the device to receive a cardiac electrical signal, determine a morphology matching score from the cardiac electrical signal and the capture detection morphology template, determine when the morphology matching score is less than a match threshold, and detect a second type of cardiac pacing capture in response to the morphology matching score being less than the match threshold. The second type of cardiac pacing capture is different than the first type of cardiac pacing capture.

Further disclosed herein is the subject matter of the following clauses:

1. A medical device, comprising: a memory configured to store at least a first capture detection morphology template corresponding to a first type of cardiac pacing capture that includes capture of a first portion of a His-Purkinje system; and a processing circuit configured to: receive a cardiac electrical signal; determine a first morphology matching score from the cardiac electrical signal and the first capture detection morphology template; determine that the first morphology matching score is less than a first match threshold; and detect a second type of cardiac pacing capture in response to the first morphology matching score being less than the first match threshold, the second type of cardiac pacing capture being different than the first type of cardiac pacing capture.

2. The medical device of clause 1, wherein the processing circuit is further configured to determine a differential signal from the cardiac electrical signal and determine the first morphology matching score from the cardiac electrical signal and the first capture detection morphology template by determining a morphology matching score from the differential signal and the first capture detection morphology template.

3. The medical device of clause 2, wherein the processing circuit is further configured to determine a low pass filtered signal from the cardiac electrical signal and determine the differential signal from the low pass filtered signal.

4. The medical device of any of clauses 2-3, wherein the processing circuit is further configured to determine the differential signal by determining each sample point of the differential signal using at least three points of the cardiac electrical signal.

5. The medical device of any of clauses 1-4, wherein the processing circuit is further configured to establish the first capture detection morphology template from the cardiac electrical signal sensed following pacing pulse delivery to at least a portion of the His-Purkinje system at a first pacing pulse output.

6. The medical device of clause 5, wherein the processing circuit is further configured to receive the cardiac electrical signal sensed following pacing pulse delivery to at least the portion of the His-Purkinje system at a second pacing pulse output and establish a second capture detection morphology template from the cardiac electrical signal sensed following pacing pulse delivery at the second pacing pulse output, the second capture detection morphology template corresponding to the second type of cardiac pacing capture.

7. The medical device of clause 6, wherein the processing circuit is further configured to determine a second morphology matching score from the cardiac electrical signal and the second capture detection morphology template, determine that the second morphology matching score is less than a second match threshold, and detect a third type of cardiac pacing capture different than the first type of cardiac pacing capture and the second type of cardiac pacing capture in response to the second morphology matching score being less than the second match threshold.

8. The medical device of any of clauses 1-7, wherein the processing circuit is further configured to determine the first morphology matching score from the first capture detection morphology template and the cardiac electrical signal sensed following pacing pulse delivery at a first pacing pulse output, determine a second morphology matching score from the first capture detection morphology template and the cardiac electrical signal sensed following pacing pulse delivery at a second pacing pulse output different than the first pacing pulse output, determine that the second morphology matching score is less than a second match threshold different than the first match threshold, and detect a third type of cardiac pacing capture different than the first type of cardiac pacing capture in response to the second morphology matching score being less than the first match threshold.

9. The medical device of any of clauses 1-8, wherein the processing circuit is further configured to select a pacing pulse output in response to detecting the second type of cardiac pacing capture.

10. The medical device of any of clauses 1-9, wherein the processing circuit is further configured to perform a capture threshold test in response to detecting the second type of cardiac pacing capture.

11. The medical device of any of clauses 1-10, further comprising a sensing circuit configured to sense the cardiac electrical signal and a therapy delivery circuit configured to generate pacing pulses according to a pacing pulse output, wherein the processing circuit is configured to adjust the pacing pulse output in response to detecting the second type of cardiac pacing capture.

12. The medical device of any of clauses 1-11, further comprising a display unit, wherein the processing circuit is further configured to determine a differential signal from the cardiac electrical signal and determine the first morphology matching score from the differential signal, wherein the display unit is configured to generate a display of a user interface comprising a display of the differential signal.

13. The medical device of any of clauses 1-12, further comprising a display unit, wherein the processing circuit is further configured to determine a plurality of morphology matching scores from the cardiac electrical signal following each of a plurality of pacing pulses, and wherein the display unit is configured to generate a display of a user interface including a display of the plurality of morphology matching scores determined by the processing circuit.

14. The medical device of any of clauses 1-13, wherein the processing circuit is further configured to detect the second type of cardiac pacing capture by detecting cardiac pacing capture that includes capture of a second portion of the His-Purkinje system different than the first portion of the His-Purkinje system.
15. The medical device of any of clauses 1-14, wherein the processing circuit is further configured to detect the second type of cardiac pacing capture by detecting cardiac pacing capture that includes ventricular myocardial capture.
16. The medical device of any of clauses 1-15, wherein the processing circuit is further configured to determine a first plurality of morphology matching scores from the cardiac signal; and establish the first match threshold based on at least the first plurality of morphology matching scores.
17. The medical device of any of clauses 1-16, wherein the processing circuit is further configured to establish the first match threshold by determining the first plurality of morphology matching scores from the cardiac signal associated with pacing pulse delivery at each of a plurality of different pacing pulse outputs, identifying a first group of matching scores from the plurality of morphology matching scores, identifying a second group of matching scores from the plurality of morphology matching scores, the second group of matching scores being different than the first group of matching scores; and establishing the first match threshold to be between the first group of matching scores and the second group of matching scores.
18. The medical device of any of clauses 1-17, wherein the processing circuit is further configured to establish the first match threshold by determining a first plurality of morphology matching scores from the cardiac signal associated with pacing pulse delivery at each of a plurality of different pacing pulse outputs, determining a frequency distribution of the first plurality of morphology matching scores; and establishing the first match threshold based on the frequency distribution of the first plurality of morphology matching scores.
19. The medical device of any of clauses 2-11, further comprising a telemetry circuit configured to transmit at least one of the differential signal and the first morphology matching score.
20. The medical device of any of clauses 1-19, wherein the processing circuit is further configured to determine a differential signal from the cardiac electrical signal by determining each sample point of the differential signal using at least five sample points of the cardiac electrical signal and determine the first morphology matching from the cardiac electrical signal and the first capture detection morphology template by determining a morphology matching score from the differential signal and the first capture detection morphology template.
21. A method comprising storing a first capture detection morphology template corresponding to a first type of cardiac pacing capture that includes capture of a first portion of a His-Purkinje system; receiving a cardiac electrical signal; determining a first morphology matching score from the cardiac electrical signal and the first capture detection morphology template; determining that the first morphology matching score is less than a first match threshold; and detecting a second type of cardiac pacing capture in response to the first morphology matching score being less than the first match threshold, the second type of cardiac pacing capture being different than the first type of cardiac pacing capture.
22. The method of clause 21, further comprising determining a differential signal from the cardiac electrical signal and determining the first morphology matching score from the cardiac electrical signal and the first capture detection morphology template by determining a morphology matching score from the differential signal and the first capture detection morphology template.
23. The method of clause 22, further comprising: determining a low pass filtered signal from the cardiac electrical signal; and determining the differential signal from the low pass filtered signal.
24. The method of any of clauses 21-23, wherein determining the differential signal comprises determining each sample point of the differential signal using at least three points of the cardiac electrical signal.
25. The method of any of clauses 21-24, further comprising establishing the first capture detection morphology template from the cardiac electrical signal sensed following pacing pulse delivery to at least a portion of the His-Purkinje system at a first pacing pulse output.
26. The method of clause 25, further comprising receiving the cardiac electrical signal sensed following pacing pulse delivery to at least the portion of the His-Purkinje system at a second pacing pulse output and establishing a second capture detection morphology template from the cardiac electrical signal sensed following pacing pulse delivery at the second pacing pulse output, the second capture detection morphology template corresponding to the second type of cardiac pacing capture.
27. The method of clause 26, further comprising determining a second morphology matching score from the cardiac electrical signal and the second capture detection morphology template, determining that the second morphology matching score is less than a second match threshold, and detecting a third type of cardiac pacing capture different than the first type of cardiac pacing capture and the second type of cardiac pacing capture in response to the second morphology matching score being less than the second match threshold.
28. The method of any of clauses 21-27, further comprising determining the first morphology matching score from the first capture detection morphology template and the cardiac electrical signal sensed following pacing pulse delivery at a first pacing pulse output, determining a second morphology matching score from the first capture detection morphology template and the cardiac electrical signal sensed following pacing pulse delivery at a second pacing pulse output different than the first pacing pulse output, determining that the second morphology matching score is less than a second match threshold different than the first match threshold, and detecting a third type of cardiac pacing capture different than the first type of cardiac pacing capture in response to the second morphology matching score being less than the first match threshold.
29. The method of any of clauses 21-28 further comprising selecting a pacing pulse output in response to detecting the second type of cardiac pacing capture.
30. The method of any of clauses 21-29 further comprising performing a capture threshold test in response to detecting the second type of cardiac pacing capture.
31. The method of any of clauses 21-30 further comprising sensing the cardiac electrical signal, generating pacing pulses according to a pacing pulse output; and adjusting the pacing pulse output in response to detecting the second type of cardiac pacing capture.

32. The method of any of clauses 21-31 further comprising determining a differential signal from the cardiac electrical signal, determining the first morphology matching score from the differential signal, and generating a display of a user interface comprising a display of the differential signal.

33. The method of any of clauses 21-32 further comprising determining a plurality of morphology matching scores from the cardiac electrical signal sensed following each of a plurality of pacing pulses and generating a display of a user interface including a display of the plurality of morphology matching scores.

34. The method of any of clauses 21-33 wherein detecting the second type of cardiac pacing capture comprises detecting capture of a second portion of the His-Purkinje system different than the first portion of the His-Purkinje system.

35. The method of any of clauses 21-34 wherein detecting the second type of cardiac pacing capture comprises detecting cardiac pacing capture that includes ventricular myocardial capture.

36. The method of any of clauses 21-35, further comprising determining a first plurality of morphology matching scores from the cardiac signal and establishing the first match threshold based on at least the first plurality of morphology matching scores.

37. The method of any of clauses 21-36, wherein the processing circuit is further configured to establish the first match threshold by determining a first plurality of morphology matching scores from the cardiac signal associated with pacing pulse delivery at each of a plurality of different pacing pulse outputs, identifying a first group of matching scores from the plurality of morphology matching scores, identifying a second group of matching scores from the plurality of morphology matching scores, the second group of matching scores being different than the first group of matching scores, and establishing the first match threshold to be between the first group of matching scores and the second group of matching scores.

35. The method of any of clauses 21-37 further comprising establishing the first match threshold by determining a plurality of morphology matching scores from the cardiac signal associated with pacing pulse delivery at each of a plurality of different pacing pulse outputs, determining a frequency distribution of the plurality of morphology matching scores; and establishing the first match threshold based on the frequency distribution of the first plurality of morphology matching scores.

36. The method of any of clauses 22-35, further comprising transmitting at least one of the differential signal and the first morphology matching score.

37. The method of any of clauses 21-36, wherein the processing circuit is further configured to determine a differential signal from the cardiac electrical signal by determining each sample point of the differential signal using at least five sample points of the cardiac electrical signal and determine the first morphology matching from the cardiac electrical signal and the first capture detection morphology template by determining a morphology matching score from the differential signal and the first capture detection morphology template.

38. A non-transitory, computer-readable storage medium comprising a set of instructions which, when executed by a processing circuit of a medical device cause the medical device to store a capture detection morphology template corresponding to a first type of cardiac pacing capture that includes capture of a first portion of a His-Purkinje system, receive a cardiac electrical signal, determine a morphology matching score from the cardiac electrical signal and the capture detection morphology template, determine that the morphology matching score is less than a match threshold and detect a second type of cardiac pacing capture in response to the morphology matching score being less than the match threshold, the second type of cardiac pacing capture being different than the first type of cardiac pacing capture.

39. The non-transitory, computer-readable storage medium of clause 38, further comprising instructions that cause the medical device to determine a differential signal from the cardiac electrical signal and determine the morphology matching score from the cardiac electrical signal and the capture detection morphology template by determining a morphology matching score from the differential signal and the first capture detection morphology template.

40. The non-transitory, computer-readable storage medium of any of clauses 38-39, further comprising instructions that cause the medical device to perform a capture threshold test in response to detecting the second type of cardiac pacing capture.

41. A medical device comprising: a memory configured to store a capture detection morphology template corresponding to a first type of cardiac pacing capture that includes capture of a first portion of a His-Purkinje system; a processing circuit configured to receive a cardiac electrical signal, determine a differential signal from the cardiac electrical signal, and determine a morphology matching score from the differential signal and the capture detection morphology template; and a display unit configured to receive the morphology matching score from the processing circuit and generate a display of a graphical user interface including at least the morphology matching score.

42. The medical device of clause 41 wherein the processing circuit is further configured to determine that the morphology matching score is less than a match threshold and detect a second type of cardiac pacing capture in response to the morphology matching score being less than the match threshold, the second type of cardiac pacing capture being different than the first type of cardiac pacing capture.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
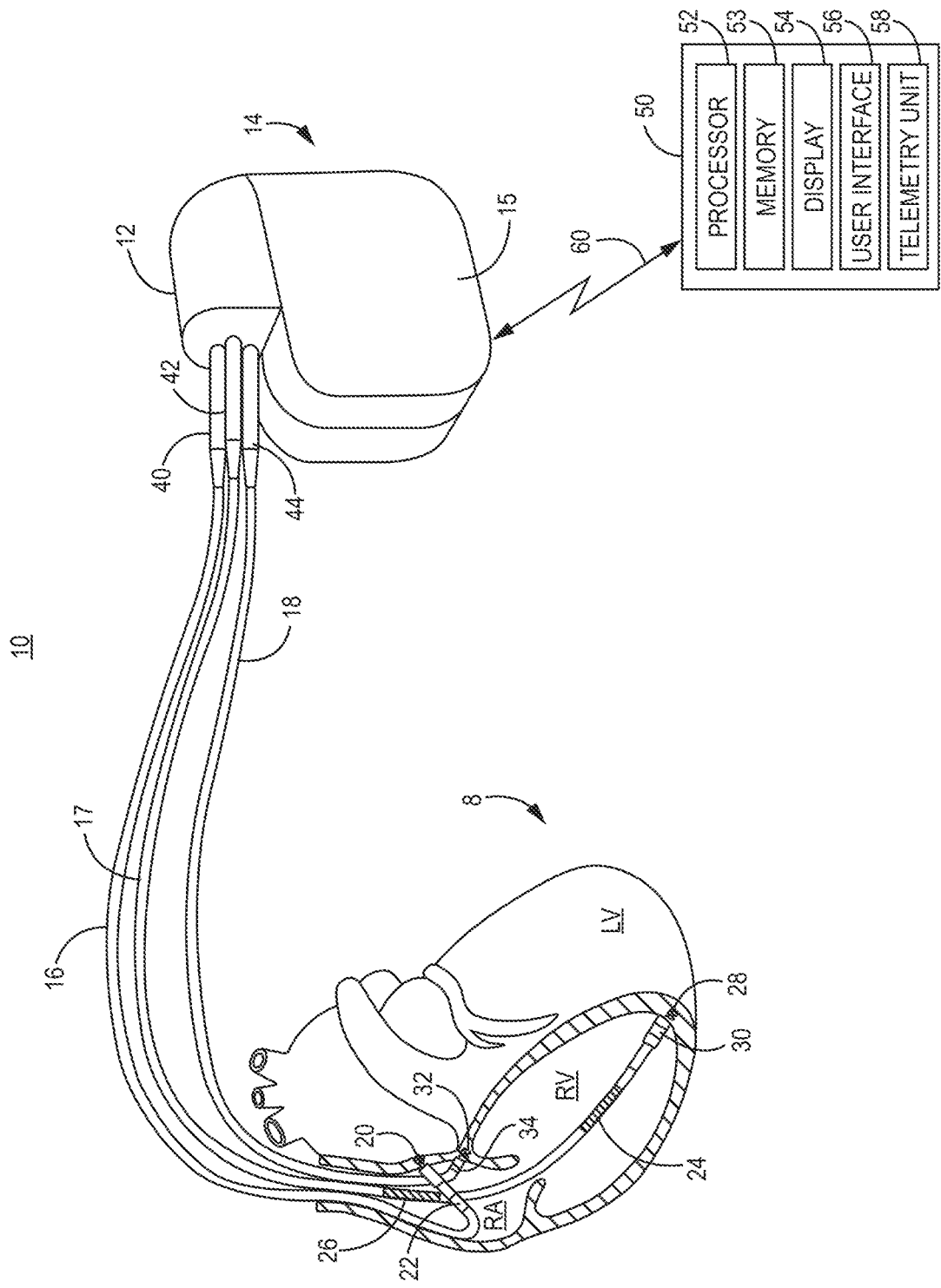
FIG. 1A is a conceptual diagram of a medical device system capable of delivering His-Purkinje system pacing and sensing cardiac electrical signals.

Examples of a medical device capable of generating pacing pulses for delivery to the His-Purkinje conduction system of a patient's heart are described herein. The medical device is configured to detect the type of cardiac capture that occurs following a generated pacing pulse according to the presently disclosed techniques. A cardiac tissue is "captured" by a pacing pulse having sufficient electrical energy to cause depolarization of the cardiac tissue at the pacing site, causing an electrical "evoked response," and subsequent mechanical contraction of the heart chamber. In order to effectively capture and pace the heart to achieve a desired therapeutic effect, cardiac pacing pulses need to have a pulse energy that is equal to or greater than the capture threshold of the cardiac tissue at the pacing site. A pacing capture threshold test may be performed to determine the minimum pacing pulse amplitude for a given pacing pulse width (or vice versa) that captures the heart chamber. Determination of the capture threshold enables proper programming of the pacing pulse amplitude and pulse width to promote effective pacing and avoid loss of capture. Capture monitoring by the pacemaker during ongoing pacing pulse delivery according to a pacing therapy allows automatic adjustments to the pacing pulse amplitude and/or pulse width to a suprathreshold value when loss of capture or a change in capture type is detected.

As used herein, the term "His-Purkinje" e.g., used to refer to "His-Purkinje pacing," "His-Purkinje pacing pulses," "His-Purkinje capture," etc., may refer collectively to the His-Purkinje conduction system, which includes the His bundle, right and left-Purkinje branches and the Purkinje fibers, such that "His-Purkinje pacing" may refer generally to pacing anywhere along the His-Purkinje conduction system, "His-Purkinje pacing pulses" may be delivered anywhere along the His-Purkinje conduction system, and "His-Purkinje capture" may refer to capture of the His-Purkinje conduction system, which may be capture at or inferior to the His bundle, e.g., along a left and/or right bundle branch, and is also referred to herein as "His-Purkinje system capture." When pacing pulses are delivered by electrodes positioned in the heart to pace the His-Purkinje conduction system it is possible to capture only the His-Purkinje system, capture both the His-Purkinje system and surrounding ventricular myocardium, or capture the surrounding ventricular myocardium without capturing the His-Purkinje system. Capture of only the His-Purkinje system is referred to herein as "selective" His-Purkinje system (SHP) capture. Capture of the His-Purkinje system and surrounding ventricular myocardial tissue is referred to herein as "non-selective" His-Purkinje system (NSHP) capture. Capture of the surrounding ventricular myocardium without capturing the His-Purkinje system is referred to as ventricular myocardial (VM) capture. When the pacing pulse energy is below both the His-Purkinje system capture threshold and the VM capture threshold, a loss of capture occurs. Determination of which type of capture is occurring in response to a His-Purkinje pacing pulse intended to capture the anywhere along the His-Purkinje system and determination of the His-Purkinje capture threshold allows for providing selective or non-selective capture of the His-Purkinje system, as desired, in order to achieve ventricular pacing along the native His-Purkinje system.

FIG. 1A is a conceptual diagram of a medical device system 10 capable of pacing and sensing in a patient's heart 8. The system 10 includes implantable medical device (IMD) 14 coupled to a patient's heart 8 via transvenous electrical leads 16, 17 and 18. IMD 14 is shown as a dual chamber device capable of delivering cardiac pacing pulses and sensing cardiac electrical signals in the right atrium (RA) and in the right ventricle (RV). Housing 15 encloses internal circuitry corresponding to the various circuits and components described in conjunction with FIG. 3 below, for sensing cardiac signals from heart 8, detecting arrhythmias, controlling therapy delivery and monitoring for capture type using the techniques disclosed herein.

IMD 14 includes a connector block 12 that may be configured to receive the proximal ends of a RA lead 16, an optional RV lead 17 and a His pacing and sensing lead 18, which are advanced transvenously for positioning electrodes for sensing and stimulation in the atria and ventricles. RA lead 16 is positioned such that its distal end is in the vicinity of the right atrium and the superior vena cava. RA lead 16 is equipped with pacing and sensing electrodes 20 and 22, shown as a tip electrode 20 and a ring electrode 22 spaced proximally from tip electrode 20. The electrodes 20 and 22 provide sensing and pacing in the right atrium and are each connected to a respective insulated conductor extending within the elongated body of RA lead 16. Each insulated conductor is coupled at its proximal end to a connector carried by proximal lead connector 40.

His pacing and sensing lead 18 may be advanced within the right atrium to position electrodes 32 and 34 for pacing and sensing in the vicinity of the His-Purkinje system, e.g., at or near the His bundle, from a right atrial approach, as shown. His lead tip electrode 32 may be a helical electrode that is advanced into the inferior end of the interatrial septum, beneath the AV node and near the tricuspid valve annulus to position tip electrode 32 in or proximate to the His bundle. A ring electrode 34 spaced proximally from tip electrode 32 may be used as the return electrode with the cathode tip electrode 32 for pacing the right and left ventricles via the native His-Purkinje system.

An intracardiac electrogram (EGM) signal may be produced by cardiac electrical signal sensing circuitry included in IMD 14 from the cardiac electrical signal obtained using the tip electrode 32 and ring electrode 34 of His pacing and sensing lead 18 and received by the sensing circuitry. As described below, the EGM signal produced from the cardiac electrical signal received via His pacing and sensing lead 18 is referred to herein as a "near field His-Purkinje signal" and may be used for detecting capture of the His-Purkinje system and discriminating between SHP capture, NSHP capture, VM capture and loss of capture. The electrodes 32 and 34 are coupled to respective insulated conductors extending within the elongated body of His pacing and sensing lead 18, which provide electrical connection to the proximal lead connector 44 coupled to connector block 12.

In some examples, IMD 14 may optionally be coupled to RV lead 17 for positioning electrodes within the RV for sensing RV cardiac signals and delivering pacing or shocking pulses in the RV. For these purposes, RV lead 17 is equipped with pacing and sensing electrodes shown as a tip electrode 28 and a ring electrode 30. RV lead 17 is further shown to carry defibrillation electrodes 24 and 26, which may be elongated coil electrodes used to deliver high voltage cardioversion/defibrillation (CV/DF) pulses. Defibrillation electrode 24 may be referred to as the "RV defibrillation electrode" or "RV coil electrode" because it may be carried along RV lead 17 such that it is positioned substantially within the right ventricle when distal pacing and sensing electrodes 28 and 30 are positioned for pacing and sensing in the right ventricle. Defibrillation electrode 26 may be referred to as a "superior vena cava (SVC) defibrillation electrode" or "SVC coil electrode" because it may be carried along RV lead 17 such that it is positioned at least partially along the SVC when the distal end of RV lead 17 is advanced within the right ventricle.

Each of electrodes 24, 26, 28 and 30 are connected to a respective insulated conductor extending within the body of RV lead 17. The proximal ends of the insulated conductors are coupled to corresponding connectors carried by proximal lead connector 42, e.g., a DF-4 connector, for providing electrical connection to IMD 14. In other examples, RV lead 17 may carry RV coil electrode 24 and SVC coil electrode 26 to provide high voltage therapies without carrying any pacing and sensing electrodes 28 and 30. Housing 15 may function as an active electrode during CV/DF shock delivery in conjunction with RV coil electrode 24 or SVC coil electrode 26. In some examples, RV lead 17 is omitted from IMD system 10.

Housing 15 may function as a return electrode for unipolar sensing or pacing configurations with any of the electrodes carried by leads 16 and 18 (and RV lead 17 if present). As described herein, an electrode carried by His pacing and sensing lead 18, e.g., tip electrode 32, may be used in combination with housing 15 for receiving a far field cardiac electrical signal used in detecting capture following delivery of a His-Purkinje pacing pulse. Electrodes 32 and 34 are used in a bipolar sensing pair for receiving a near field His-Purkinje signal. IMD 14 is configured to produce a far field EGM signal and a near field EGM signal for processing and analysis performed to detect the capture type following a generated His-Purkinje pacing pulse.

It is to be understood that although IMD 14 is described as an implantable cardioverter defibrillator capable of delivering both low voltage cardiac pacing therapies and high voltage cardioversion and defibrillation (CV/DF) shocks, IMD 14 may be configured as a dual-chamber pacemaker in other examples coupled to only RA lead 16 and His pacing and sensing lead 18 without having CV/DF shock delivery capabilities and without being coupled to a third lead, such as RV lead 17. In still other examples, IMD 14 may be a single chamber pacing device with single chamber or dual chamber sensing. For example, IMD 14 may be coupled only to His pacing and sensing lead 18 for sensing cardiac electrical signals and delivering His-Purkinje pacing pulses for at least maintaining a minimum ventricular rate. His pacing and sensing lead 18 may carry additional sensing electrodes positioned within the RA when lead 18 is positioned for delivering His-Purkinje pacing pulses such that IMD 14 is capable of dual chamber (atrial and ventricular) sensing and delivery of atrial synchronized ventricular pacing.

An external device 50 is shown in telemetric communication with IMD 14 by a communication link 60. External device 50 may be embodied as a programmer used in a hospital, clinic or physician's office to retrieve data from IMD 14 and to program operating parameters and algorithms in IMD 14 for controlling IMD functions. External device 50 may alternatively be embodied as a home monitor or handheld device for retrieving data from IMD 14. External device 50 may be used to program cardiac signal sensing parameters, cardiac rhythm detection parameters, pacing and CV/DF therapy control parameters and capture detection control parameters used by IMD 14.

External device 50 may include a processor 52, memory 53, display unit 54, user interface 56 and telemetry unit 58. Processor 52 controls external device operations and processes data and signals received from IMD 14. Display unit 54, which may include a graphical user interface, displays data and other information to a user for reviewing IMD operation and programmed parameters as well as cardiac electrical signals retrieved from IMD 14. Data obtained from IMD 14 via communication link 60 may be displayed on display 54. For example, a clinician may view cardiac electrical signals received from IMD 14 and/or results of His capture threshold testing and monitoring or data derived therefrom. For example, processor 52 may generate a report of SHP, NSHP and VM capture thresholds based on capture threshold tests performed by IMD 14 for display to a user on display 54.

User interface 56 may include a mouse, touch screen, keypad or the like to enable a user to interact with external device 50 to initiate a telemetry session with IMD 14 for retrieving data from and/or transmitting data to IMD 14, including programmable parameters for controlling pacing capture determination and for setting His-Purkinje pacing pulse amplitude and pulse width. Telemetry unit 58 includes a transceiver and antenna configured for bidirectional communication with a telemetry circuit included in IMD 14 and is configured to operate in conjunction with processor 52 for sending and receiving data relating to IMD functions via communication link 60, which may include data relating to His-Purkinje system and ventricular myocardial capture management, such as capture thresholds determined for SHP capture, NSHP capture and VM capture. Thresholds or other parameters used for detecting SHP capture, NSHP capture and VM capture according to techniques disclosed herein may be programmed into IMD 14 using external device 50.

Communication link 60 may be established between IMD 14 and external device 50 using a wireless radio frequency (RF) link such as BLUETOOTH®, Wi-Fi, or Medical Implant Communication Service (MICS) or other RF or communication frequency bandwidth or communication protocols. Data stored or acquired by IMD 14, including physiological signals or associated data derived therefrom, results of device diagnostics, and histories of detected rhythm episodes, delivered therapies, and capture determinations may be retrieved from IMD 14 by external device 50 following an interrogation command.

Figure 1B:
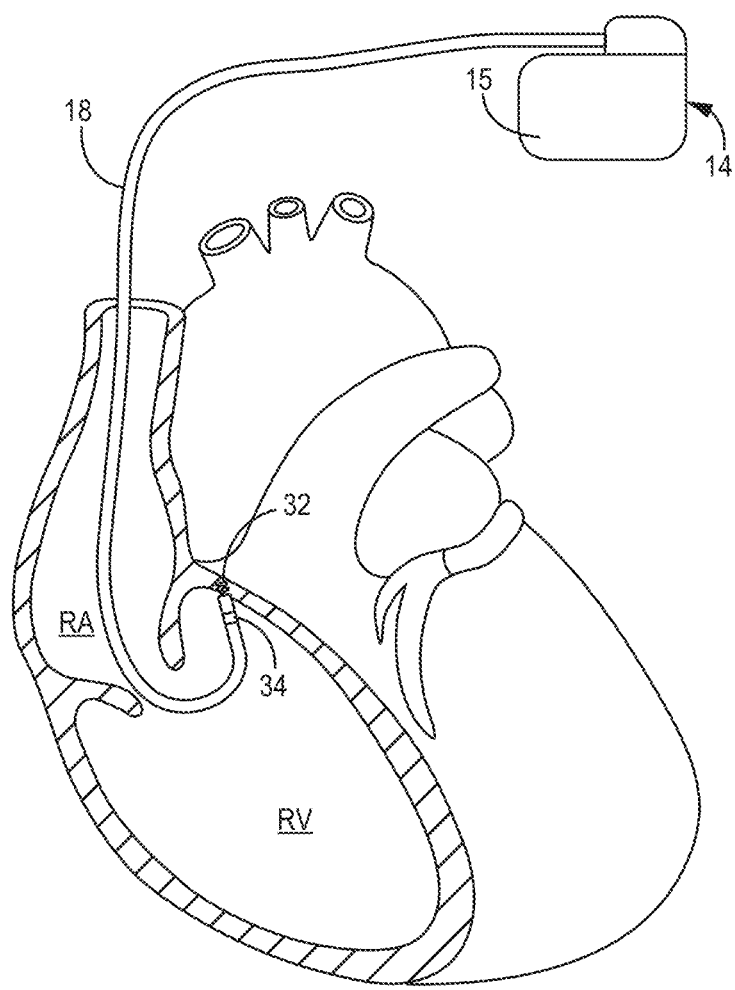
FIG. 1B is a conceptual diagram of an implantable medical device (IMD) coupled to a His pacing and sensing lead advanced to an alternative location in a patient's heart.

FIG. 1B is a conceptual diagram of an IMD 14 coupled to His pacing and sensing lead 18 advanced to an alternative location within the heart. In this example, the distal portion of His pacing and sensing lead 18 is advanced within the RV for sensing cardiac electrical signals and delivering pacing pulses to or in the vicinity of the His bundle. IMD 14 may be a single chamber device coupled only to His pacing and sensing lead 18 as shown. In other examples, IMD 14 may be a dual chamber device and be coupled to RA lead 16 as shown in FIG. 1A.

In this example, the tip electrode 32 is placed in or along the ventricular septal wall, e.g., high along the ventricular septal wall near the His bundle. Tip electrode 32 may be paired with the return anode ring electrode 34 for delivering His-Purkinje pacing pulses and for receiving raw near field cardiac signals that are used to produce a near field EGM signal, also referred to herein as a "near field cardiac electrical signal" or "near field His-Purkinje signal," that is analyzed for detecting capture type. The tip electrode 32 or the ring electrode 34 may be paired with IMD housing 15 for receiving a raw far field cardiac electrical signal that is used to produce a far field EGM signal, also referred to herein as a "far field cardiac electrical signal," and generate a differential signal from the far field EGM signal, both of which may be analyzed for determining capture type during His-Purkinje pacing according to the techniques disclosed herein.

Figure 2:
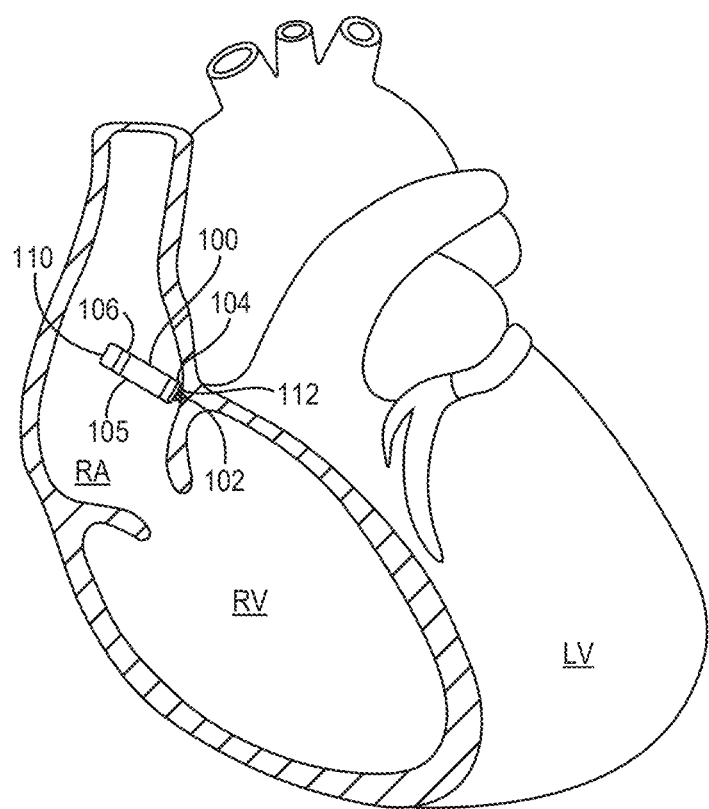
FIG. 2 is a conceptual diagram of a leadless intracardiac pacemaker positioned within the right atrium for providing His-Purkinje system pacing.

FIG. 2 is a conceptual diagram of a leadless intracardiac pacemaker 100 positioned within the RA for providing ventricular pacing via the His bundle. Pacemaker 100 may include a distal tip electrode 102 extending away from a distal end 112 of the pacemaker housing 105. Intracardiac pacemaker 100 is shown implanted in the RA of the patient's heart to place distal tip electrode 102 for delivering pacing pulses to the His bundle. For example, the distal tip electrode 102 may be inserted into the inferior end of the interatrial septum, beneath the AV node and near the tricuspid valve annulus to position tip electrode 102 in, along or proximate to the His bundle. In other examples, leadless intracardiac pacemaker 100 may be implanted within the right ventricle, e.g., high along the ventricular septum, for positioning distal tip electrode 102 in the vicinity of the His bundle or along the native His-Purkinje system. Distal tip electrode 102 may be a helical electrode providing fixation to anchor the pacemaker 100 at the implant position. In other examples, pacemaker 100 may include a fixation member that includes one or more tines, hooks, barbs, helices or other fixation member(s) that anchor the distal end of the pacemaker 100 at the implant site.

A portion of the distal tip electrode 102 may be electrically insulated such that only the most distal end of tip electrode 102, furthest from housing distal end 112, is exposed to provide targeted pacing at a tissue site that includes a portion of the His bundle. One or more housing-based electrodes 104 and 106 may be carried on the surface of the housing of pacemaker 100. Electrodes 104 and 106 are shown as ring electrodes circumscribing the longitudinal sidewall of pacemaker housing 105 extending from distal end 112 to proximal end 110. In other examples, a return anode electrode used in sensing and pacing may be positioned on housing proximal end 110. Pacing of the His-Purkinje system may be achieved using the distal tip electrode 102 as the cathode electrode and either of the housing-based electrodes 104 and 106 as the return anode.

Cardiac electrical signals produced by heart 8 may be sensed by pacemaker 100 using a sensing electrode pair selected from electrodes 102, 104 and 106. For example, a near field signal may be sensed using distal tip electrode 112 and distal housing-based electrode 104. A second cardiac electrical signal, which is a relatively more far-field signal, may be sensed using electrodes 104 and 106. The raw cardiac electrical signals may be processed by sensing and control circuitry included in pacemaker 100, e.g., as described below in conjunction with FIG. 3, for producing a near field His-Purkinje signal and a far field cardiac electrical signal. The near field and far field signals may be further processed and analyzed for determining capture type by discriminating between at least SHP capture, NSHP capture, VM capture and loss of capture.

Figure 3:
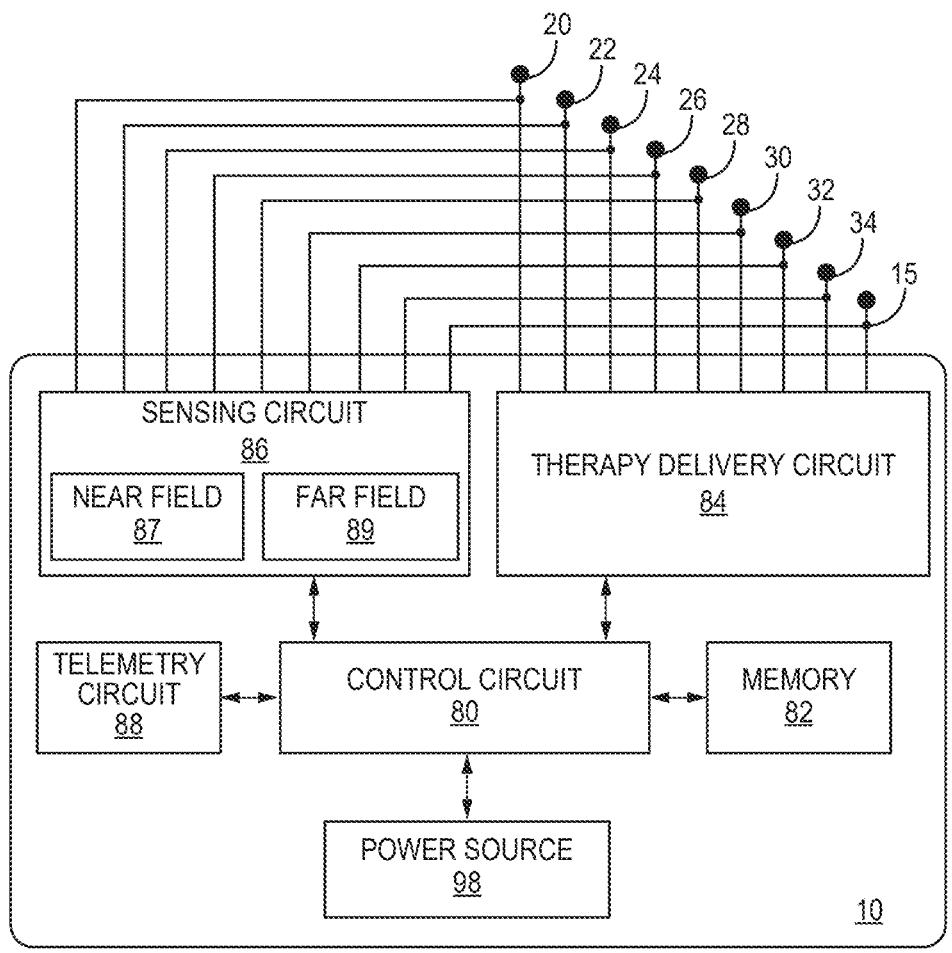
FIG. 3 is a schematic diagram of circuitry that may be enclosed within a medical device configured to perform His-Purkinje system pacing and capture detection according to the techniques disclosed herein.

FIG. 3 is a schematic diagram of circuitry that may be enclosed within a medical device configured to perform His-Purkinje pacing and capture detection using techniques disclosed herein. The block diagram of FIG. 3 is described with reference to IMD 14 coupled to electrodes carried by RA lead 16, RV lead 17 and His pacing and sensing lead 18 as shown in FIG. 1A for the sake of illustration, but it is to be understood that the functionality attributed to the various circuits and components shown in FIG. 3 for performing His-Purkinje pacing and detection and discrimination of SHP capture, NSHP capture, VM capture and loss of capture may be similarly implemented in the intracardiac pacemaker 100 of FIG. 2 or other medical device systems capable of delivering His-Purkinje pacing pulses and sensing cardiac electrical signals, e.g., including external pacemakers coupled to one or more transcutaneous medical electrical leads.

Housing 15 is represented as an electrode in FIG. 3 for use in cardiac electrical signal sensing and, in some examples, for delivery of cardiac electrical stimulation pulses such as unipolar pacing pulses or cardioversion/defibrillation shocks. The electronic circuitry enclosed within housing 15 includes software, firmware and hardware that cooperatively monitor cardiac electrical signals, determine when a pacing therapy is necessary, and deliver electrical pacing pulses to the patient's heart as needed according to programmed pacing mode and pacing pulse control parameters. The electronic circuitry includes a control circuit 80, memory 82, therapy delivery circuit 84, sensing circuit 86, telemetry circuit 88 and power source 98.

Power source 98 provides power to the circuitry of IMD 14 including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86, and 88 are to be understood from the general block diagram of FIG. 3 but are not shown for the sake of clarity. For example, power source 98 may be coupled to one or more charging circuits included in therapy delivery circuit 84 for providing the power needed to charge holding capacitors included in therapy delivery circuit 84 that are discharged at appropriate times under the control of control circuit 80 for delivering pacing pulses. Power source 98 is also coupled to components of sensing circuit 86, such as sense amplifiers, analog-to-digital converters, switching circuitry, etc., telemetry circuit 88 and memory 82 to provide power to the various components and circuits as needed.

The functional blocks shown in FIG. 3 represent functionality included in IMD 14 and may include any discrete and/or integrated electronic circuit components that implement analog and/or digital circuits capable of producing the functions attributed to IMD 14 (or pacemaker 100) herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern cardiac medical device system, given the disclosure herein, is within the abilities of one of skill in the art.

Control circuit 80 communicates, e.g., via a data bus, with therapy delivery circuit 84 and sensing circuit 86 for cooperatively sensing cardiac electrical signals and controlling delivery of cardiac electrical stimulation therapies in response to sensed cardiac events, e.g., P-waves attendant to atrial depolarizations and R-waves attendant to ventricular depolarizations, or the absence thereof. The available electrodes are electrically coupled to therapy delivery circuit 84 for delivering electrical stimulation pulses and/or to sensing circuit 86 for sensing cardiac electrical signals produced by the heart, including both intrinsic signals (such as intrinsic R-waves) produced by the heart in the absence of a pacing pulse that captures the heart and evoked response signals following a delivered pacing pulse of sufficient energy to cause capture.

Sensing circuit 86 may include two or more sensing channels for sensing raw cardiac electrical signals from two or more sensing electrode vectors. For example, a RA signal may be sensed using electrodes 20 and 22, an RV signal may be sensed using electrodes 28 and 30, and a near field His-Purkinje signal may be sensed using electrodes 32 and 34. As described below, a raw near field His-Purkinje signal may be sensed by one sensing channel, shown as near field sensing channel 87, for example using electrodes 32 and 34 of His pacing and sensing lead 18. A raw far field signal may be sensed by a second sensing channel, shown as far field sensing channel 89, using a second electrode vector having electrodes spaced further apart than the electrodes of the near field sensing electrode vector, e.g., using tip electrode 32 and housing 15.

As used herein, a "near field" signal refers to a cardiac electrical signal received from a sensing electrode vector including at least one electrode positioned at or proximate to the His bundle, at or in the vicinity of the site of His pacing pulse delivery, such that the near field signal may also be referred to as a "near field His-Purkinje signal." The near field His-Purkinje signal may or may not include a His-Purkinje evoked response signal depending on whether a delivered pacing pulse captured or not. The near field His-Purkinje signal may include an evoked response signal caused by SHP capture, an evoked response signal caused by NSHP capture or an evoked response signal caused by VM capture.

As used herein, a raw "far field" signal refers to a raw cardiac electrical signal received from a sensing electrode vector that is relatively further away from the His-Purkinje system than the electrode vector used to sense the raw near field His-Purkinje signal and/or has a greater inter-electrode distance between the two electrodes defining the far field sensing electrode vector than the inter-electrode distance between the two electrodes defining the near field His-Purkinje sensing electrode vector. A far field cardiac electrical signal produced from the raw far field signal by sensing circuit 86 may be more representative of the global activation of the ventricles as opposed to the near field signal being more representative of local tissue activation at or near the pacing site. The far field cardiac electrical signal may include an evoked response signal associated with SHP capture, NSHP capture or VM capture. Examples of differences in the evoked response signals of the near field and far field cardiac electrical signals during different capture types that may be determined and used by control circuit 80 for discriminating between capture types are discussed below in conjunction with FIGS. 5 through 8.

In examples presented herein, the raw near field His-Purkinje signal and the raw far field signal may be sensed using electrodes carried by His pacing and sensing lead 18 (FIGS. 1A and 1B) and IMD housing 15 or, in the example of FIG. 2, using only leadless, housing-based electrodes 104, 106 and 112. For example, the raw near field His-Purkinje signal may be sensed between His pacing lead electrodes 32 and 34, sometimes referred to as a "tip-to-ring" sensing electrode vector. The raw far field cardiac electrical signal may be sensed between His pacing lead tip electrode 32 and housing 15, sometimes referred to as a "tip-to-can" sensing electrode vector. A raw far field cardiac electrical signal may alternatively be sensed between the ring electrode 34 and housing 15.

In other examples, when additional leads and electrodes are available, the raw far field signal may be sensed using an electrode carried by RA lead 16 and the IMD housing 15, e.g., electrode 20 and housing 15 or electrode 22 and housing 15. In examples that include RV lead 17, the raw far field signal may be sensed using RV coil electrode 24 paired with housing 15, SVC coil electrode 26 paired with housing 15, or RV coil electrode 24 paired with SVC coil electrode 26.

Sensing circuit 86 may include switching circuitry for selectively coupling a near field sensing electrode pair from the available electrodes to the near field sensing channel 87 for sensing a raw near field His-Purkinje signal and for selectively coupling a far field sensing electrode pair to far field sensing channel 89 for sensing a raw far field signal that is "far field" relative to the site of delivering His-Purkinje pacing pulses. The far field sensing electrode pair may exclude at least one or both of the electrodes used to deliver the His-Purkinje pacing pulses. Switching circuitry may include a switch array, switch matrix, multiplexer, or any other type of switching device suitable to selectively couple components of sensing circuit 86 to selected electrodes.

Each of near field sensing channel 87 and far field sensing channel 89 may include an input filter for receiving a raw cardiac electrical signal from a respective pair of sensing electrodes, a pre-amplifier, an analog-to-digital converter and a bandpass filter for producing a multi-bit digital cardiac electrical signal, which may be referred to as an "EGM" signal when the raw signal is sensed from within a heart chamber, for use in detecting His-Purkinje capture and discriminating between any of SHP capture, NSHP capture, VM capture and loss of capture. Features of the near field and far field cardiac electrical signals produced by sensing circuit 86 may be determined by control circuit 80. As described below, control circuit 80 may include a software, firmware or hardware implemented differentiator for producing a differential signal from one or both of the near field His-Purkinje signal and the far field cardiac electrical signal for use in determining the type of capture following a His-Purkinje pacing pulse. Signal features may be determined from the filtered, amplified cardiac electrical signals without rectification in order to preserve the polarity and shape of the signal features. However, it is recognized that in some examples each sensing channel 87 and 89 may include a rectifier to produce a rectified signal for used in detecting intrinsic R-waves or pacing evoked responses. As described below in conjunction with FIGS. 5-8, features of the post-pace far field cardiac electrical signal and near field His-Purkinje signals following a His-Purkinje pacing pulse may be used to detect His-Purkinje pacing pulse capture and discriminate between different types of capture based upon features of the post-pace signal in the near field and far field signals. The post-pace signal following a His-Purkinje pacing pulse that captures the His-Purkinje system and/or the ventricular myocardium may also be referred to herein as an "evoked response signal" that is attendant to the evoked depolarizations caused by the pacing pulse, which may be sensed by sensing circuit 86.

As described below in conjunction with FIG. 4, sensing circuit 86 may include cardiac event detection circuitry, which may include one or more sense amplifiers, filters, rectifiers, threshold detectors, comparators, analog-to-digital converters (ADCs), timers or other analog or digital components, for detecting cardiac electrical events. For example, an atrial event detector may be included in sensing circuit 86 for detecting intrinsic P-waves attendant to intrinsic atrial depolarizations using one or both of electrodes 20 and 22 carried by RA lead 16. A ventricular event detector may be included in sensing circuit 86 for detecting intrinsic R-waves attendant to intrinsic ventricular depolarizations using electrodes 32 and 34 carried by His pacing and sensing lead 18 and/or using electrodes 24, 26, 28 and/or 30 carried by RV lead 17. A cardiac event sensing threshold, such as a P-wave sensing threshold or an R-wave sensing threshold, may be automatically adjusted by sensing circuit 86 under the control of control circuit 80, e.g., based on timing intervals and sensing threshold values determined by control circuit 80, stored in memory 82, and/or controlled by hardware, firmware and/or software of control circuit 80 and/or sensing circuit 86. The R-wave sensing threshold, for example, may be controlled to start at a starting threshold voltage following a post-ventricular blanking period then decrease according to a decay profile until reaching a minimum sensing threshold. The minimum R-wave sensing threshold may be set to a programmed sensitivity of the R-wave detection circuitry in the respective near field sensing channel 84 or in the far field sensing channel 89. The sensitivity, programmed to a voltage level typically in millivolts, is the lowest voltage level above which a cardiac event, an R-wave in this example, can be sensed by the cardiac event detection circuitry.

Upon detecting a cardiac electrical event based on a sensing threshold crossing, sensing circuit 86 may produce a sensed event signal that is passed to control circuit 80. For example, an atrial event detector may produce a P-wave sensed event signal in response to a P-wave sensing threshold crossing. A ventricular event detector may produce an R-wave sensed event signal in response to an R-wave sensing threshold crossing. The sensed event signals are used by control circuit 80 for setting pacing escape interval timers that control the basic time intervals used for scheduling cardiac pacing pulses. Control circuit 80 may include various timers or counters for counting down an atrioventricular (AV) pacing interval, a VV pacing interval, an AA pacing interval, etc. A sensed event signal may trigger or inhibit a pacing pulse depending on the particular programmed pacing mode. For example, a P-wave sensed event signal received from sensing circuit 86 may cause control circuit 80 to inhibit a scheduled atrial pacing pulse and schedule a His-Purkinje pacing pulse at the programmed AV pacing interval. If the AV pacing interval expires before control circuit 80 receives an R-wave sensed event signal from sensing circuit 86, therapy delivery circuit 84 may respond by generating and delivering a His pacing pulse at the AV pacing interval following the sensed P-wave and in this way deliver atrial-synchronized ventricular pacing. If an R-wave sensed event signal is received from sensing circuit 86 before the AV pacing interval expires, the scheduled His pacing pulse may be inhibited. The AV pacing interval controls the amount of time between an atrial event, paced or sensed, and a His-Purkinje pacing pulse to promote AV synchrony. A medical device capable of determining His-Purkinje pacing pulse capture type according to techniques disclosed herein may be configured for delivering ventricular bradycardia pacing therapy, atrial synchronized ventricular pacing, rate responsive pacing, cardiac resynchronization therapy (CRT), anti-tachycardia pacing therapy or other pacing therapies which may include pacing the ventricles via the His bundle.

Therapy delivery circuit 84 may include charging circuitry, one or more charge storage devices such as one or more holding capacitors, an output capacitor, and switching circuitry that controls when the holding capacitor(s) are charged and discharged across the output capacitor to deliver a pacing pulse to a selected pacing electrode vector coupled to the therapy delivery circuit 84. Therapy delivery circuit 84 may include one or more pacing channels. In the example of IMD 14, therapy delivery circuit 84 may include an RA pacing channel, a His pacing channel and an RV pacing channel each including one or more holding capacitors, one or more switches, and an output capacitor for producing pacing pulses delivered by the respective RA lead 16 (electrodes 20 and 22), RV lead 17 (electrodes 24, 26, 28 and 30) and His pacing and sensing lead 18 (electrodes 32 and 34). Charging of a holding capacitor to a programmed pacing voltage amplitude and discharging of the capacitor for a programmed pacing pulse width may be performed by therapy delivery circuit 84 according to control signals received from control circuit 80. For example, a pace timing circuit included in control circuit 80 may include programmable digital counters set by a microprocessor of the control circuit 80 for controlling the basic pacing time intervals associated with various single chamber or dual chamber pacing modes, CRT or anti-tachycardia pacing sequences. The microprocessor of control circuit 80 may also set the amplitude, pulse width, polarity or other characteristics of the cardiac pacing pulses, which may be based on programmed values stored in memory 82.

In some examples, IMD 14 may be configured to detect non-sinus tachycardia and deliver anti-tachycardia pacing (ATP). Therapy delivery circuit 84 may include high voltage therapy circuitry for generating high voltage shock pulses in addition to low voltage therapy circuitry for generating low voltage pacing pulses. In response to detecting atrial or ventricular tachycardia or fibrillation, control circuit 80 may control therapy delivery circuit 84 to deliver a CV/DF shock. The high voltage therapy circuitry may include high voltage capacitors and high voltage charging circuitry for generating and delivering CV/DF shock pulses using coil electrodes 24 and 26 and/or housing 15.

Control parameters utilized by control circuit 80 for sensing cardiac events and controlling pacing therapy delivery may be programmed into memory 82 via telemetry circuit 88. Telemetry circuit 88 includes a transceiver and antenna for communicating with an external device 50 (FIG. 1A) using radio frequency communication or other communication protocols as described above. Under the control of control circuit 80, telemetry circuit 88 may receive downlink telemetry from and send uplink telemetry to the external device 50. In some cases, telemetry circuit 88 may be used to transmit and receive communication signals to/from another medical device implanted in the patient.

Figure 4:
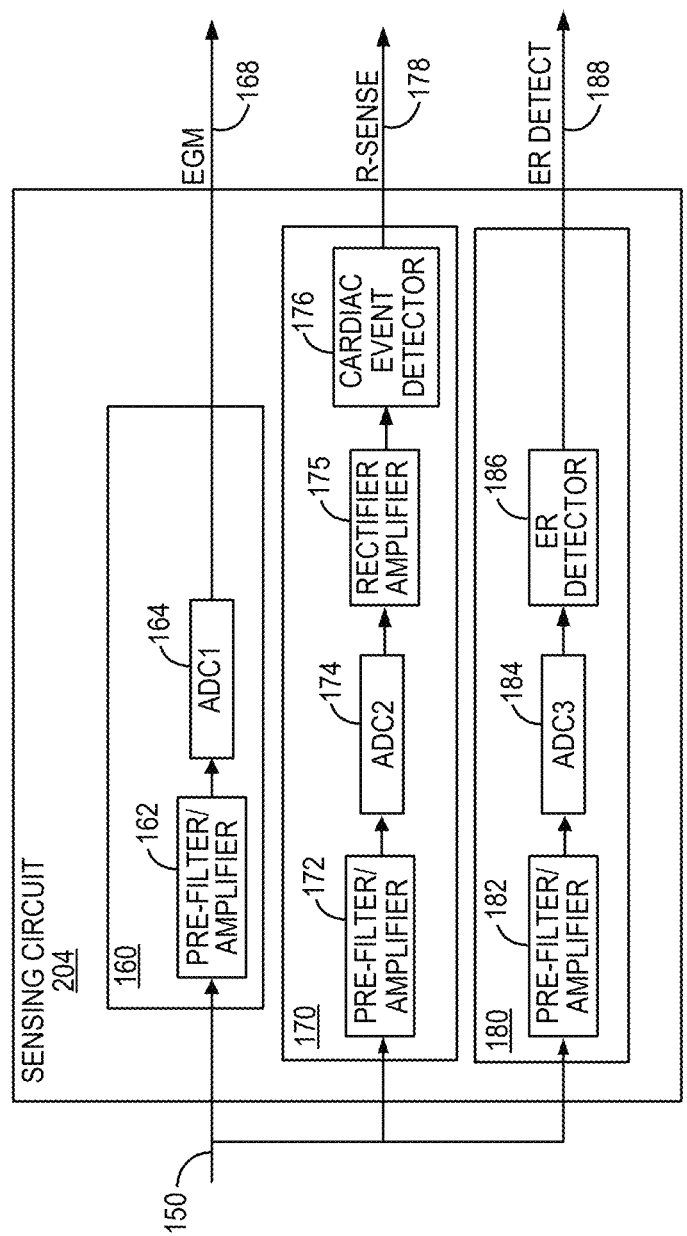
FIG. 4 is a schematic diagram of circuitry that may be included in the sensing circuit shown in FIG. 3.

FIG. 4 is a schematic diagram of circuitry that may be included in the sensing circuit 86 shown in FIG. 3. Each of the near field channel 87 and far field channel 89 (and any additional sensing channels included in sensing circuit 86 such as an RA channel), may include EGM signal circuit 160, cardiac event sensing circuit 170, and/or evoked response detection circuit 180. Accordingly, the circuits 160, 170 and 180 may represent components included in one of the near field channel 87 or the far field channel 89 shown in FIG. 3. As such, a raw input signal 150 sensed from a near field His-Purkinje sensing electrode pair or a far field sensing electrode pair may be received as input to each of the EGM signal circuit 160, the cardiac event sensing circuit 170 and the evoked response detection circuit 180.

The EGM signal circuit 160 may include a pre-filter and amplifier circuit 162 configured to receive the raw input signal 150 from a sensing electrode vector. In some examples, the EGM signal circuit 160 includes an analog filter and amplifier for producing a wide band filtered cardiac electrical signal, shown as output EGM signal 168, that is passed to control circuit 80. Pre-filter and amplifier circuit 162, which includes an analog filter in some examples, may have a relatively wide bandpass of 3 to 100 Hz for example. Analog-to-digital converter 164 (ADC1) may sample the wideband filtered signal at a desired sampling rate, e.g., 256 Hz, to produce the EGM signal 168 passed to control circuit 80. Depending on the sensing electrode vector selected to provide input signal 150, EGM signal 168 may be a far field cardiac electrical signal or a near field His-Purkinje signal, which may be further processed and analyzed by control circuit 80 according to the techniques disclosed herein for determining capture type following a His-Purkinje pacing pulse.

The input signal 150 received from a sensing electrode pair may also be received by cardiac event sensing circuit 170, shown including a pre-filter/amplifier 172, ADC2 174, rectifier/amplifier 175 and cardiac event detector 176. Pre-filter/amplifier 172 may include a relatively narrow band filter, which may be a digital filter, having a high pass frequency of 10 to 20 Hz and a low pass frequency of 40 to 60 Hz, as examples, for passing frequencies associated with intrinsic cardiac event signals, e.g., R-waves attendant to ventricular depolarization in the absence of a pacing pulse. The narrow-band filtered and sampled signal is passed to rectifier 175 from ADC2 174 to provide a rectified signal to a cardiac event detector 176, which may include a comparator, sense amplifier or other circuitry configured to detect an intrinsic R-wave (or a P-wave in the case of an atrial channel) that crosses an R-wave (or P-wave) sensing threshold. Cardiac event sensing circuit 170 produces a sensed cardiac event signal, shown in the example of FIG. 4 as an R-wave sensed event signal 178, which is passed to control circuit 80. As described above, control circuit 80 receives R-wave sensed event signals for use in determining the ventricular rate and controlling ventricular pacing.

In some examples, a sensing channel of sensing circuit 204 may include evoked response detection circuit 180. Evoked response detection circuit 180 may include a pre-filter/amplifier 182, ADC3 184 and evoked response (ER) detector 186 for producing an ER detect signal 188 that is passed to control circuit 80. The pre-filter/amplifier 182 may include a relatively wideband filter, which may be a digital filter, for passing an evoked response signal to ADC 3 184. The ER detector 186 receives the sampled, wideband filtered signal and compares the signal to an ER detection threshold amplitude during an ER window set in response to delivery of a His-Purkinje pacing pulse. When the wideband filtered signal crosses the ER detection threshold within the ER window, the ER detector 186 passes the ER detect signal 188 to control circuit 80. The ER window may extend, for example, 150 milliseconds (ms) to 180 ms after the His-Purkinje pacing pulse. The ER detection threshold may be about 0.5 to 1.5 millivolt, as an example. As disclosed herein, in response to receiving an ER detect signal 188 from sensing circuit 204, control circuit 80 may process and determine features of the EGM signal 168 for discriminating between SHP, NSHP and VM capture as described below.

In particular, the EGM signal 168 may be a non-rectified signal. When a His-Purkinje pacing pulse captures tissue at the pacing site and the His pacing and sensing tip electrode, e.g., electrode 32 in FIG. 1A, is used to sense the raw far field signal, the evoked response signal in the far field cardiac electrical signal has a negative polarity as the depolarization wavefront is traveling away from the sensing electrode positioned in the vicinity of the His-Purkinje pacing site. Accordingly, features of the EGM signal determined from the negative polarity portion of the evoked response signal may be determined and used in discriminating between capture types.

The circuitry shown in FIG. 4 may be included in each of the near field sensing channel 87 and the far field sensing channel 89. In some examples, only one of the near field channel 87 or the far field channel 89 includes cardiac event sensing circuit 170 for sensing R-waves. Only one of the near field channel 87 or the far field channel 89 may include ER detection circuit 180 for detecting evoked responses following His-Purkinje pacing pulses. In still other examples, ER detection circuit 180 may be omitted and control circuit 80 may be configured to compare EGM signal 168 (from either or both of the near field and/or far field channels 87 and 89) for detecting an evoked response based on an evoked response threshold crossing by the EGM signal within an ER window following a His-Purkinje pacing pulse. While EGM signal circuit 160, cardiac event sensing circuit 170, and evoked response detection circuit 180 are each shown as separate circuits it is to be understood that in some cases the EGM signal circuit 160, cardiac event sensing circuit 170, and/or evoked response detection circuit 180 may include some shared components, such as a shared filter, shared amplifier, shared ADC, shared rectifier or other components with an output signal of any shared components routed to the separate circuits 160, 170 and/or 180 as needed.

Figure 5:
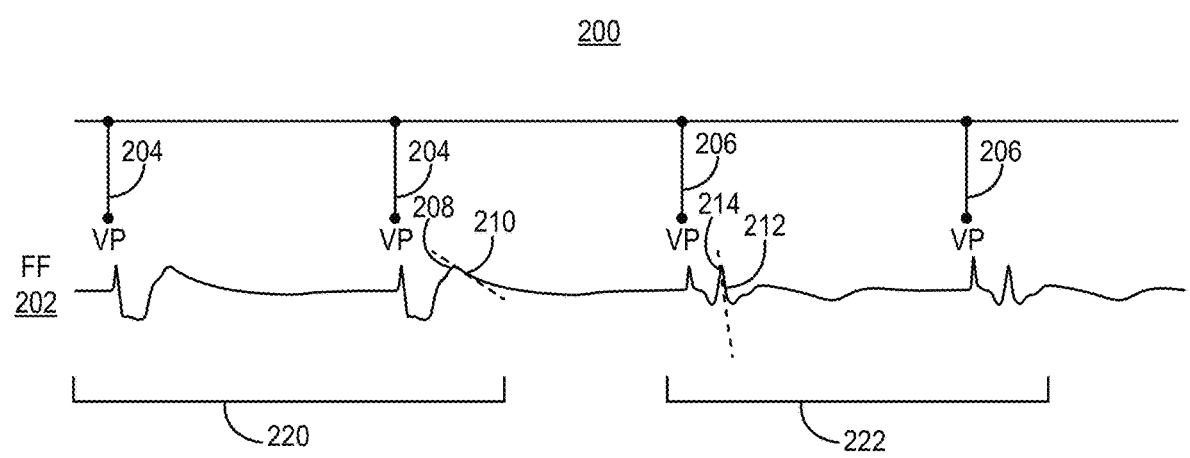
FIG. 5 is a timing diagram including a cardiac electrical signal and pacing pulse markers.

FIG. 5 is a timing diagram 200 including a far field (FF) cardiac electrical signal 202 pacing pulse markers 204 and 206 marking the time that a pacing pulse is delivered. The cardiac electrical signal 202 may correspond to a far field cardiac electrical signal produced from the raw signal received using at least one electrode located away from the His bundle and one electrode located at or near the pacing site. For example, far field cardiac electrical signal 202 may be produced from the raw signal sensed using tip electrode 32 of His pacing lead 18 positioned at or near the His-Purkinje system paired with the IMD housing 15 in the example of FIG. 1A or 1B or the tip electrode 112 and most proximal ring electrode 106 in the example of FIG. 2.

The delivered pacing pulse energy of a His-Purkinje system pacing pulse 204 or 206 may be adjusted by therapy delivery circuit 84, under the control of control circuit 80, e.g., by adjusting the pacing pulse amplitude and/or the pacing pulse width. The delivered pacing pulse energy depends on the pacing pulse amplitude, pacing pulse width, and lead and electrode impedance. In some examples, the pacing pulse width is set to a fixed value, e.g., 0.5 to 1 millisecond, and the pacing pulse amplitude is increased or decreased, e.g., between 0.25 and 8 Volts, to increase or decrease the pacing pulse energy to determine a capture threshold and set a pacing pulse energy to be a safety margin greater than a pacing capture threshold.

In FIG. 5, the first two ventricular pacing pulses 204 are delivered at a pacing pulse energy that results in NSHP capture 220. The second two pacing pulses 206 are delivered at a pacing pulse energy that results in SHP capture 222. The pulse energy of pacing pulses 204 may be greater than the pulse energy of pacing pulses 206 such that the NSHP capture threshold, which includes His-Purkinje capture and ventricular myocardial capture, is greater than the SHP capture threshold.

As observed from the far field cardiac electrical signal 202 in this example, the negative slope 212 following the maximum positive peak 214 in the evoked response signal during SHP capture 222 is steeper than the negative slope 210 following the maximum positive peak 208 in the evoked response signal during NSHP capture 220. This difference in the magnitude of the post-peak negative slopes 210 and 212 (following a maximum positive peak of the non-rectified evoked response signals in the far field cardiac electrical signal) may be used by control circuit 80 to distinguish SHP capture 222 from other types of capture, e.g., NSHP capture 220 as well as VM capture. For example, the absolute value of the magnitude of post-peak slopes 210 and 212 may be compared to a slope threshold by control circuit 80 for detecting SHP capture. When the absolute value of the post-peak slope 212 is greater than the slope threshold, SHP capture may be detected by control circuit 80. In some examples, control circuit 80 may adjust the pulse energy, e.g., by decreasing the pacing pulse amplitude, of His-Purkinje pacing pulses 204 and 206, until a threshold increase (in absolute value) in the post-peak slope is detected, indicating a change from NSHP capture to SHP capture. There may be other criteria required to be satisfied in combination with the post-peak slope threshold in order to detect SHP capture. In some examples, when the post-peak slope 210 is less than the slope threshold, SHP capture is not detected. Control circuit 80 may perform additional analysis of one or both of the far field signal 202 and near field His-Purkinje signal for determining the capture type as either NSHP capture or VM capture. In other examples, control circuit 80 may apply alternative SHP capture detection criteria for detecting SHP capture in response to the post-peak slope 210 being less than the slope threshold as described below in conjunction with FIG. 12.

Control circuit 80 may receive the far field cardiac electrical signal 202 from sensing circuit 86 and determine the post-peak slopes 210 and 212 by detecting the maximum positive peak 208 or 214 following delivery of a respective His-Purkinje pacing pulse 204 or 206 and determining the differences between succeeding far field signal sample points following the maximum peak 208 or 214, respectively. Control circuit 80 may step through consecutive or moving sets of sample points to determine a maximum difference between two sample points, which may be consecutive sample points or sample points that are a predetermined time interval or predetermined number of sample points apart, following the maximum positive peak 208 or 214. For example, the difference between the first and third sample points of three consecutive sample points, which may be sampled at 256 Hz, may be determined. Differences may be determined between the first and third sample points that occur a fixed number of sample points (or fixed time interval) following the maximum positive peak 208 or 214. In other examples, differences between alternating sample points for a predetermined number of sample points following the maximum positive peak 208 or 214 may be determined and a maximum difference is identified from among the determined differences. Alternatively, differences between selected sample points following maximum positive peak 208 or 214 may be determined until the difference is less than a low slope threshold (indicating a return to baseline). The maximum difference may then be identified and compared to a slope threshold for discriminating SHP capture and other types of capture.

In other examples, the difference between the amplitude of the maximum positive peak 208 or 214 and the amplitude of the nth sample point after the maximum positive peak may be determined. In some examples, a single slope is determined between predetermined sample points selected relative to the maximum positive peak 208 or 214 of the far field signal 202. In other examples, multiple post-peak sample point amplitude differences are determined, and a maximum difference is determined as the post-peak slope. The absolute value of the determined sample point amplitude difference (in volts) may be used as a metric of the post-peak negative slope and compared to a slope threshold in volts since the time interval between sample points used to determine the sample point amplitude difference may be fixed based on the sampling frequency, e.g., 256 Hz. In other examples, the post-peak slope may be determined as a change in amplitude over time (volts per millisecond) and compared to a slope threshold in volts per millisecond, for example.

Figure 6:
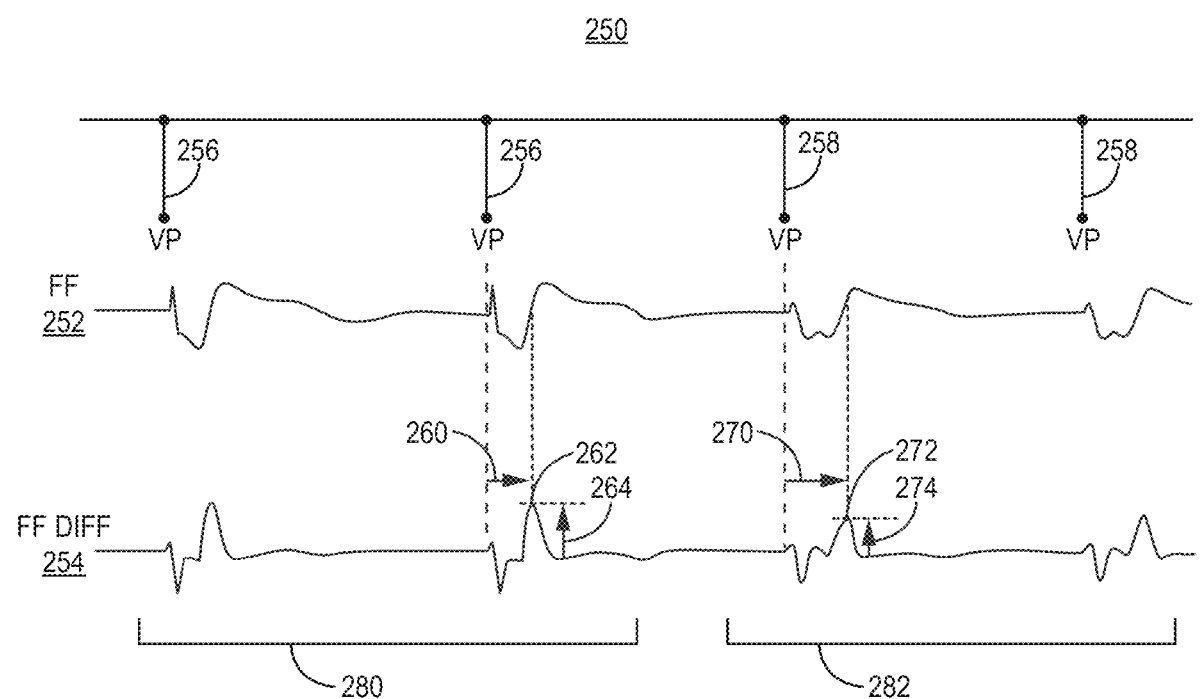
FIG. 6 is a diagram of a far field cardiac electrical signal and a differential signal generated from the far field cardiac electrical signal.

FIG. 6 is a diagram 250 of a far field cardiac electrical signal 252 produced by sensing circuit 86 (e.g., EGM signal 168) as described in conjunction with FIG. 4) and a differential signal 254 derived from the far field cardiac electrical signal 252. His-Purkinje pacing pulses 256 result in NSHP capture 280, and His-Purkinje pacing pulses 258, delivered at a lower pacing pulse energy (e.g., lower pulse amplitude) result in VM capture 282 (loss of His-Purkinje capture). The differential signal 254 may be derived from the far field signal 252 by control circuit 80. For example, control circuit 80 of FIG. 3 may include a low pass filter and a differential filter implemented in hardware, software or firmware. In one example, the far field cardiac electrical signal 252 is sampled at 256 Hz and passed through a low pass filter having an upper cut off frequency of 12 Hz. The low pass filter output may be determined from the equation $y(n)=x(n-1)+x(n)+y(n-1)-y(n-1)/4$ where $x(n)$ and $x(n-1)$ are the nth and nth$-1$ sample points of the far field cardiac electrical signal 252 and $y(n-1)$ is the preceding low pass filtered sample point.

The differential signal 254 may be determined using five consecutive sample points of the low pass filtered far field signal in one example. Each sample point of differential signal 254 may be determined using a five-point difference equation, e.g., $Z(n)=2*y(n-2)-y(n-1)+y(n+1)-2*y(n+2)$, though other coefficients and/or other number of sample points may be used to estimate a differential signal of the low pass filtered far field signal. It is further recognized that different filters or equations may be used when a different sampling rate is used other than 256 Hz as used in this is example.

The maximum positive peaks 262 and 272 of the differential signal 254 correspond to the maximum positive slope of the negative portion of the non-rectified evoked response signal. The maximum positive slope follows the minimum negative peak of the far field cardiac electrical signal 252. During NSHP capture 280, maximum positive peak 262 has amplitude 264 and occurs at a time interval 260 from the His-Purkinje pacing pulse 256. The maximum peak 272 of the differential signal 254 during VM capture 282 has a lower amplitude 274 and occurs at a longer time interval 270 from the corresponding His-Purkinje pacing pulse 258. One or both of these differences in maximum positive peak amplitudes 264 and 274 and/or maximum positive peak time intervals 260 and 270 of the far field differential signal 254, or a combination thereof, may be used as a metric for determining the type of capture following a His-Purkinje pacing pulse.

In some examples, the ratio of the maximum peak time interval (260 or 270) to the maximum peak amplitude (262 or 272, respectively) is determined as a capture discrimination metric for discriminating between NSHP capture 280 and VM capture 282. The ratio of NSHP capture maximum peak time interval 260 to maximum peak amplitude 264 is less than the ratio of the relatively longer VM maximum peak time interval 270 to relatively lower maximum peak amplitude 274. The maximum peak time interval 270 to amplitude 274 ratio is larger during VM capture 282 compared to NSHP capture 280 due to the delayed, lower amplitude maximum peak 272 following His-Purkinje pacing pulse 258, which fails to capture the His bundle. A higher maximum peak time to amplitude ratio is an indication of VM capture and a relatively low maximum peak time to peak amplitude ratio is an indication of capture of the His bundle, which may be NSHP capture.

The relatively shorter maximum peak time 260 may indicate improved conduction and pacing effectiveness associated with capture of the His-Purkinje system during NSHP capture 280. The combination of the two features of maximum peak time and maximum peak amplitude in a ratio of peak time to peak amplitude provides a metric derived from the negative portion of the evoked response signal in the far field cardiac electrical signal 252 that is a reliable discriminator between NSHP and VM capture. Examples presented herein describe techniques for generating a differential signal from the far field cardiac electrical signal for determining the maximum peak amplitude of the positive slope of the far field cardiac electrical signal and the maximum peak time interval to the maximum peak amplitude from the His-Purkinje pacing pulse. It is recognized that alternative techniques may be used for determining the maximum positive slope of the far field cardiac electrical signal and the corresponding time interval from the pacing pulse to the maximum positive slope for use in determining capture type and discriminating between VM and NSHP capture.

Figure 7:
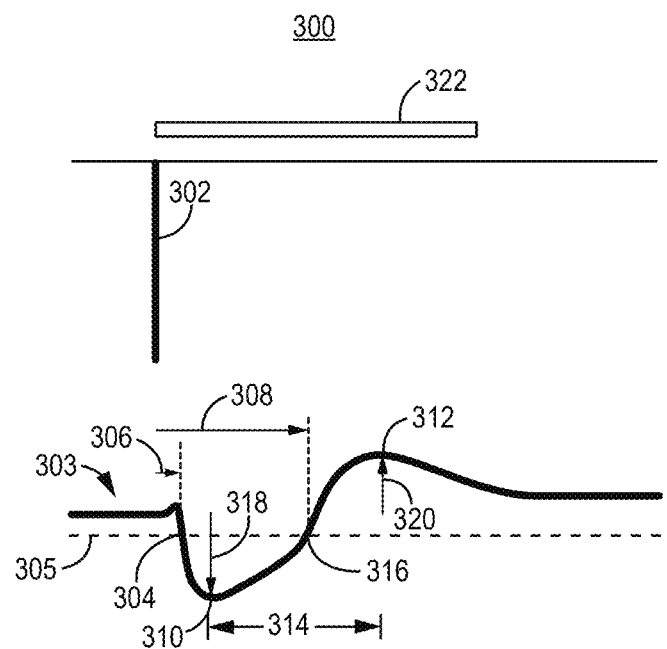
FIG. 7 is a diagram of a His bundle pacing pulse and the resulting far field cardiac electrical signal that may be produced by the medical device of FIG. 3.

FIG. 7 is a diagram 300 of pacing pulse 302 and resulting far field cardiac electrical signal 303 produced by sensing circuit 86. The far field cardiac electrical signal 303 is a non-rectified signal, e.g., EGM signal 168, received by control circuit 80 for determining signal features for discriminating between types of capture following a His-Purkinje system pacing pulse 302. A raw far field signal may be received by sensing circuit 86 via tip electrode 32 and housing 15, for example (see FIG. 1A or 1B), for producing far field cardiac electrical signal 303. The far-field cardiac electrical signal 303 is therefore produced from a raw cardiac electrical signal received using a His-Purkinje pacing electrode or another electrode if available at or near the pacing site such that the evoked response signal following pacing pulse 302 has a negative polarity due to the evoked depolarization traveling away from the electrode used to sense the raw far field signal.

Various features that may be determined by control circuit 80 include time intervals from the His-Purkinje pacing pulse 302 to a fiducial point of the far field cardiac electrical signal 303, amplitudes of fiducial points of the far field cardiac electrical signal 303 and/or slopes of the far field cardiac electrical signal 303. In the example shown, a first time interval 306 from the His-Purkinje pacing pulse 302 to a negative-going threshold crossing 304 and a second time interval 308 from His-Purkinje pacing pulse 302 to a positive going threshold crossing 316 may be determined. The threshold 305 may be a negative threshold value, e.g., $-0.8$ millivolts, to detect the start time 306 and the end time 308 of the negative depolarization portion of the evoked response signal. A third time interval 314 may be determined between the minimum negative peak 310 and the maximum positive peak 312. Time interval 314 is referred to herein as the "peak-to-peak time interval." Control circuit 80 may determine amplitude 318 of minimum peak 310 and amplitude 320 of maximum peak 312. As described above in conjunction with FIG. 5, the post peak slope may be determined as the maximum negative slope following maximum positive peak 312 and used as a capture discrimination feature.

Control circuit 80 may determine various features from the far field cardiac electrical signal 303 over a capture detection window 322 that is started upon delivery of His-Purkinje pacing pulse 302 and extends a predetermined time interval after pacing pulse 302, e.g., 220 ms. In some examples, each sample point of the far field cardiac electrical signal 303 is adjusted to account for baseline offset that may be caused by pacing pulse delivery. For example, the starting amplitude of far field cardiac electrical signal 303 at the onset of window 322, at the time of pacing pulse 302 delivery or just after, may be adjusted to zero millivolts to remove any voltage offset caused by pacing pulse delivery. Each subsequent sample point of far field cardiac electrical signal 303 during window 322 may be adjusted by the voltage offset. Control circuit 80 may perform this offset voltage adjustment to correct for a baseline shift prior to determining the far field signal features shown in FIG. 7.

Figure 8:
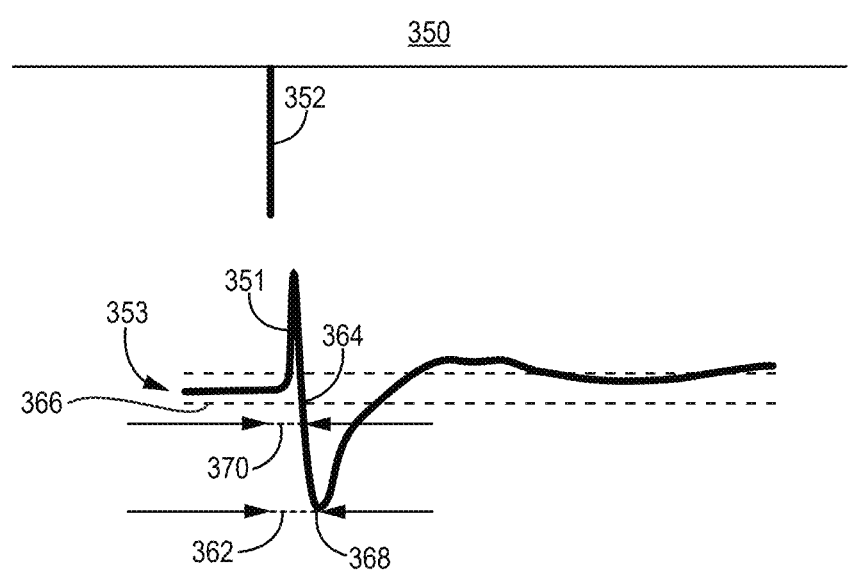
FIG. 8 is a diagram of a pacing pulse and subsequent near field His-Purkinje signal that may be produced by the medical device of FIG. 3.

FIG. 8 is a diagram 350 of a pacing pulse 352 and subsequent near field His-Purkinje signal 353, e.g., produced from a raw cardiac electrical signal acquired using His pacing tip electrode 32 and ring electrode 34 as shown in FIG. 1A or 1B. Control circuit 80 may determine various features of the near field His-Purkinje signal 353, also referred to herein as "near field cardiac electrical signal," for discriminating between capture types during His-Purkinje pacing. Among the features determined from the near field His-Purkinje signal 353 by control circuit 80 are time interval 362 from the His-Purkinje pacing pulse 352 to the absolute maximum peak 368 and time interval 370 from the His-Purkinje pacing pulse 354 to a threshold crossing 364 (which is negative in this example but may be positive in other examples). Threshold 366 may be set to a predefined value, e.g., −0.8 millivolts, and the time interval 370 may represent the "isoelectric distance" or time from the His-Purkinje pacing pulse until an electrical response to the pacing pulse is detected. The time intervals 362 and 370 may be used in verifying capture and discriminating between capture types. The early, narrow deflection 351, which may be positive or negative in various examples, is pacing artifact caused by delivery of pulse 352 and is ignored for the purposes of determining signal features, detecting capture and discriminating capture type.

As described below, a crossing 364 of threshold 366 by near field His-Purkinje signal 353 during a capture detection window 322 (shown in FIG. 7) may be used to confirm that loss of capture has not occurred in some examples. In response to threshold crossing 364, control circuit 80 may analyze the far field cardiac electrical signal, the near field His-Purkinje signal and/or the differential signal generated from the far field cardiac electrical signal for determining whether SHP, NSHP or VM capture has occurred in response to the His-Purkinje pacing pulse 352. For instance, the time intervals 370 and 362 may be compared to respective thresholds or ranges for verifying that the evoked response occurs within an expected time from pacing pulse 352 indicative of a particular capture type.

Figure 9:
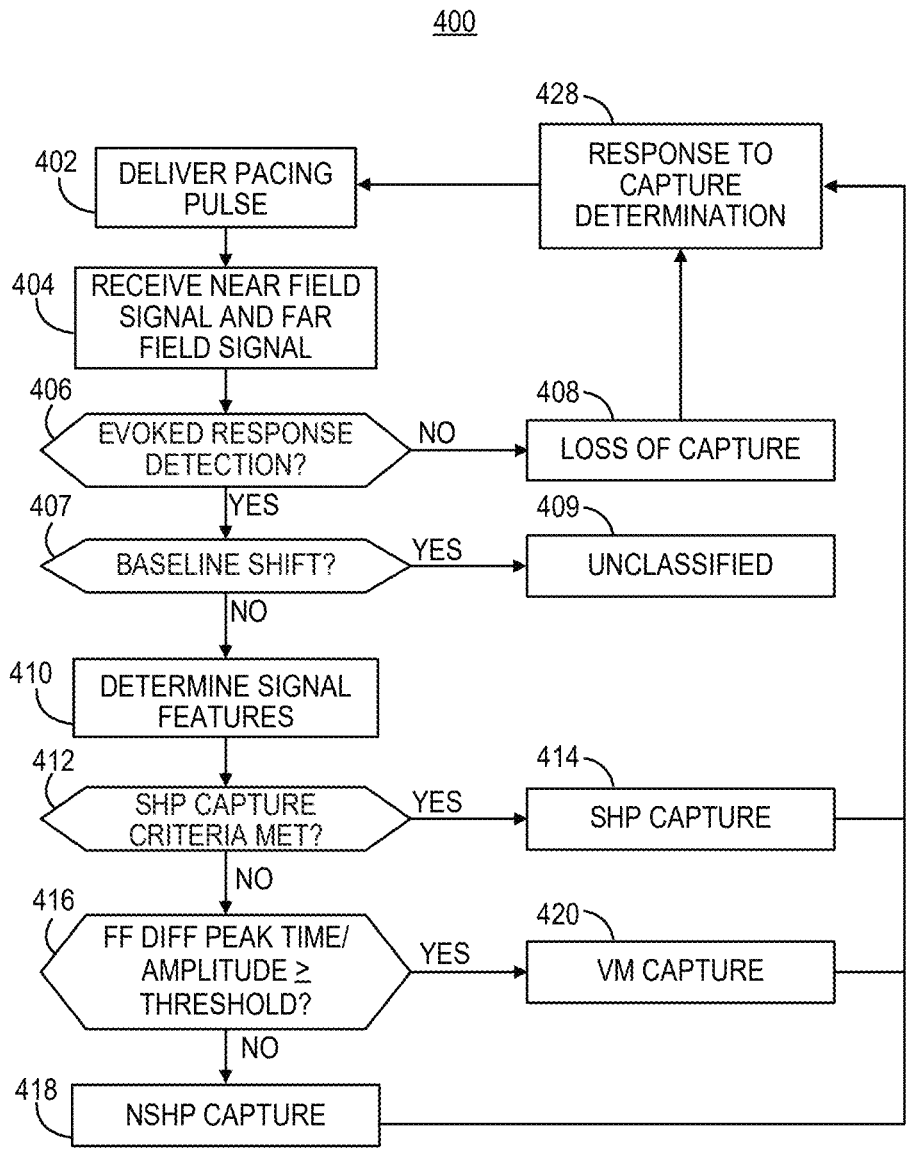
FIG. 9 is a flow chart of a method performed by a medical device for detecting capture during His-Purkinje system pacing according to one example.

FIG. 9 is a flow chart 400 of a method performed by a medical device, e.g., IMD 14 of FIG. 1A or 1B or pacemaker 100 of FIG. 2, for detecting capture during His-Purkinje system pacing according to one example. At block 402, a His-Purkinje pacing pulse is delivered. The His-Purkinje pacing pulse may be delivered as part of a capture threshold test. In this case, the pacing pulse delivered at block 402 may be one of a series of His-Purkinje pacing pulses delivered at different pacing pulse energies, e.g., by varying pulse amplitude. At other times, the His-Purkinje pacing pulse delivered at block 402 may be delivered as part of a ventricular pacing therapy, e.g., bradycardia pacing, atrial synchronized ventricular pacing, cardiac resynchronization therapy (CRT) or other pacing therapy. In this case, the process of flow chart 400 may be performed by the medical device for verifying capture of the His-Purkinje pacing pulse for managing and maintaining capture during the pacing therapy.

At block 404, control circuit 80 receives the near field His-Purkinje signal and the far field cardiac electrical signal from sensing circuit 86. Control circuit 80 may determine if an evoked response is detected at block 406. In some examples, sensing circuit 86 includes evoked response detection circuitry 180 (shown in FIG. 4) that produces an evoked response detect signal 188 passed to control circuit 80. In other examples, control circuit 80 may set a capture detection window, e.g., window 322 shown in FIG. 7, and detect an evoked response based on the amplitude of a received near field or far field EGM signal crossing the evoked response detection threshold during the capture detection window.

If the delivered energy of the pacing pulse is less than both the His-Purkinje system and the ventricular myocardial capture thresholds, no evoked response signal will be present during the capture detection window. For example, the amplitude of the near field or far field cardiac electrical signal will not cross the evoked response detection threshold indicating a relatively low amplitude baseline signal. The evoked response detection threshold crossing is used to discriminate loss of capture from capture, which may be any type of capture (e.g., SHP capture, NSHP capture or VM capture). As such, the evoked response threshold applied by control circuit 80 to an EGM signal may be set to a relatively small value, e.g., −0.8 millivolts, to detect the onset of the negative depolarization portion of an evoked response waveform. The evoked response detection threshold may be set higher or lower than the example of −0.8 millivolts, e.g., between −0.2 millivolts and −2.0 millivolts, and may be based on the evoked response signal strength and baseline noise in a given patient. The capture detection window may be 180 to 250 ms in duration, e.g., 220 ms, following the His-Purkinje pacing pulse.

If an evoked response is not detected ("no" branch of block 406), control circuit 80 detects loss of capture at block 408. In response to detecting the evoked response based on an EGM signal threshold crossing or receiving an evoked response detect signal from sensing circuit 86, control circuit 80 determines that capture has occurred and advances to block 410 for discriminating between capture types through analysis of the near field and far field cardiac electrical signals received from sensing circuit 86. When an evoked response is detected ("yes" branch of block 406), control circuit 80 may first check the near field and far field cardiac electrical signals received from sensing circuit 86 for baseline shift at block 407. A shift in the baseline of the near field or far field cardiac electrical signal may be caused by baseline drift or pacing artifact due to delivery of the His-Purkinje pacing pulse. Control circuit 80 may detect a baseline shift at block 407 based on a comparison of at least one signal sample point to a baseline amplitude range. For example, if a single sample point from the EGM signal corresponding in time to delivery of the His-Purkinje pacing pulse is outside the range of ±0.8 millivolts, baseline shift is detected at block 407. The paced beat may be determined as "unclassified" at block 409. The detected evoked response may be caused by baseline shift or capture may have occurred but due to excessive baseline shift an analysis of evoked response signal features may be unreliable in determining the capture type. As such, the paced beat may be defined as unclassified at block 409 without performing additional cardiac electrical signal analysis.

When baseline shift is not detected at block 407, control circuit 80 advances to block 410 to determine near field signal and/or far field signal features for determining the detected capture type. Examples of features that may be determined at block 410 include any of those described above in conjunction with FIGS. 5 through 8. At block 412, control circuit 80 determines if criteria for detecting SHP capture are satisfied. Example techniques and criteria for detecting SHP capture are described below in conjunction with FIG. 12.

In one example, at least a post-peak slope is determined from the far field cardiac electrical signal at block 410. As shown and described in conjunction with FIG. 5, SHP capture may be distinguished from NSHP capture based on a relatively high post-peak slope following the maximum positive peak of the far field cardiac electrical signal. As such, control circuit 80 may at least detect the maximum positive peak of the far field signal at block 410 and determine a negative slope following the maximum positive peak as the post-peak slope, e.g., using any of the methods described in conjunction with FIG. 5. The determined post-peak slope may be compared to a slope threshold at block 412. If the (absolute) magnitude of the slope is greater than the slope threshold, indicating a relatively high slope ("yes" branch of block 412), SHP capture is detected at block 414. The slope threshold may be set to 1 millivolt in one example and the post-peak slope is required to be a negative slope. The slope may be determined as a voltage difference since the time interval between sample points is fixed for a given sampling rate. Consequently, the slope threshold may be defined in millivolts. Other criteria that may be applied at block 412 for detecting SHP capture are described in conjunction with FIG. 12 below.

When SHP capture detection criteria are not met ("no" branch of block 412), the capture type may be NSHP capture or VM capture. In order to discriminate between NSHP and VM capture, control circuit 80 may generate a far field differential signal from the far field cardiac electrical signal. Control circuit 80 determines one or both of the maximum positive peak amplitude of the far field differential signal and/or the maximum peak time interval from the His-Purkinje pacing pulse to the maximum positive peak amplitude of the far field differential signal. As described in conjunction with FIG. 6, control circuit 80 may determine the ratio of the maximum peak time interval to peak amplitude as a metric for discriminating between capture types. These features may be determined at block 410 or at block 416 in response to not detecting SHP capture at block 412. At least one of the peak amplitude, the peak time interval and/or the ratio of the peak time interval to the peak amplitude is/are compared to a respective threshold at block 416. When an evoked response is detected at block 406 and SHP capture is not identified based on SHP capture detection criteria being unmet, control circuit 80 may analyze the maximum peak time interval to peak amplitude ratio of the far field differential signal to discriminate between NSHP capture and VM capture (loss of His-Purkinje capture).

If the maximum peak amplitude is less than a respective threshold, the maximum peak time interval is greater than a respective threshold, and/or the peak time to peak amplitude ratio is greater than a ratio threshold, VM capture is indicated. In some examples, NSHP capture is detected at block 418 in response to the maximum peak time to peak amplitude ratio (FF DIFF PEAK TIME/AMPLITUDE) being less than or equal to a threshold ratio. If the ratio is greater than the ratio threshold, VM capture is detected at block 420. The ratio threshold may be set to a fixed ratio threshold or set based on a previously determined maximum peak time interval to amplitude ratio. A change in the ratio from a previously determined ratio indicates a change in capture type. As described below in conjunction with FIG. 10, a reference ratio may be determined during a known capture type and the ratio threshold may be set based on the reference ratio.

It is contemplated that other capture detection criteria may be applied at block 416 in addition to the maximum peak time interval to amplitude ratio threshold for detecting either VM capture or NSHP capture. For example, threshold criteria may be applied to any of the near field His-Purkinje signal features and/or far field signal features described above in conjunction with FIGS. 6 and 7. Such features may include features determined from the far field cardiac electrical signal such as the minimum peak amplitude 318, maximum peak amplitude 320, the peak-to-peak time interval 314 between the minimum peak 310 and maximum peak 312, negative depolarization start time determined as the time interval 306 from the His-Purkinje pacing pulse to a negative-going threshold crossing 304, negative depolarization end time determined as time interval 308 from the His-Purkinje pacing pulse to a positive going threshold crossing 316 of the negative portion of the evoked response signal, negative depolarization width between the negative-going threshold crossing 304 and positive-going threshold crossing 316 (all shown in FIG. 7) or any combination thereof. Features used to discriminate capture type may additionally or alternatively include features determined from the near field His-Purkinje signal such as the time interval 370 from the His-Purkinje pacing pulse to a negative going threshold crossing 364 and/or the time interval 362 from the His-Purkinje pacing pulse to a peak 368 as shown in FIG. 8. Methods for determining capture type, which include additional criteria based on time interval and/or amplitude features of the far field cardiac electrical signal and/or the near field His-Purkinje signal are described below in conjunction with FIGS. 11 and 12.

At block 428, control circuit 80 may perform a response to the determined capture type which may include storing the results of the capture determination in memory 82 and/or adjusting the His-Purkinje pacing pulse energy. When the method of flow chart 400 is being performed as part of a capture threshold test, control circuit 80 may store the capture type as being one of SHP, NSHP, VM or loss of capture, with the corresponding pacing pulse voltage amplitude (and/or width). Control circuit 80 may adjust the pacing pulse amplitude (and/or width) to a next test setting at block 428 and repeat the process of determining the capture type. This process may be repeated until at least one or all of the SHP capture threshold, NSHP capture threshold, and/or VM capture threshold is/are identified. Each capture threshold type may be identified as the lowest pacing pulse output setting, e.g., lowest pacing pulse amplitude for a given pulse width, at which the given type of capture is detected. Control circuit 80 may automatically set the pacing pulse amplitude (and/or width) to a safety margin above the determined capture threshold that includes capture of the His bundle, e.g., above the NSHP capture threshold or above the SHP capture threshold, to promote a high likelihood of capturing the His-Purkinje during a pacing therapy. In some examples, control circuit 80 reports the determined capture threshold(s) by storing the capture threshold data in memory 82 for transmission to external device 50 via telemetry circuit 88.

When the method of flow chart 400 is being performed for capture management during pacing therapy delivery, control circuit 80 may increase the pacing pulse amplitude (or width) at block 428 in response to detecting loss of capture (block 408) or in response to detecting VM capture (block 420) in order to increase the likelihood of capturing the His bundle. The loss of capture detections and/or VM capture detections and corresponding delivered pacing pulse energy may be logged in memory 82 at block 428 for use in identifying and tracking pacing capture thresholds and for determining the percentage of time that the patient is receiving effective His-Purkinje pacing therapy delivery.

In some examples, detection of NSHP capture or SHP capture may also trigger an adjustment of the pacing pulse energy when SHP or NSHP capture is preferred over the detected capture type. For example, if SHP capture is detected at block 414, control circuit 80 may increase the pacing pulse energy to achieve NSHP capture in order to achieve capture of both the His-Purkinje system and ventricular myocardial tissue to reduce the likelihood of total loss of ventricular capture. When NSHP capture is detected and SHP capture threshold is greater than the VM capture threshold, the pulse energy may be decreased at block 428 to achieve SHP capture without myocardial capture and to conserve power source 98.

In other examples, control circuit 80 may initiate a capture threshold test at block 428 in response to detection of loss of capture, detection of VM capture, or detection of one of SHP capture or NSHP capture when the other of NSHP or SHP capture is the preferred capture type. In these situations, control circuit 80 may be performing the method of FIG. 9 for capture monitoring during delivery of a pacing therapy and when the capture type is not the expected capture type, a capture threshold test may be performed by adjusting the pacing pulse energy to multiple pulse energy settings (e.g., multiple voltage amplitudes and/or pulse widths) to determine the capture threshold for one or more of SHP, NSHP and/or VM capture.

Figure 10:
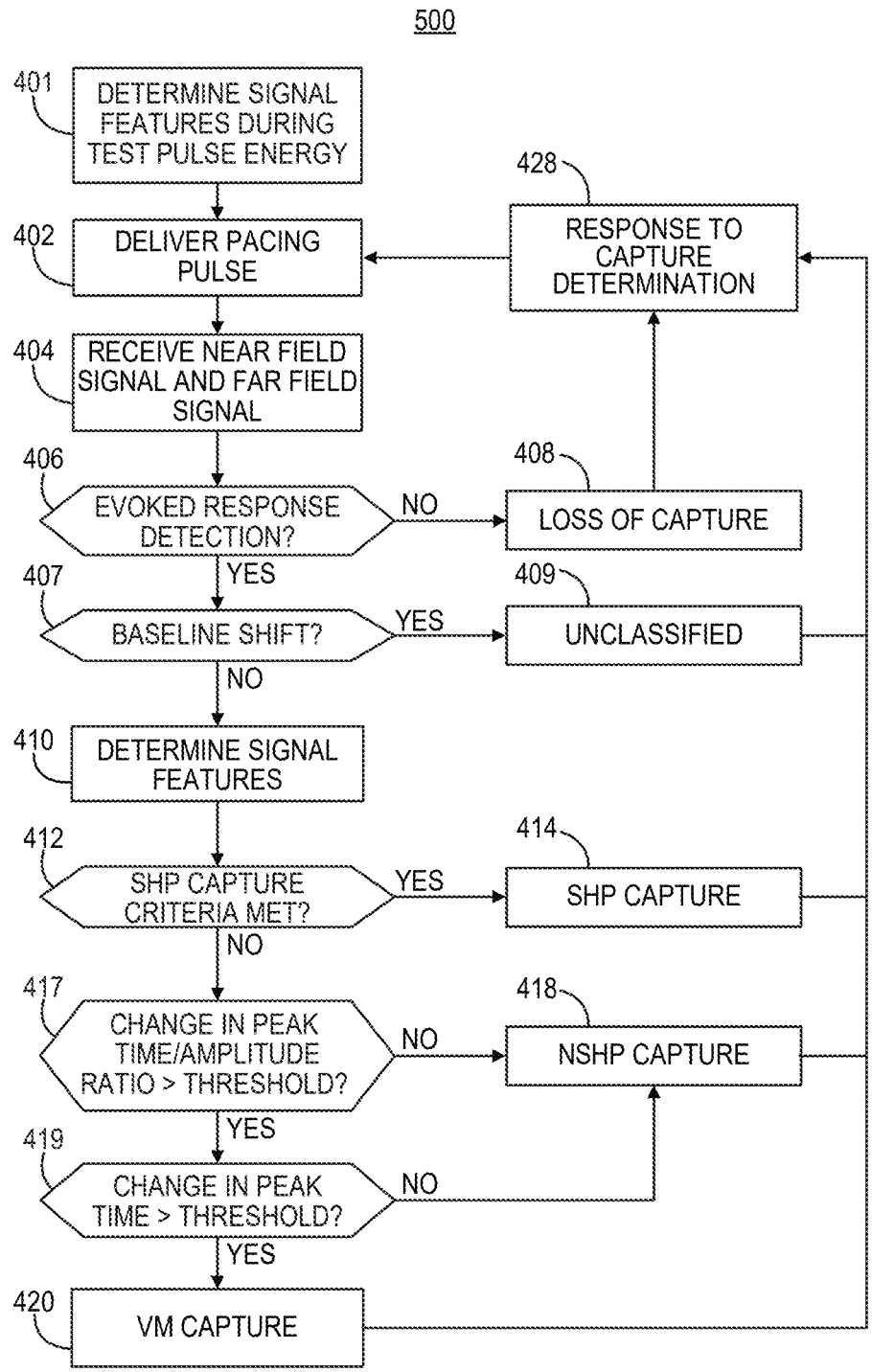
FIG. 10 is a flow chart of a method for determining capture type following delivery of a pacing pulse according to another example.

FIG. 10 is a flow chart 500 of a method for determining capture type following delivery of a pacing pulse according to another example. Identically numbered blocks in FIG. 10 correspond to like-numbered blocks in FIG. 9. In the process of flow chart 500, control circuit 80 establishes reference values of cardiac signal features during a known capture condition. For example, control circuit 80 may control therapy delivery circuit 84 to deliver a His-Purkinje pacing pulse at a test pulse energy at block 401 to establish reference values of cardiac electrical signal features. The test pulse energy may be selected to be a maximum test amplitude and pulse width setting, which may be equal to or less than the maximum available pacing pulse output settings of the medical device. In one example, the test pulse amplitude is set to 5 volts and the test pulse width is set to 0.5 to 1 millisecond pulse width.

This relatively high test pulse energy is expected to produce NSHP capture and therefore may be used to establish reference cardiac signal features for discriminating between SHP and NSHP capture and between VM and NSHP capture. In the case where NSHP capture is not achieved at the test pulse energy, the user may be able to program the type of capture observed at the test pulse energy or adjust the test pulse energy until NSHP capture is observed based on ECG or EGM signals. In other examples, the His-Purkinje pacing pulse amplitude and pulse width test setting used at block 401 may be selected to cause known VM capture or known SHP capture for use in establishing reference cardiac signal feature values corresponding to the respective capture type.

In the example of FIG. 10, at block 401, cardiac signal features are determined during the test pulse energy setting, which is expected to result in NSHP capture. As such, signal features determined at block 401 following one or more pacing pulses delivered at the test pulse energy are used to establish thresholds for discriminating NSHP capture from other types of capture. In one example, control circuit 80 generates the far field differential signal and determines the maximum positive peak amplitude and/or the time interval from the His-Purkinje pacing pulse to the maximum positive peak of the differential signal. In some examples, both the peak amplitude and peak time interval are determined, e.g., as described in conjunction with FIG. 6, so that control circuit 80 can determine and store the peak time to peak amplitude ratio in memory 82 as a reference ratio value for detecting capture that includes capture of the His bundle. This reference ratio value may be used for setting a threshold ratio for discriminating between NSHP and VM capture, e.g., after SHP capture is not detected based on other cardiac signal feature criteria.

At block 402, therapy delivery circuit 84 adjusts the pacing pulse energy to deliver a His-Purkinje pacing pulse according to a capture threshold test or according to a pacing therapy being delivered. The near field His-Purkinje signal and far field cardiac electrical signal are produced by sensing circuit 86 and received by control circuit 80 at block 404. If an evoked response is detected by the evoked response detection circuit or based on a capture detection threshold crossing by the near field or far field cardiac electrical signals ("yes" branch of block 406), but the criteria for detecting SHP capture are not met ("no" branch of block 412), control circuit 80 may analyze the differential signal generated from the far field EGM signal at block 417. In some examples, the maximum peak time to peak amplitude ratio determined from the far field differential signal is determined at block 417. This ratio is compared to the reference ratio value determined at block 401 during a test His pacing pulse energy setting. When the ratio increases by a threshold amount, VM capture with a loss of His-Purkinje capture is indicated. In some examples, a change in the peak time to amplitude ratio indicating VM capture may be detected at block 417 in response to an increase of at least 20%, 30%, 50% or other predetermined percentage greater than the reference ratio value established at block 401. In response to a threshold increase in the maximum peak time to peak amplitude ratio, VM capture may be detected at block 420. When the change in this ratio is less than a threshold amount ("no" branch of block 417), NSHP capture is detected at block 418.

In some examples, additional criteria may be applied for discriminating between VM and NSHP capture. In the example of flow chart 500, at block 419 control circuit 80 compares the maximum positive peak time interval (from the His-Purkinje pacing pulse to the maximum positive peak of the far field differential signal) to the reference value established at block 401. Both the maximum peak time to peak amplitude ratio at block 417 and the maximum peak time at block 419 may be required to be increased by at least a threshold amount compared to the respective reference values established for a test pulse energy at block 401 in order to detect VM capture at block 420. Otherwise, NSHP capture is detected at block 418. As described above in conjunction with FIG. 9, control circuit 80 may perform an appropriate response to the determined capture type at block 428.

Figure 11:
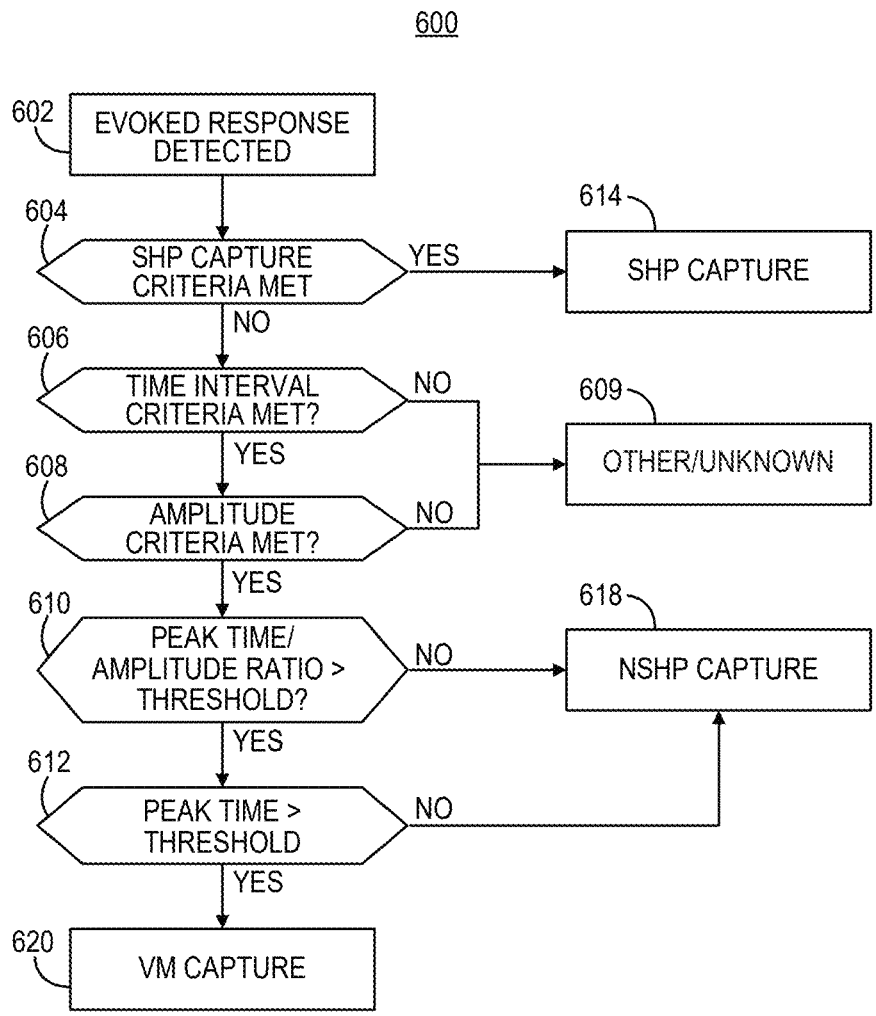
FIG. 11 is a flow chart of a method for detecting pacing capture type according to yet another example.

FIG. 11 is a flow chart 600 of a method for detecting pacing capture type according to another example. In response to detecting an evoked response signal following a His-Purkinje pacing pulse at block 602, control circuit 80 may determine if SHP capture detection criteria are met at block 604. It is recognized that in some examples, detecting an evoked response may be optional. SHP capture detection criteria may be applied to the near field His-Purkinje signal and/or far field cardiac electrical signal following a His-Purkinje pacing pulse at block 604. Example techniques for detecting SHP capture have been described above and are described below in conjunction with FIG. 12. When SHP capture detection criteria are unmet, control circuit 80 may determine whether time interval criteria for detecting capture that includes VM capture are met at block 606. Capture of myocardial tissue, with or without capture of the His bundle, is expected to produce a relatively early and wide evoked response signal. Accordingly, time interval features determined from the far field cardiac electrical signal, the near field cardiac electrical signal, and/or the differential signal generated from the far field cardiac electrical signal may be compared to threshold values at block 606 to determine that the time interval from the His-Purkinje pacing pulse to one or more signal features corresponds to an early and wide negative portion of the evoked response signal.

In one example, the time interval criteria applied at block 606 requires that one or more of the negative depolarization start time of the far field cardiac electrical signal, the negative depolarization end time of the far field cardiac electrical signal, and/or the peak-to-peak time interval of the far field cardiac electrical signal (e.g., from the negative minimum peak to the maximum positive peak) meet respective time interval thresholds. As described in conjunction with FIG. 7, the negative depolarization start time of the far field cardiac electrical signal may be determined as the time interval from the His-Purkinje pacing pulse to a negative-going, negative threshold crossing of the non-rectified evoked response signal. The negative depolarization end time of the far field cardiac electrical signal may be determined as the time interval from the His-Purkinje pacing pulse to a positive-going, negative threshold crossing of the non-rectified evoked response signal. The peak-to-peak time interval of the far field cardiac electrical signal may be the time interval from the negative, minimum peak to the maximum positive peak. These time intervals are polarity dependent in that the fiducial evoked response features or sample points defining the start time, end time and peak-to-peak time interval are each determined using a fiducial point of the negative polarity portion of the evoked response signal in the far field cardiac electrical signal.

The threshold criteria applied to each of the time intervals determined at block 606 are selected to differentiate between capture types and/or verify a physiological evoked response signal as opposed to non-cardiac noise or other artifact. In one example, the negative depolarization start time threshold is in the range of 80 ms to 100 ms, e.g., less than or equal to 94 ms. The negative depolarization end time threshold is in the range of 140 ms to 160 ms, e.g., less than or equal to 148 ms. The peak-to-peak time interval threshold may be defined as a range of at least 30 ms and not greater than 150 ms. A negative depolarization portion of the evoked response signal starting later or ending later than the respective threshold may be an indication of capture that does not include ventricular myocardial capture since the evoked depolarization of surrounding myocardial cells is not delayed due to conduction along the native conduction system. An evoked response signal having a peak-to-peak time interval that is greater than or less than the threshold range may be an indication of a fusion beat, possible far-field atrial P-wave oversensing or another event that is not an evoked response due to NSHP capture or VM capture. The time interval criteria applied at block 606 may additionally or alternatively require that the maximum positive peak time of the differential far field cardiac electrical signal be within a threshold range, e.g., at least 50 ms but not greater than 160 ms. The near field evoked response onset time may be required to be within a physiological capture window, e.g., within 80 ms of the His-Purkinje pacing pulse. An evoked response signal having an onset time in the near field His-Purkinje signal that is earlier than the threshold range may be noise, artifact, a fusion beat, a conducted atrial beat, an oversensed P-wave or another event that is not an NSHP or VM capture event. An evoked response signal having an onset time in the near field signal that is later than the threshold range may be indicative of atrial capture or other event that is not due to His-Purkinje or ventricular myocardial capture at the pacing site. When time interval criteria are unmet at block 606, control circuit 80 may identify the capture signal as an unknown or "other" capture type at block 609.

At block 608, amplitude criteria may be applied to the evoked response signal in the near field His-Purkinje signal, the far field cardiac electrical signal, and/or to the differential far field cardiac electrical signal. The amplitude criteria may be applied during the capture detection window. In some examples, the amplitude criteria may be included to eliminate signals that are not within a normal physiological range of an evoked response signal. In one example, the minimum peak amplitude 318 (see FIG. 7) of the far field cardiac electrical signal may be required to be greater than an amplitude threshold, e.g., greater than −7 millivolts. A minimum peak that is less than the amplitude threshold may be indicative of non-cardiac or non-physiologic artifact or other capture type, such as fusion of an evoked response and an intrinsic depolarization wavefront.

All or any combination of the time interval and amplitude criteria examples given above may be required to be satisfied in order to detect either NSHP or VM capture after SHP capture criteria are not met. If either of the time interval criteria and/or the amplitude criteria are not met, control circuit 80 may classify the detected capture as being an "other" capture type or unknown event at block 609.

When time interval and amplitude criteria are met, control circuit 80 may determine the peak time to peak amplitude ratio of the far field differential signal within the capture detection window. The peak time to peak amplitude ratio may be determined as described above in conjunction with FIG. 6. The peak time to peak amplitude ratio may be compared to a threshold value by control circuit 80 at block 610. The threshold value may be based on a reference ratio determined during His-Purkinje system pacing at a test pulse output setting for a known capture type. As described above in conjunction with FIG. 10, the reference ratio may be determined at a relatively high pacing pulse amplitude expected or confirmed to result in NSHP capture. If the peak time to peak amplitude ratio is not greater than a reference ratio or threshold based thereon, NSHP capture is detected at block 618. In addition to the ratio not increasing significantly from the reference ratio, control circuit 80 may compare the peak time interval of the far field differential signal (e.g., peak time interval 260 or 270 in FIG. 6) to the reference peak time interval or a threshold based thereon, determined during the test His-Purkinje pacing pulse output setting expected or confirmed to cause NSHP capture. If the peak time interval of the far field differential signal is not greater than the reference time interval or a threshold based thereon at block 612, NSHP capture may be detected at block 618. Otherwise, the capture type is identified by control circuit 80 as VM capture at block 620 in response to the peak time to peak amplitude ratio, and optionally the peak time interval, being greater than the respective reference ratio and reference peak time interval. As described above in conjunction with FIG. 9, block 428, control circuit 80 may perform a response to the determined capture type.

In the example of FIG. 10, SHP capture criteria are applied after detecting an evoked response and, when SHP capture criteria are not met, criteria for discriminating VM and NSHP capture are applied. It is contemplated, however, that the criteria relating to the far field differential signal peak time, peak amplitude, and/or peak time to peak amplitude ratio may be applied first to determine if VM capture is detected. If a change from the reference peak time, peak amplitude, and/or peak time to peak amplitude ratio is detected, control circuit 80 may detect VM capture and suspend any further cardiac electrical signal analysis. If VM is not detected, control circuit 80 may perform additional analysis to discriminate NSHP from SHP capture, e.g., by using the post-peak slope as shown in FIG. 5 and/or other criteria, e.g., as described below in conjunction with FIG. 12.

Figure 12:
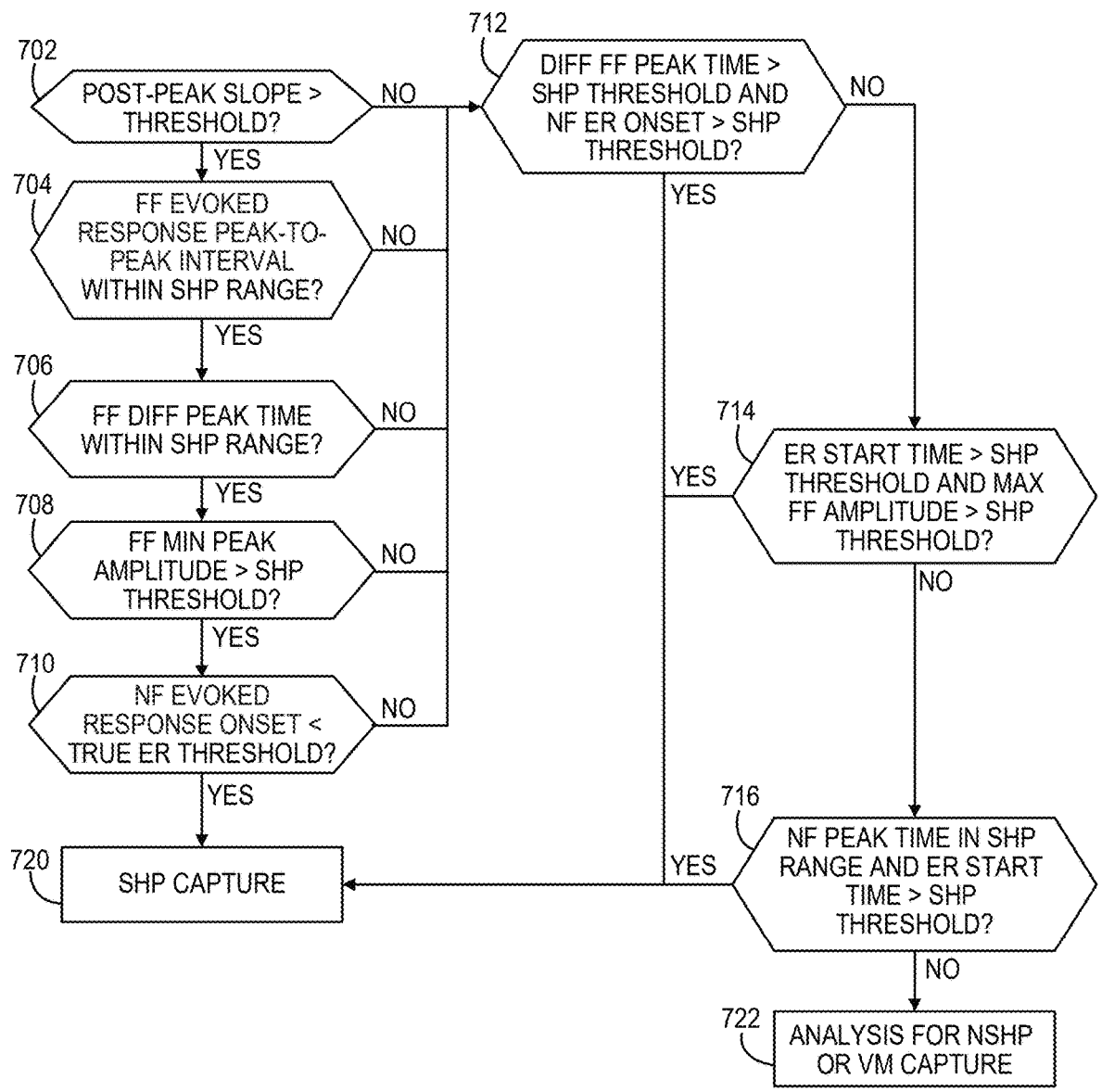
FIG. 12 is a flow chart of a method for detecting selective His-Purkinje system capture according to some examples.

FIG. 12 is a flow chart 700 of a method for detecting SHP capture according to one example. The method of flow chart 700 may be performed by control circuit 80 at block 412 of FIGS. 9 and 10 or block 604 of FIG. 11 to determine if SHP capture criteria are met. Multiple sets of SHP capture detection criteria may be applied with each set of criteria including one or more time interval requirements and/or one or more amplitude requirements. Each different set of SHP capture detection criteria may correspond to a different characteristic morphology of an evoked response signal that may occur in some patients during SHP. By applying multiple different combinations of SHP capture criteria, SHP capture may be reliably detected even when the evoked response signal morphology during SHP capture can vary between patients, electrode location, etc.

In one example, the post-peak slope of the far field cardiac electrical signal, following the maximum positive peak as shown in FIG. 5, may be compared to a slope threshold by control circuit 80 at block 702. If the absolute value of the maximum negative slope following the maximum positive peak is not greater than a slope threshold, an alternative set of SHP capture detection criteria are applied at block 712. If the post-peak slope meets the SHP threshold requirement at block 702, as described in conjunction with FIG. 5, additional time interval based and/or amplitude based criteria may be applied to detect one type of characteristic evoked response signal during SHP capture at blocks 704 through 710.

At block 704, the peak-to-peak time interval of the far field cardiac electrical signal (e.g., shown as time interval 314 in FIG. 7) is compared to a SHP threshold range. The peak-to-peak time interval is expected to be relatively narrow but wider than an artifact or noise spike that may be present in the far field signal. The maximum positive peak of the evoked response signal may occur earlier or later than the minimum negative peak of the evoked response signal depending on various factors. When the peak-to-peak time interval is defined as the time of the maximum positive peak to the time of the minimum negative peak, the difference is negative when the positive peak occurs earlier than the negative peak. The peak-to-peak time interval for SHP capture detection may therefore have a negative value. The peak-to-peak time interval may always be positive, however, during NSHP and RV capture. Accordingly, a threshold peak-to-peak time interval for SHP capture detection may be between −50 ms and +65 ms in one example. The peak-to-peak time interval in this case is determined as the time from the pacing pulse to the positive maximum peak minus the time from the pacing pulse to the negative minimum peak. If the peak-to-peak time interval of the far field cardiac electrical signal does not fall within the SHP capture detection threshold range, a different set of SHP capture detection criteria may be applied at block 712.

At block 706, the maximum positive peak time interval of the far field differential signal is compared to a SHP capture detection range by control circuit 80. The interval from the pacing pulse to the maximum peak of the far field differential signal may be outside the SHP capture detection range when myocardial capture is occurring, resulting in a longer peak time interval, or when another type of capture or noise is present in the far field cardiac electrical signal. The SHP capture detection threshold range applied to the peak time interval of the far field differential signal may be from 80 ms to 200 ms in one example.

When the far field differential signal peak time interval is within the SHP capture detection range ("yes" branch of block 706), control circuit 80 may compare the minimum peak amplitude of the far field cardiac electrical signal to a SHP capture detection threshold at block 708. The amplitude threshold for detecting SHP may be at least −7 millivolts in one example. This amplitude criterion may be applied to verify that that minimum peak is within a physiological range for an evoked response signal as opposed to other non-cardiac or non-physiological signal noise or artifact.

When the criteria applied at blocks 702, 704, 706, and 708 are satisfied, control circuit 80 may optionally verify that the time from the His-Purkinje pacing pulse to the onset of the evoked response in the near field EGM signal, e.g., time interval 370 in FIG. 8 which may be referred to as the "isoelectric distance," is within a threshold range, evidencing a true evoked response signal. The time interval to the onset of the evoked response signal in the near field His-Purkinje signal may be required to be greater than a minimum threshold time interval. For instance, the onset time interval may be required to be greater than 100 ms and less than 140 ms, as an example. A shorter time interval from the pacing pulse to the onset of the near field evoked response signal may indicate myocardium is captured and that analysis for NSHP or VM capture should be performed. A longer time interval may indicate that the signal is not a true evoked response signal. When the combination of criteria applied at blocks 702 through 710 are satisfied, SHP is detected by control circuit 80 at block 720 based on this first combination of SHP capture detection criteria.

This first set of criteria represented by blocks 702 through 710 may represent one type of evoked response signal that occurs with SHP. When any one of the criteria of blocks 702 through 710 are unmet, other combinations of criteria may be analyzed by control circuit 80 for still detecting SHP based on other characteristics of the SHP evoked response signals in the far field cardiac electrical signal, the far field differential signal and/or the near field His-Purkinje signal.

For instance, during SHP, the far field differential signal may have a delayed maximum positive peak time. This in combination with a relatively long near field evoked response onset may be adequate evidence for detecting SHP. The set of criteria applied at block 712 require that the positive peak time interval of the far field differential signal be greater than a respective SHP capture detection threshold and the onset of the evoked response signal in the near field His-Purkinje signal be greater than a respective SHP capture detection threshold. If these time intervals are greater than their respective thresholds, SHP capture may be detected by control circuit 80 at block 720. Example thresholds may be a far field differential signal peak time interval of at least 110 ms and the evoked response onset in the near field signal of at least 98 ms. If the peak time interval of the differential signal and the onset of the near field evoked response signal are both less than their respective thresholds, control circuit 80 may apply a third combination of SHP capture detection criteria at block 714.

At block 714, SHP capture may be detected when the evoked response start time 306 (FIG. 7) in the far field cardiac electrical signal is greater than a SHP capture detection threshold time and the maximum positive peak amplitude 320 (FIG. 7) of the far field cardiac electrical signal is greater than a SHP capture detection threshold amplitude. An example threshold for evoked response start time in the far field signal may be 80 ms, and an example amplitude threshold may be at least 1.5 millivolts. These criteria enable control circuit 80 to detect an evoked response signal during SHP capture that is characterized by a delay in the start of the evoked response due to conduction along the native conduction system. The positive peak amplitude of the evoked response signal in the far field signal may be required to be higher than a threshold amplitude to verify that the signal is a true evoked response signal.

If the criteria applied at block 714 are not satisfied, control circuit 80 may determine if an alternative combination of criteria for detecting SHP capture is satisfied at block 716. In this set of criteria, the peak time of the near field His-Purkinje signal (e.g., time interval 362 in FIG. 8) from the pacing pulse to the absolute maximum peak) may be required to be in an SHP time interval range, and the evoked response start time in the far field cardiac electrical signal (e.g., time interval 306 in FIG. 7) may be required to be greater than an SHP time interval threshold. For example, the near field peak time may be required to be in the range of at least 78 ms to less than 140 ms, and the evoked response start time in the far field signal may be required to be at least 40 ms in order to detect SHP capture.

When at least one of the combinations of SHP detection criteria applied at blocks 702 through 710, block 712, block 714 or block 716 is determined to be satisfied by control circuit 80, SHP capture is detected by control circuit 80 at block 720. Control circuit 80 may perform a response to the SHP capture determination as described above in conjunction with block 428 of FIG. 9. If none of the combinations of criteria applied for detecting SHP capture are satisfied, control circuit 80 advances to block 722 to perform additional analysis of the far field cardiac electrical signal, far field differential signal and/or near field His-Purkinje signal as described above in conjunction with FIG. 9, 10 or 11 for determining a different capture type.

Specific sets or combinations of example criteria are described in conjunction with FIG. 12 for detecting SHP capture when any one set or combination of criteria is satisfied. While specific examples are given, these examples are illustrative in nature. The near field and far field evoked response signals during SHP capture detection may present differently in different patients. By including multiple combinations of criteria for SHP capture detection, SHP capture may be detected when any one combination of criteria is satisfied. Within each combination of criteria, multiple criterion may each be required to be satisfied (e.g., according to a logical "AND"), but only one set or combination of criteria (e.g., according to a logical OR) out of the multiple combinations of criteria may be required to be satisfied to detect SHP capture. This is represented by the flow chart 700 of FIG. 12 where each requirement within a set of criteria, e.g., blocks 702 through 710, are all required to be satisfied for SHP capture to be detected, but, if not, one of the alternative sets of criteria (block 712 or block 714 or block 716) may be satisfied and lead to SHP capture detection. In this way, different combinations of near field, far field and/or far field differential signal features may define multiple combinations of criteria that indicate SHP capture to increase the sensitivity and specificity of SHP capture detection when variation in evoked response waveform morphology exists between patients and/or over time.

Figure 13:
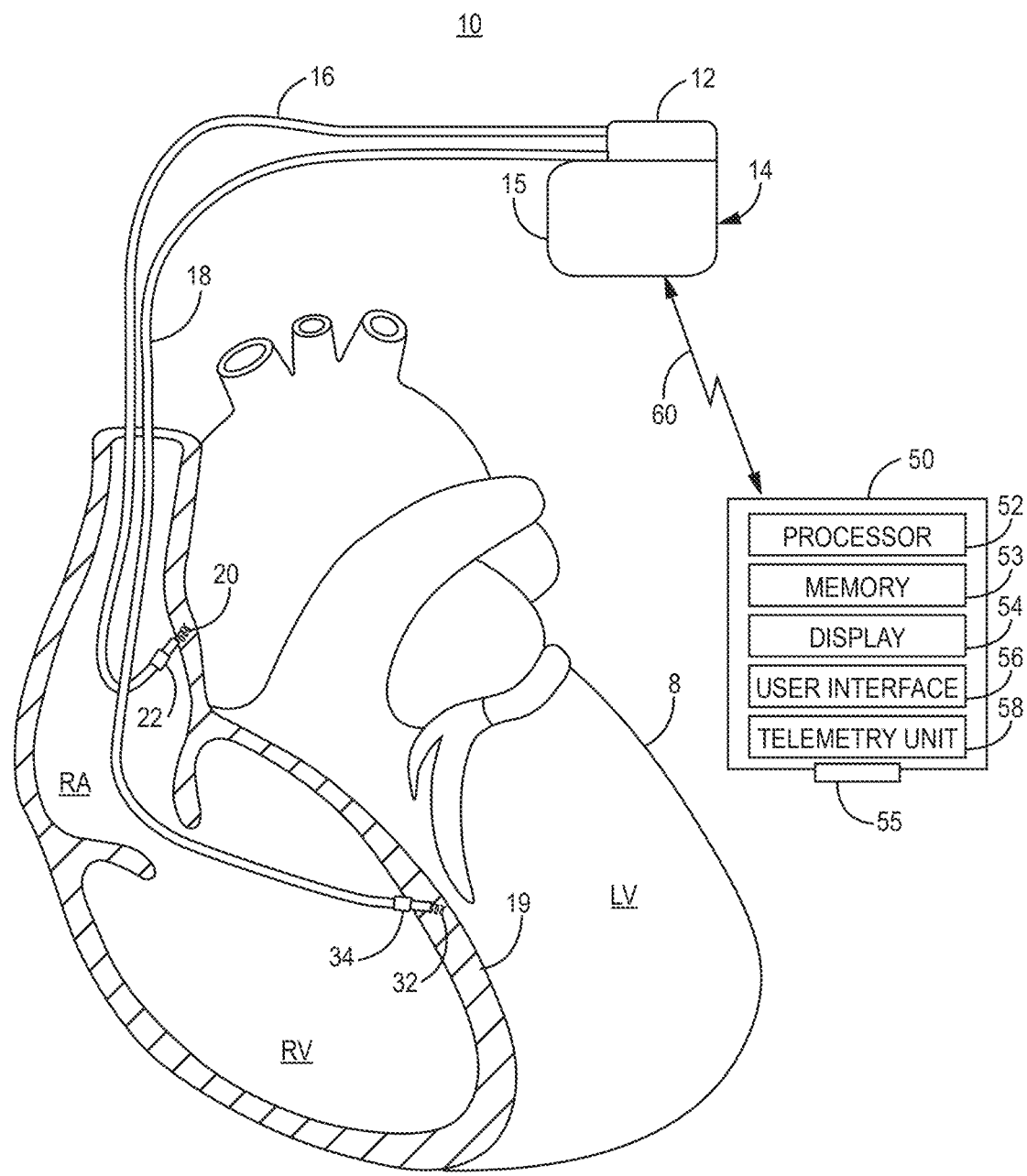
FIG. 13 is a conceptual diagram of a pacing lead coupled to the IMD of FIG. 1A according to an alternative implant position for pacing the His-Purkinje system.

FIG. 13 is a conceptual diagram of pacing lead 18 coupled to IMD 14 of FIG. 1 according to an alternative implant position for pacing the His-Purkinje system. In the example shown in FIG. 13, IMD 14 is a dual chamber device configured to receive an atrial pacing and sensing lead 16, which may be positioned in the right atrial chamber for delivering atrial pacing pulses and sensing atrial electrical signals via atrial electrodes 20 and 22. IMD 14 may be configured to sense intrinsic atrial P-waves and deliver atrial pacing pulses in the absence of sensed P-waves. IMD 14 may be configured to deliver atrial synchronized ventricular pacing by setting an AV pacing interval, sometimes referred to as an "AV delay," in response to each sensed P-wave or atrial pacing pulse and delivering ventricular pacing pulses to the His-Purkinje system via lead 18 upon the expiration of the AV pacing interval.

Pacing lead 18 is shown coupled to IMD 14 and advanced within a patient's heart 8 for positioning pacing tip electrode 32 within the interventricular septum 19 via a right ventricular approach. Pacing lead 18 may be advanced transvenously into the right ventricle (RV) via the right atrium (RA) for positioning pacing and sensing electrode 32 within the interventricular septum 19. When tip electrode 32 is advanced relatively superiorly within the interventricular septum 19, tip electrode 32 may be positioned along the inferior portion of the His bundle for delivering pacing pulses for capturing the His bundle or a portion thereof. In other examples, tip electrode 32 may be advanced within the interventricular septum 19 in the vicinity of a bundle branch of the His-Purkinje system, e.g., at a left bundle branch (LBB) pacing site or at a right bundle branch (RBB) pacing site, for delivering pacing pulses in the area of the LBB and/or RBB for capturing one or both bundle branches.

Tip electrode 32 may be selected as a pacing cathode electrode in combination with ring electrode 34 as the return anode electrode for pacing and capturing the LBB and/or RBB in various examples. In some instances, the pacing pulse amplitude and pulse width may be selected to achieve cathodal capture at the cathode electrode for capturing at least one bundle branch. In other instances, the pacing pulse amplitude and pulse width may be selected to achieve cathodal and anodal capture, which may capture both the LBB and the RBB concurrently to provide dual or bilateral bundle branch (BB) pacing using a single bipolar electrode pair. In other examples, either tip electrode 32 or ring electrode 34 may be selected as cathode electrode paired with housing 15 in a unipolar pacing electrode vector. Unipolar pacing may capture a single BB. In some cases, however, unipolar pacing may capture both the RBB and the LBB when a unipolar pacing pulse may directly capture one bundle branch while virtual current or break excitation generated by the pacing electrode may excite the other bundle branch, potentially resulting in unipolar bilateral BB pacing, with capture of both the LBB and RBB.

While pacing lead 18 is shown carrying tip electrode 32 and ring electrode 34, it is to be understood that in other examples, pacing lead 18 may include multiple electrodes along its distal portion to provide one or more selectable bipolar pacing electrode vectors and/or one or more unipolar pacing electrode vectors (with housing 15) for delivering pacing pulses to one or both of the RBB and the LBB.

IMD 14 may communicate via wireless telemetry with external device 50. As described above in conjunction with FIG. 1A, external device 50 may include a processor 52, memory 53, display unit 54, user interface 56 and telemetry unit 58. Processor 52 controls external device operations and processes data and signals received from IMD 14. Data obtained from IMD 14 via communication link 60 may be displayed on display unit 54. For example, a clinician may view cardiac electrical signals received from IMD 14 and/or results of morphology matching analysis performed according to the techniques described below, capture threshold testing results, and capture monitoring results or data derived therefrom according to any of the examples described herein.

External device 50 may include external ports 55 for electrical connection to surface ECG leads and electrodes that may be coupled to a patient implanted with IMD 14. Processor 52 may receive ECG signals for display by display unit 54 for observation by a user during His-Purkinje system pacing. Observation of ECG signals may enable a user to confirm capture of the His-Purkinje system based on improvements in the QRS signals following delivered pacing pulses, such as narrowed QRS signals indicating a more synchronous depolarization of the left and right ventricles or the disappearance of QRS abnormalities such as QRS features indicative of left bundle branch block, right bundle branch block or other ventricular conduction abnormalities.

Display unit 54, which may include a liquid crystal display, light emitting diodes (LEDs) and/or other visual display components, may generate a display of the ECG and/or EGM signals and/or data derived therefrom. Display unit 54 may be configured to generate a graphical user interface (GUI) including various windows, icons, user selectable menus, etc. to facilitate interaction by a user with the external device 50. Display unit 54 may function as an input and/or output device using technologies including liquid crystal displays (LCD), quantum dot display, dot matrix displays, light emitting diode (LED) displays, organic light-emitting diode (OLED) displays, cathode ray tube displays, e-ink, or monochrome, color, or any other type of display capable of generating tactile, audio, and/or visual output. In some examples, display unit 54 is a presence-sensitive display that may serve as a user interface device that operates both as one or more input devices and one or more output devices.

Figure 14:
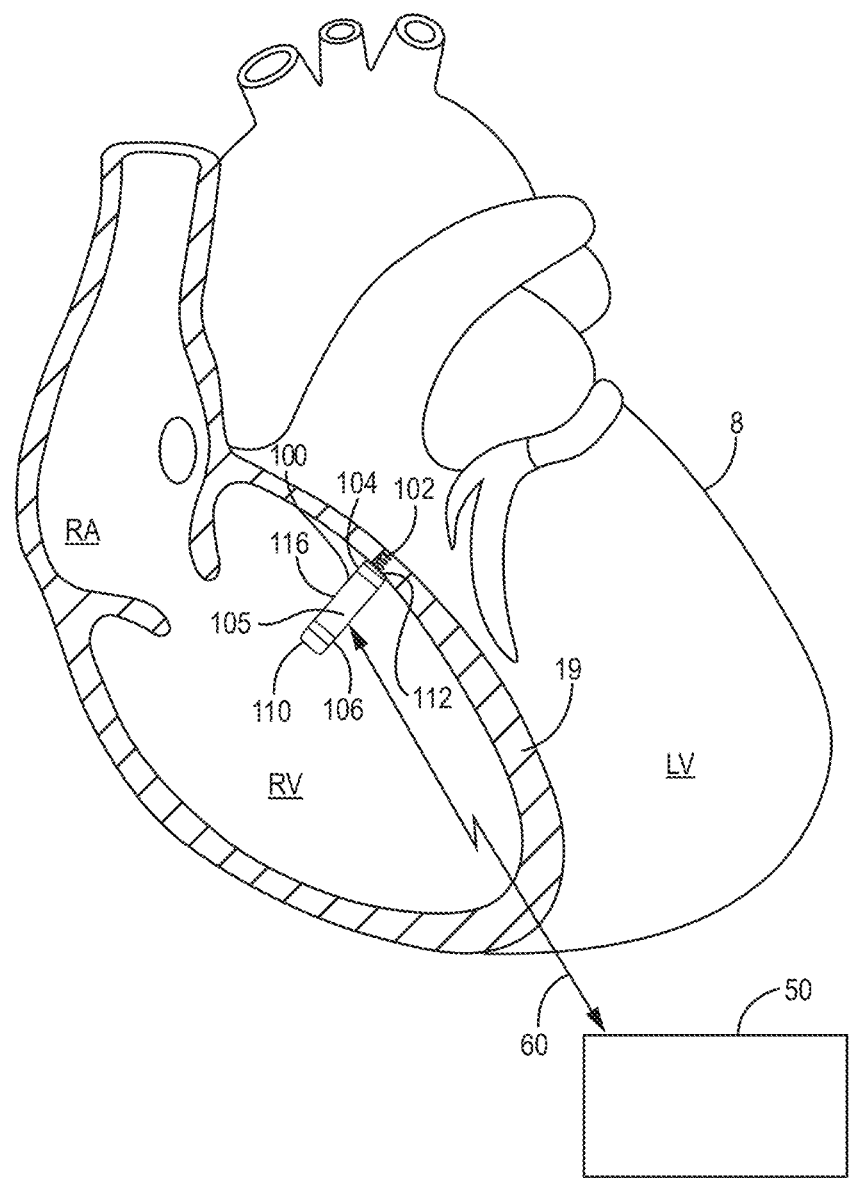
FIG. 14 is a conceptual diagram of the leadless intracardiac pacemaker of FIG. 2 shown implanted in an alternative location for providing His-Purkinje system pacing according to another example.

FIG. 14 is a conceptual diagram of the leadless intracardiac pacemaker 100 of FIG. 2 shown implanted in an alternative location within the RV along the interventricular septum 19 for providing His-Purkinje system pacing according to another example. As described above, techniques disclosed herein for performing capture detection and capture management may be used in conjunction with a leadless pacemaker, such as pacemaker 100, having a pacing electrode coupled to and extending from the pacemaker housing 105, without requiring an intervening medical lead coupled to the pacemaker for carrying the pacing and sensing electrode(s).

Pacemaker 100 may include an elongated housing 105 having a longitudinal sidewall 116 extending from a housing proximal end 110 to a housing distal end 112. Pacemaker 100 may be positioned within the RV for advancing the pacing tip electrode 102 extending from the distal end 112 of pacemaker housing 105 into the interventricular septum 19 for pacing the His-Purkinje system, e.g., in the area of inferior portion of the His bundle or along one or both of the RBB and LBB. Tip electrode 102 is shown as a "screw-in" helical electrode but may be configured as other types of electrodes capable of being advanced within the septal tissue. A proximal portion of the pacing tip electrode 102 may be electrically insulated, e.g., with a coating, in some examples such that only a distal portion of tip electrode 102, furthest from pacemaker housing distal end 112, is exposed to provide targeted pacing at a tissue site that includes the His bundle, LBB or RBB.

In other examples, tip electrode 102 may be formed having a straight shaft with a distal active electrode portion or other type of electrode that is advanceable through the interventricular septum 19 to deliver pacing, e.g., in a left portion of the septum 19 in the area of the LBB. In some examples, pacemaker 100 may include a fixation member that includes one or more tines, hooks, barbs, helices or other fixation member(s) that anchor the distal end 112 of the pacemaker 100 at the implant site and may not function as an electrode. Examples of leadless intracardiac pacemakers that may be configured for delivering cardiac pacing pulses to the His-Purkinje system that may be used in conjunction with the techniques described herein are generally disclosed in U.S. Publication No. 2019/0111270 (Zhou) and U.S. Publication No. 2019/0083800 (Yang, et al.), both of which are incorporated herein by reference in their entirety.

Pacemaker 100 may include the distal housing-based ring electrode 104 along or near the distal end 102 of pacemaker housing 105. Distal housing-based ring electrode 104 may be selectable as the return anode electrode with tip electrode 102 for bipolar pacing of the LBB or RBB in the vicinity of the tip electrode 102. Bipolar bilateral BB pacing of both the RBB and LBB simultaneously may be achieved by cathodal capture of the LBB at tip electrode 102 and anodal capture of the RBB by distal ring electrode 104. The polarities of the tip electrode 102 and the distal ring electrode 104 may be reversed to achieve cathodal capture of the RBB and anodal capture of the LBB in some examples. Distal ring electrode 104 is shown as a ring electrode circumscribing a distal portion of the housing 105 but may alternatively be a distal housing-based electrode in the form of a button electrode, hemispherical electrode, segmented electrode or the like and may be along the face of distal end 112 of housing 105 and/or along lateral side wall 116.

In the example shown, a housing-based proximal ring electrode 106, which may circumscribe all or a portion of the longitudinal sidewall 116 of the housing 105, may be provided as a return anode electrode. In other examples, a return anode electrode used in sensing and pacing may be positioned on housing proximal end 110 or on housing distal end 112 and may be a button, ring or other type of electrode. Pacing of the LBB may be achieved using the tip electrode 102 as the cathode electrode and the proximal ring electrode 106 as the return anode. Pacing of the RBB may be achieved using the distal ring electrode 104 as a cathode electrode and the proximal ring electrode 106 as the return anode. In this way, bilateral or dual bundle branch pacing may be achieved using two different bipolar pacing electrode vectors carried by housing 105.

Cardiac electrical signals produced by heart 8 may be sensed by pacemaker 100 using electrodes 102, 104 and/or 106. The cardiac electrical signal received via electrodes 102 and 104, electrodes 104 and 106 and/or electrodes 102 and 106, for example, may be processed and analyzed by sensing and control circuitry included in pacemaker 100 according to any of the example techniques disclosed herein for detecting capture of the His-Purkinje system. The cardiac electrical signals sensed by pacemaker 100 may be processed and transmitted wirelessly, e.g., as EGM signals, to external device 50 via communication link 60 in some examples. The signals may then be displayed and/or further processed and analyzed by the processor 52 of external device 50 for providing a user with visual information regarding pacing pulse output levels that result in a change in the type of capture (or loss of capture) of the His-Purkinje system. An EGM signal sensed using the proximal ring electrode 106 and distal ring electrode 104 may be considered a relatively far field signal, and an EGM signal sensed using the tip electrode 102 and ring electrode 104 may be considered a relatively near field signal for sensing QRS signals and detecting capture using the techniques disclosed herein.

Figure 15:
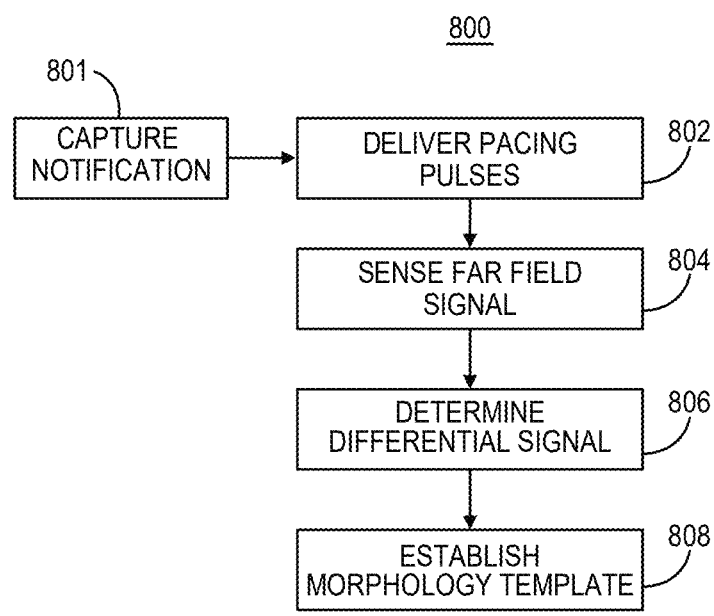
FIG. 15 is a flow chart of a method for establishing a capture detection morphology template for use in detecting capture or a change in the type of capture following a pacing pulse delivered to the His-Purkinje system according to some examples.

FIG. 15 is a flow chart 800 of a method for establishing a capture detection morphology template for use in detecting capture or a change in the type of capture following a pacing pulse delivered to the His-Purkinje system according to some examples. Flow chart 800 is described as being performed by IMD 14 (or pacemaker 100) for the sake of convenience. It is to be understood, however, that processing circuitry included in an implantable medical device and/or external device may be configured for performing the methods described in conjunction with FIG. 15 and other flow charts and diagrams presented herein in a distributed or cooperative manner. For example, processor 52 of external device 50 may perform all or a portion of the cardiac signal analysis and capture detection morphology template generation described in conjunction with FIG. 15. External device 50 may receive cardiac electrical signals sensed by the implanted device and process and analyze the received signals for establishing a capture detection morphology template. The capture detection morphology template data may then be programmed into IMD 14 (or pacemaker 100) for subsequent use in capture monitoring and capture threshold tests.

At block 802, control circuit 80 may deliver one or more pacing pulses using a selected pacing electrode vector for delivering pacing pulses to capture at least a portion of the His-Purkinje system according to any of the example locations and pacing electrode vectors described above. The pacing pulse(s) may be delivered at a pacing pulse output that is expected or known to achieve a desired capture type. For example, a relatively high pacing pulse output, e.g., 5.0 volt amplitude and 0.4 to 1 ms pulse width, may be delivered for achieving capture of at least a portion of the His-Purkinje system, e.g., all or a portion of the His bundle or one or both of the RBB and LBB, depending on the pacing electrode locations. In other examples, a pacing pulse output that is selected based on detecting a desired type of capture, e.g., NSHP or SHP capture, using any of the techniques described above may be used to deliver pacing pulses at block 802 so that the capture detection morphology template can be established for a desired or intended type of capture of at least a portion of the His-Purkinje system.

In some examples, control circuit 80 may optionally receive a capture notification (block 801) via telemetry circuit 88 from external device 50. External device 50 may transmit a capture confirmation notification, which may include a specific capture type, based on user input or analysis of surface ECG and/or EGM signals. His-Purkinje system capture may be confirmed and/or specified as being SHP, NSHP, LBB, RBB, or bilateral BB pacing capture as examples. The pacing pulse output of the pacing pulses being delivered at block 802 may be held at the current amplitude and pulse width settings associated with the capture notification to enable control circuit 80 to establish a capture detection morphology template for the confirmed capture of the His-Purkinje system, and in some instances a specified capture type. In other examples, therapy delivery circuit 84 may deliver pacing pulses at a predetermined, relatively high pacing pulse output that is expected to capture a targeted portion of the His-Purkinje system with a high degree of confidence, without requiring a capture notification signal from external device 50.

At block 804, a far field cardiac electrical signal is sensed following each delivered pacing pulse using any of the example far field sensing electrode vectors described above. For example, a far field sensing electrode vector may include tip electrode 32 paired with IMD housing 15 or ring electrode 34 paired with IMD housing. A relatively far field sensing electrode vector of pacemaker 100 may include tip electrode 102 and ring electrode 106 or ring electrode 104 and ring electrode 106. At block 806, control circuit 80 may determine a differential signal segment from the far field cardiac electrical signal using the example techniques described above. For example, control circuit 80 may include a low pass filter and a differential filter implemented in hardware, software and/or firmware. The far field cardiac electrical signal may be sampled at 256 Hz and passed through a low pass filter having an upper cut off frequency of 10 to 40 Hz in some examples or about 12 Hz in one example. The low pass filter output may be determined from the equation $y(n)=x(n-1)+x(n)+y(n-1)-y(n-1)/4$ where $x(n)$ and $x(n-1)$ are the nth and nth-1 sample points of the far field cardiac electrical signal and $y(n-1)$ is the preceding low pass filtered sample point.

A differential signal may be determined from the low pass filtered signal segments. Each sample point of the differential signal may be determined by control circuit 80 using multiple sample points of the low pass filtered signal, e.g., at least three consecutive sample points or at least five consecutive sample points of the low pass filtered far field cardiac electrical signal. In one example, each sample point of the differential signal may be determined using five consecutive points of the low pass filtered signal according to the five-point difference equation given above, e.g., $Z(n)=2*y(n-2)-y(n-1)+y(n+1)-2*y(n+2)$, though other coefficients and/or other number of sample points may be used to determine a differential signal from the low pass filtered, far field signal. It is further recognized that different filters or equations may be used when a different sampling rate is used other than 256 Hz as used in this is example.

A segment of the differential segment may be buffered in memory 82 over a predetermined time interval following each delivered pacing pulse. The differential signal segment may be 150 to 300 ms in duration or about 200 to 300 ms in duration in some examples. At block 808, control circuit 80 may establish a capture detection morphology template from at least one differential signal segment during the known (or expected) capture of at least a portion of the His-Purkinje system. The capture detection morphology template may be determined by determining an ensemble averaged differential signal segment from multiple differential signal segments, e.g., from two to eight differential signal segments or from five segments in one example. In some examples, a cross-correlation analysis may be performed between the differential signal segments before using each segment for establishing the morphology template. A cross-correlation analysis of the differential signal segments may be performed to establish the similarity of the differential signal segments buffered in memory 82. When a predetermined number of differential signal segments are determined to match each other based on the cross-correlation analysis, a capture detection morphology template may be established based on a combination of the differential signal segments, e.g., by ensemble averaging of the differential signal segments. In other examples, a clinician or user interacting with external device 50 may select one or more EGM QRS waveforms displayed by display unit 54 during delivery of His-Purkinje system pacing that are to be used for establishing the capture morphology template.

Control circuit 80 may perform capture detection by performing a wavelet transform for determining morphology matching scores between the established template and a cardiac signal segment of unknown capture type that is acquired following a pacing pulse as further described below. A wavelet transform may be performed on the morphology template for obtaining wavelet coefficients from the template. The established capture detection morphology template determined from the differential signal segments and/or corresponding wavelet coefficients may be stored in memory 82. In some examples, one or more other features of the capture detection morphology template may be determined and stored for establishing other capture detection criteria, such as a peak amplitude, peak slope, number of peaks, signal width, signal area, polarity pattern, etc.

The process of flow chart 800 is generally described for establishing a single capture detection morphology template based on cardiac signal segments acquired during one known or expected type of capture of the His-Purkinje system. In some examples, the capture detection morphology template may be established when a user or clinician confirms the greatest or observable improvement in the ECG QRS signals displayed on external device 50. It is to be understood, however, that the process of flow chart 800 may be repeated for multiple capture types that may occur at one or more pacing sites. For example, external device 50 may display one or more ECG, EGM and/or far field differential signal(s), e.g., as described below in conjunction with FIGS. 17-20. External device 50 may verify capture, which may include identifying a specific capture type, based on user input or analysis of surface ECG signals and/or EGM signals as being SHP, NSHP, LBB, RBB, or bilateral BB pacing capture as examples. A capture notification signal may be transmitted from external device 50 to IMD 14 or pacemaker 100 to trigger the IMD 14 or pacemaker 100 to establish a capture detection morphology template for a confirmed capture type of the His-Purkinje system, which may be a non-specified or specified capture type.

When a pacing electrode is positioned for His bundle pacing, a capture detection morphology template may be established during SHP capture, during NSHP capture and/or during VM capture. When the pacing electrode(s) are positioned for pacing one or both of the LBB and RBB, a capture detection morphology template may be established during LBB capture, during RBB capture, and/or during bilateral BB capture, as examples. Each capture detection morphology template of the differential signal may be stored in memory 82 for use in detecting the associated type of capture during His-Purkinje system pacing. The capture detection morphology templates may each be associated with a different type of capture by cardiac pacing pulses and may or may not be identified as a specific capture type.

Figure 16:
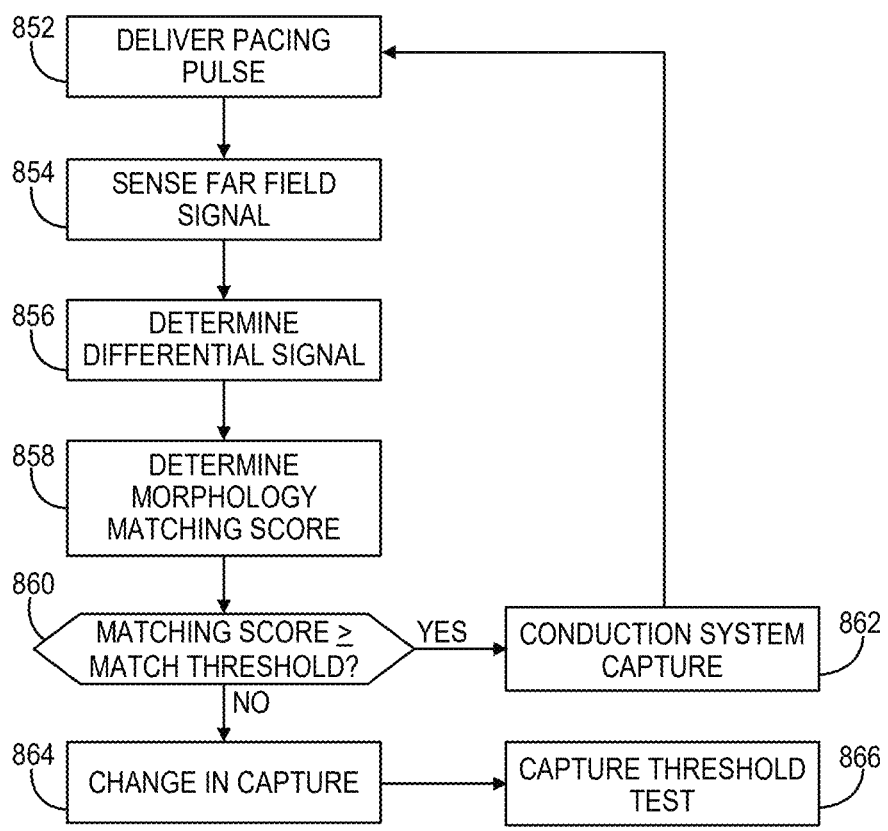
FIG. 16 is a flow chart of a method performed by a medical device for detecting capture during His-Purkinje system pacing according to one example.

FIG. 16 is a flow chart 850 of a method performed by a medical device, e.g., IMD 14 or pacemaker 100, for detecting capture during His-Purkinje system pacing according to one example. At block 852, a His-Purkinje pacing pulse is delivered by therapy delivery circuit 84. The His-Purkinje pacing pulse may be delivered as part of a ventricular pacing therapy, e.g., single chamber bradycardia pacing, atrial synchronized ventricular pacing, cardiac resynchronization therapy (CRT), rate response pacing or other pacing therapy. The process of flow chart 852 may be performed by IMD 14 or pacemaker 100 as part of a capture management test for verifying capture of the His-Purkinje pacing pulse delivered at block 852 for managing and maintaining capture during the pacing therapy. The process of flow chart 850 may be performed on a beat by beat basis (on every pacing pulse) or less often, e.g., once every N beats where N may be anywhere from 5 to 100 as examples or on a scheduled basis, e.g., once per minute, once per hour, once per day or other selected intervals or at one or more scheduled time(s) of day.

The pacing pulse may be delivered at block 852 according to a pacing pulse amplitude and pulse width currently in effect for the pacing therapy. The pacing pulse amplitude and pulse width may have been set based on a previous capture threshold test performed by IMD 14 or pacemaker 100 or at pacing pulse output that is programmed by a user and previously known to achieve a desired capture type, e.g., SHP, NSHP, LBB, RBB, or bilateral BB capture.

At block 854, sensing circuit 86 senses a far field cardiac electrical signal that is passed to control circuit 80 for processing and analysis. At block 856, control circuit 80 determines the low pass filtered, differential signal from the far field cardiac electrical signal received by control circuit 80 following the delivered pacing pulse. Control circuit 80 may buffer the differential signal in memory 82 over a time segment beginning from the delivered His-Purkinje system pacing pulse, or from a delay time after the delivered pacing pulse, and extending over a predetermined time interval corresponding to the time duration of the previously established capture detection morphology template (e.g., as described in conjunction with FIG. 15).

Control circuit 80 determines a morphology matching score between the differential signal segment following the delivered pacing pulse and the capture detection morphology template at block 858. The morphology matching score may be determined by performing a wavelet analysis, e.g., using a Haar transform or other transform analysis, or other waveform correlation analysis. The techniques disclosed herein are not necessarily limited to a particular waveform morphology matching technique and other waveform correlation analyses or morphology matching techniques may be used for determining when an EGM signal segment matches the capture detection morphology template.

At block 860, control circuit 80 compares the morphology matching score to a match threshold. The match threshold may be between 30 and 80, as examples, out of a possible matching score of 0 to 100. As described below, one or more matching scores may be programmed by a user and/or established by control circuit 80 (or external device processor 52) based on a distribution of morphology matching scores determined following His-Purkinje system pacing pulses that are delivered at different pacing pulse outputs. When the morphology matching score is greater than or equal to the match threshold at block 860, control circuit 80 may detect capture of the His-Purkinje conduction system at block 862. The specific type of capture of the His-Purkinje system may correspond to the type of capture for which the capture detection morphology template was established. In some cases, however, the specific type of capture of at least a portion of the His-Purkinje system may not be identified. In some examples, control circuit 80 may analyze features of the differential signal to discriminate between specific capture types, e.g., SHP, NSHP and VM capture, according to any of the examples described above, e.g., in conjunction with FIGS. 9-12. When His-Purkinje conduction system capture is detected at block 862, control circuit 80 may return to block 852 to repeat the process on a beat-by-beat or other scheduled basis according to a capture management protocol.

When control circuit 80 determines that the matching score is less than the match threshold at block 860, control circuit 80 may determine a change in capture type at block 864. For example, when the capture detection morphology template is established during SHP capture, the capture type may have changed from SHP pacing to VM capture or loss of capture of both the His-Purkinje system and the ventricular myocardium. When the capture detection morphology template applied at block 858 has been established during NSHP capture, the capture type may have changed from NSHP capture to SHP capture or to VM capture or total loss of capture. In another example, when the capture detection morphology template is established during LBB capture, the capture type may have changed from LBB capture to VM capture or loss of capture. In yet another example, when the capture detection morphology template is established during bilateral BB capture, the capture type may have changed from bilateral BB capture to LBB only capture, RBB only capture, VM capture or total loss of capture. The change in capture type detected at block 864 may be a change from a desired capture type of the His-Purkinje system to loss of the desired capture type, which may still include capture of a portion of the His-Purkinje system and/or the ventricular myocardium in some cases but may not be an intended or desired type of capture of the His-Purkinje system, which corresponds to the capture type associated with the capture detection morphology template used at block 858.

In response to detecting a change in capture type at block 864, control circuit 80 may advance to block 866 to perform a capture threshold test. The capture threshold test may be performed by control circuit 80, in cooperation with sensing circuit 86 and therapy delivery circuit 84 for re-establishing an intended type of capture of the His-Purkinje system by adjusting the pacing pulse output above a capture threshold that results in a morphology matching score that is greater than the match threshold. Example methods for performing a capture threshold test are described below in conjunction with FIG. 21.

Figure 17:
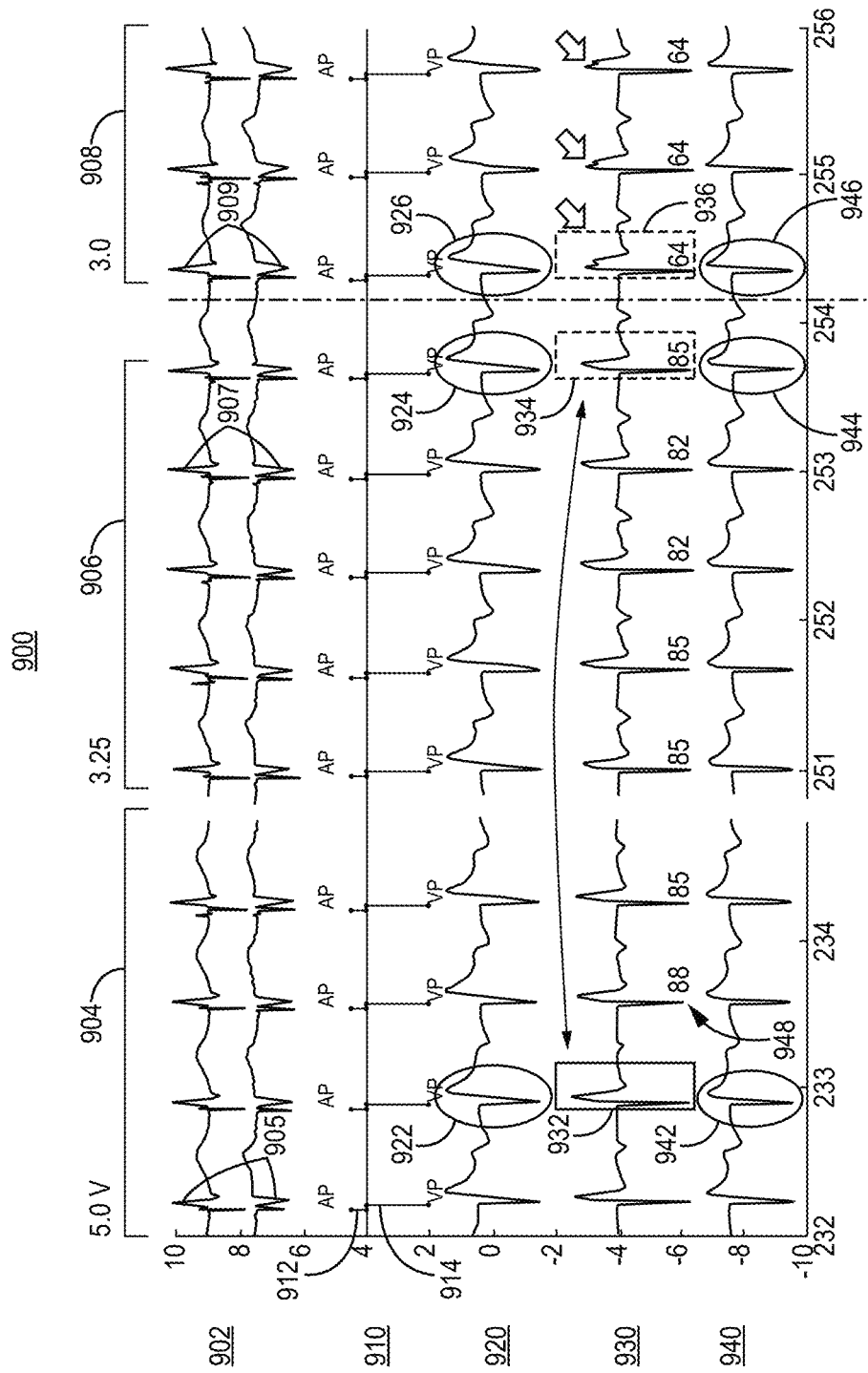
FIG. 17 is a diagram of cardiac electrical signals that may be processed and analyzed for detecting a change in capture type of the His-Purkinje system according to one example.

FIG. 17 is a diagram 900 of cardiac electrical signals that may be analyzed by control circuit 80 (and/or external device processor 52) for detecting a change in capture type of the His-Purkinje system according to one example. The diagram of 900 may represent a portion of a user interface that may be displayed by external device display unit 54 in some examples to enable a clinician to observe the cardiac electrical signals that are sensed and processed by an implanted medical device, e.g., IMD 14 or pacemaker 100. In this example, two surface ECG signals 902 may be included in the display that may be sensed by surface or skin electrodes coupled to the patient and received by external device 50.

A marker channel 910 may be generated by IMD 14 for displaying the timing of atrial and ventricular events that are sensed or paced, e.g., P-waves or R-waves sensed by sensing circuit 86 or pacing pulses generated by therapy delivery circuit 84. In the example shown, atrial pacing pulses (AP) 912 are shown followed by ventricular pacing pulses (VP) 914 delivered at an AV pacing interval during an atrial synchronous ventricular pacing mode, e.g., a DDD pacing mode, by IMD 14. The ventricular pacing pulses 914 may be delivered to capture the LBB in the interventricular septum in this example for providing pacing to the His-Purkinje system to achieve a relatively more physiological response to the ventricular pacing pulses 914 compared to capturing only the ventricular myocardium.

The IMD 14 may sense a near field EGM signal 940, e.g., between the pacing tip electrode 32 and ring electrode 34 as shown in FIG. 13. IMD 14 senses the far field EGM signal 920, e.g., between the ring electrode 34 and the IMD housing 15 or between tip electrode 32 and housing 15. As described above, control circuit 80 processes the far field EGM signal 920 to produce the low pass filtered differential signal 930. All or any combination of one or more ECG signals 902, marker channel 910, far field EGM signal 920, differential signal 930, and near field EGM signal 940 may be displayed by external device 50 in a user interface. In some examples, at least the differential signal 930 is displayed in the user interface to enable a user to clearly observe changes in the morphology of the differential signal 930 during His-Purkinje system pacing, in this example LBB pacing, at one pacing pulse output or multiple different pacing pulse outputs.

In the example shown, a first group 904 of LBB pacing pulses 914 are delivered at a pulse amplitude of 5.0 volts (and pulse width of 0.4 ms). At this relatively high pacing pulse output amplitude in the area of the LBB, LBB capture may be expected or known to occur. In some examples, a clinician may confirm LBB capture during pacing at 5.0 volts pulse amplitude, e.g., based on observation of a narrow width of the QRS signals 905 or disappearance of a LBB block morphology of the ECG signals 902. The pulse amplitude of the LBB pacing pulses 914 is reduced to 3.25 volts during the second group 906 of LBB pacing pulses and further reduced to 3.0 volts during the third group 908 of LBB pacing pulses. The pulse width is kept constant at 0.4 ms in this example.

Based on expected LBB capture during the highest pacing pulse amplitude in group 904 or based on receiving a notification signal from external device 50 in response to user input confirming LBB capture, control circuit 80 may establish a capture detection morphology template based on one or more segments 932 of the differential signal 930. The differential signal segment 932 may be determined from the far field EGM signal 920 and buffered in memory 82 following one or more LBB pacing pulses delivered during the 5.0 volt pacing pulse amplitude or any other relatively high pacing pulse output resulting in expected or known LBB capture. In some examples, a user may select which signal segments of differential signal 930 (displayed in a graphical user interface on display unit 54) are to be used for establishing the capture detection morphology template by manually selecting signal segments, e.g., using a touch screen, pointer, mouse, keyboard or other user interface.

Control circuit 8 may perform a morphology matching analysis between the capture detection morphology template established from at least one differential signal segment 932 and differential signal segments 934 and 936 acquired following LBB pacing pulses delivered at different pacing pulse outputs. In the example of FIG. 17, the morphology matching scores 948 are determined for each segment of the differential signal 930 analyzed following each LBB pacing pulse after establishing the capture detection morphology template. Display unit 54 may be configured to generate a display of the morphology matching scores 948 in a user interface for observation by a user for use in confirming and identifying different His-Purkinje capture types. The morphology matching scores 948 determined through wavelet analysis or other morphology matching analysis may be buffered in memory 82 of IMD 14 during a capture threshold test being performed by IMD 14 and may be transmitted to external device 50 in some examples.

The morphology matching scores 948 are observed to be relatively high, in this example all greater than 80, during LBB pacing using 5.0 volt pacing pulses (first group 904) and 3.25 volt pacing pulses (second group 906). When the pacing pulse amplitude it reduced to 3.0 volts (third group 908), the morphology matching scores drop to 64 in this example. The change in morphology matching scores from consistently greater than 80 to 64 indicates a change in capture type, e.g., from LBB capture to loss of LBB capture, which may still include VM capture. The change to VM capture in the interventricular septum still results in an evoked QRS signal but with a sudden change in morphology (as evidenced by the sudden drop in matching scores) at the 3.0 volts pulse amplitude compared to 3.25 volts pulse amplitude. VM capture may be occurring in the interventricular septum, as also evidenced by a relatively wider QRS waveform 909 in the ECG signals 202 compared to the narrower QRS waveforms 905 and 907 during higher amplitude pacing and LBB capture.

While a slightly wider QRS signal may be observed in the surface ECG signals 902, a change in the morphology of the evoked response signals in the near field EGM signal 940 and the far field EGM signal 920 is difficult to observe when the pacing pulse amplitude is reduced from 3.25 volts to 3.0 volts. For example, the morphology of the QRS signal 924 in the far field EGM signal 920 during LBB capture is very similar to the morphology of the QRS signal 926 in the far field EGM signal 926 after LBB capture is lost. Morphology matching analysis of the QRS signal 926 in the far field EGM signal 926 may result in a matching score that is similar to the matching score determined from the QRS signal 924 when both are compared to the capture detection morphology template established using a QRS signal 922 during the 5.0 volt pacing amplitude. Control circuit 80 may not detect a change in capture type during LBB pacing based on a waveform morphology matching analysis of the far field EGM signal 920.

The morphology of the near field EGM signal 940 is observed to change slightly when LBB capture is lost in this example. The QRS signal 946 after LBB capture is lost is observed to be slightly different than the QRS signal 944 of the near field EGM signal 940 during LBB capture. A capture detection morphology template may be established using the QRS signal 942 during known LBB capture when LBB pacing pulses are delivered with the 5.0 volt pacing pulse amplitude. However, the magnitude of change in a morphology matching score determined from the QRS signal 946 after LBB capture is lost compared to a morphology matching score determined from the QRS signal 944 before LBB capture is lost may not be large enough to reliably detect a change in capture type.

The morphology change from LBB capture to loss of LBB capture in the differential signal 930 is more easily observed by a user than any slight morphology change in the far field EGM signal 920 or the near field EGM signal 940. Accordingly, display of the differential signal 930 and corresponding morphology matching scores are useful to a user interacting with a user interface for selecting and programming His-Purkinje system pacing control parameters, which may include programming commands for establishing a capture detection morphology template, programming a morphology match threshold, and/or programming pacing pulse amplitude and pulse width. A clear change in capture type can be observed, e.g., on a user interface, from the differential signal 930 and corresponding morphology matching scores 948 when the pacing pulse amplitude is decreased below a LBB capture threshold.

Furthermore, control circuit 80 can be configured to detect the change in capture type from LBB capture to a different type of capture based on the morphology matching scores 948 buffered in memory 82. As described in conjunction with FIG. 15, control circuit 80 can be configured to establish the capture detection morphology template from one or more differential signal segments 932 during a relatively high pacing pulse output, corresponding to expected LBB capture or LBB capture confirmed based on a signal received from external device 50. Control circuit 80 may detect a change in capture type, e.g., loss of LBB capture which may be a change to VM capture, when the morphology matching score falls below a match threshold. In the example of FIG. 17, the match threshold may be set between 70 and 80 or about 75 in this example. The match threshold may be a predetermined value stored in memory 82. In some examples, a user may program the match threshold based on the morphology matching scores 948 observed on a user interface. The user programmed morphology match score may be used by control circuit 80 during capture management monitoring and capture threshold tests.

As described in conjunction with FIG. 16, during a pacing therapy, control circuit 80 may periodically (or beat by beat) determine a morphology matching score between a differential signal segment and a previously established capture detection morphology template. When at least one morphology matching score (or a threshold number of morphology match scores) is(are) less than a match threshold, control circuit 80 may perform a capture threshold test.

During the capture threshold test, control circuit 80 may adjust the pacing pulse output, e.g., by progressively decreasing the pacing pulse amplitude as shown in FIG. 17, until the morphology matching score falls below a match threshold. The lowest pacing pulse amplitude at which the morphology matching score is greater than the match threshold may be determined as the capture threshold. In some examples, the lowest pacing pulse output for which the morphology matching score is greater than a match threshold for at least a threshold number of pacing pulses is determined as the capture threshold corresponding to the capture type associated with the capture detection morphology template. In the example of FIG. 17, control circuit 80 may determine that the LBB capture threshold is 3.25 volts (corresponding to the second group 906) due to the drop in the morphology matching scores during pacing at 3.0 volts.

Figure 18:
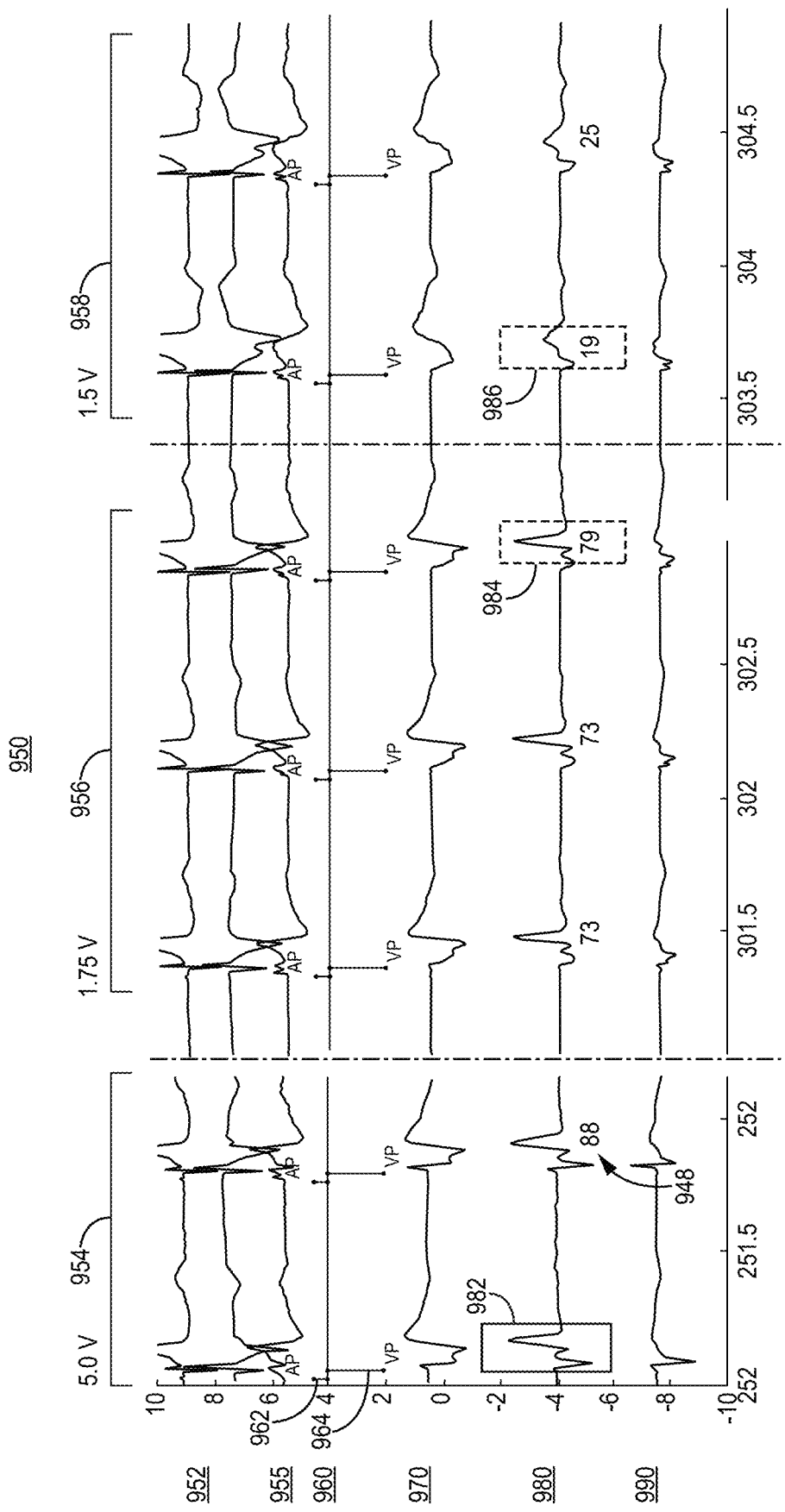
FIG. 18 is a diagram of cardiac electrical signals that may be sensed, processed and analyzed for detecting a change in capture type during cardiac pacing of the His-Purkinje system.

FIG. 18 is a diagram 950 of cardiac electrical signals that may be sensed, processed and analyzed for detecting a change in capture type during cardiac pacing of the His-Purkinje system. In this example, pacing pulses may be delivered at a His bundle pacing site from an atrial approach, e.g., as shown in FIG. 1A, or from a right ventricular approach, e.g., as shown in FIG. 13. The signals shown in FIG. 18 may be displayed in a user interface on display unit 54 of external device 50 in some examples. Surface ECG signals 952 may be received by the external device 50 from surface or skin electrodes. A marker channel 960 may be generated by IMD 14 and transmitted to external device 50 for display in a user interface. The marker channel 960 includes markers indicating the timing of ventricular pacing pulses 964 and atrial pacing pulses 962, during atrial synchronous ventricular pacing in this example.

Diagram 950 includes far field EGM signal 970, e.g., sensed by sensing circuit 86 between the tip electrode 32 and housing 15 or the ring electrode 34 and housing 15, the differential signal 980 determined from the far field signal using the techniques described above, and the near field EGM signal 990, e.g., sensed between the tip electrode 32 and ring electrode 34. In this example, an atrial EGM signal 955 is shown, which may be sensed by sensing circuit 86 using atrial tip electrode 20 or atrial ring electrode 22 (e.g., see FIG. 1A or FIG. 13) paired with IMD housing 15, for example. The atrial EGM signal 955 may be sensed as a far field EGM signal that may be used by control circuit 80 for determining a differential signal that is analyzed for detecting a change in His-Purkinje system capture type in some examples. As observed in FIG. 18, the morphology of the atrial EGM signal 955, the far field EGM signal 970 and the differential signal 980 changes as the His bundle pacing pulse amplitude is decreased from 5.0 volts (first group 954) to 1.75 volts (second group 956) to 1.5 volts (third group 958).

Control circuit 80 (or external device processor 52) may establish a capture detection morphology template during relatively high pacing pulse output, e.g., during pulse amplitude of 5.0 volts and pulse width of 1 ms (first group 954) from at least one differential signal segment 982. The capture type in this example may be NSHP capture at 5.0 volts, which changes to VM capture at 1.5 volts (group 958). Control circuit 80 may be configured to detect a change from NSHP capture to a different capture type based on the morphology matching scores determined between segments of the differential signal 980 that are determined from the far field EGM signal 970 sensed following His bundle pacing pulses and the capture detection morphology template that corresponds to NSHP capture (or more generally any capture type that is occurring at the pulse amplitude of 5.0 volts).

In the example shown, control circuit 80 may detect NSHP capture based on a morphology matching score that is greater than or equal to a match threshold of 50, 60, or 70 as examples. The differential signal segment 984 is acquired after decreasing the pulse amplitude to 1.75 volts (second group 956). The morphology match score of 79 represents a high correlation to the capture detection morphology template established based on differential signal segment 982. At 1.75 volts pulse amplitude, the capture type may still be NSHP capture, corresponding to the capture type associated with the capture detection morphology template.

The morphology matching scores 948 suddenly and significantly decrease when the pacing pulse amplitude is decreased from 1.75 volts to 1.5 volts. Control circuit 80 may detect a change in capture type when the morphology matching score is lower than a match threshold. In FIG. 18, NSHP capture occurs when the pacing amplitude is 1.75 volts and VM capture occurs when the pacing amplitude is decreased to 1.5 volts, due to loss of His bundle capture at 1.5 volts in this example. As such, control circuit 80 may detect a change in capture type when the morphology matching score between at least one differential signal segment 986 and the capture detection morphology template is less than a match threshold.

A user interacting with a user interface including a display of the morphology matching scores 948 and corresponding pacing pulse output and optionally one or more cardiac electrical signals, such as differential signal 982, may program a match threshold based on the morphology matching scores observed during different capture types. For example, a user may program a match threshold of 50 for detecting NSHP capture. When the morphology matching score falls below the match threshold, a change in capture type may be detected by control circuit 80, e.g., from NSHP to VM capture as in the example of FIG. 18. In other examples, the match threshold may be set by control circuit 80 based on the morphology match scores 948. For example, control circuit 80 may set the match threshold to a percentage or offset less than the average match scores at the high pacing pulse output (group 954) or based on the difference between morphology match scores of group 954 and morphology match scores of group 958.

Figure 19:
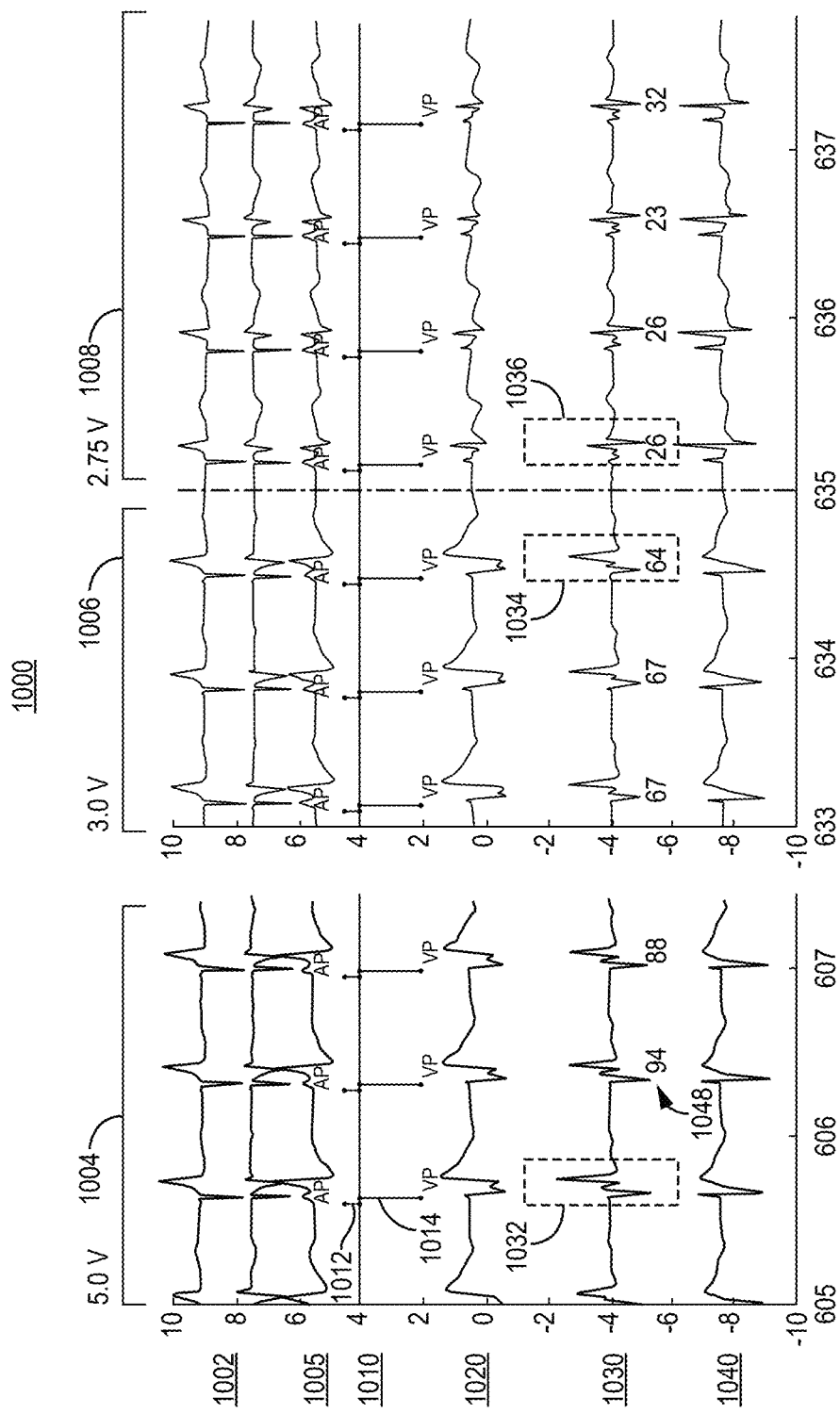
FIG. 19 is a diagram of another example of cardiac electrical signals that may be sensed, processed and analyzed for detecting a change in capture type during His-Purkinje system pacing.

FIG. 19 is a diagram 1000 of another example of cardiac electrical signals that may be sensed, processed and analyzed for detecting a change in capture type during His-Purkinje system pacing. Any combination of the cardiac electrical signals shown in FIG. 19 may be arranged in a user interface displayed on external device display unit 54. As described above in conjunction with FIGS. 17 and 18, diagram 1000 includes surface ECG signals 1002, an atrial EGM signal 1005, marker channel 1010 displaying the timing of ventricular pacing pulses 1014 and atrial pacing pulses 1012, a far field ventricular EGM signal 1020, a differential signal 1030 determined from the far field ventricular EGM signal 1020, and a near field ventricular EGM signal 1040.

Control circuit 80 (or external device processor 52) may receive the far field EGM signal 1020 during His bundle pacing at a relatively high pacing pulse output, e.g., 5.0 volts pulse amplitude (and a pulse width of 0.5 ms in this example) indicated by the first group 1004 of His bundle pacing pulses. Control circuit 80 may establish a capture detection morphology template using at least one differential signal segment 1032 acquired following a pacing pulse delivered using a relatively high pacing pulse output, during known or expected capture of the His bundle, which may be SHP or NSHP capture. In the example of FIG. 19, NSHP capture is achieved at 5.0 volts pulse amplitude. Control circuit 80 may compare the morphology matching score determined between the capture detection morphology template and a differential signal segment 1034 or 1036 during an unknown capture type.

In the example shown the morphology matching scores 1048 are greater than 60 during NSHP capture, when the pacing pulse amplitude is 3.0 volts (second group 1006) or higher. The morphology matching scores drop by about 50%, e.g., to 32 or less, when the pacing pulse amplitude is reduced from 3.0 volts to 2.75 volts (group 1008). Control circuit 80 may detect a change in capture type in response to the morphology matching score being less than a match threshold, e.g., less than 60, 55, 50, 45, 40, or 35 as examples. In this case the change in capture type may be a change from NSHP capture to SHP capture. At 2.75 volts, capture of surrounding ventricular myocardium may be lost while capture of the His bundle is maintained. A further reduction in pacing pulse output may lead to total loss of capture, in which case the evoked response is no longer present and the morphology matching score may decrease further.

In some examples, control circuit 80 may be configured to establish more than one capture detection morphology template each associated with a different type of capture. Control circuit 80 may be configured to establish a first morphology template from at least one differential signal segment 1032 obtained during a relatively high pacing pulse output. Control circuit 80 may be configured to decrease the pacing pulse output until a threshold change in the morphology matching score is detected or the morphology matching score falls below a predetermined threshold or a percentage of the morphology matching scores determined during the relatively high pacing pulse output. For example, when a pacing pulse amplitude is reached for which the morphology matching scores are consistently within a threshold range of each other and less than a threshold, percentage, average, median, minimum or other metric of the morphology matching scores determined at the starting, relatively high pacing pulse amplitude, a second capture detection morphology template may be established. In the example shown, a morphology template may be established using one or more differential signal segments 1036 that are acquired during a pacing pulse output that results in a reduction in the morphology matching scores compared to the morphology template established during 5.0 volt pacing but still correspond to a type of capture of the His-Purkinje system, in this case SHP capture.

Control circuit 80 may continue to decrease the pacing pulse output until SHP capture is lost in this case, resulting in a total loss of capture, to enable determination of the SHP capture threshold. In this way, control circuit 80 may establish a capture detection morphology template and a capture threshold corresponding to each of SHP capture and NSHP capture. When the morphology matching score determined between an unknown differential signal segment and a first capture detection morphology template falls below a first threshold, control circuit 80 may detect a first change in the type of capture, e.g., from NSHP capture to a loss of NSHP capture. Control circuit 80 may then compare the unknown differential signal segment(s) to a second capture detection morphology template, e.g., a capture detection morphology template established based on differential signal segment 1036, corresponding to a different capture type (e.g., SHP capture) than the first capture detection morphology template (e.g., corresponding to NSHP capture).

When the morphology matching scores of subsequent unknown QRS waveforms determined using the second capture detection morphology template are greater than a respective second match threshold, the second capture type may be detected. When the morphology matching scores determined using the second capture detection morphology template fall below the second match threshold, a second change in capture type may be detected. In the example of FIG. 19, the second change in capture type may be a loss of SHP capture resulting in total loss of ventricular capture. One of the capture detection morphology templates, e.g., the NSHP capture detection morphology template based on differential signal segment 1032 or the SHP capture detection template based on differential signal segment 1036, that is associated with a desired or intended type of capture of the His-Purkinje system may be selected and used by control circuit 80 during capture monitoring to verify that the capture type corresponds to the capture type associated with the selected capture detection morphology template.

In the example of FIG. 19, the ventricular myocardial capture threshold is higher than the His bundle capture threshold resulting in NSHP capture at a higher pacing pulse output than the pacing pulse output required for SHP capture. SHP capture may be confirmed by a user interacting with a user interface displaying the cardiac electrical signal(s) and morphology matching scores shown in FIG. 19. For example, SHP capture may be confirmed based on user observation of the relatively narrower QRS signals of ECG signals 1002. In some examples, external device processor 52 may be configured to confirm SHP capture based on an analysis of the ECG and/or EGM signals according to any of the examples described herein. SHP capture may be confirmed by control circuit 80 based on the signal analysis techniques described above, e.g., in conjunction with FIG. 9.

In this case, a change from a lower morphology matching score to a higher morphology matching score (when compared to a morphology template established based on differential signa segment 1032) may be an indication of a change from an intended or desired capture type, e.g., SHP capture, to a different capture type, e.g., NSHP capture. Control circuit 80 may perform capture management and capture threshold tests to identify a pacing pulse output that maintains SHP capture during His bundle pacing based on maintaining the morphology matching score in a range, e.g., between 20 and 40, corresponding to SHP capture when compared to a capture detection morphology template that corresponds to NSHP capture that occurs at higher pacing pulse outputs when the ventricular myocardial capture threshold is higher than the His bundle capture threshold. In other examples, once the SHP capture type is identified, control circuit 80 may establish a SHP capture detection morphology template based on at least one differential signal segment 1036 during SHP capture. Control circuit 80 may then maintain SHP capture based on relatively high morphology matching scores between unknown differential signal segments during His bundle pacing and the SHP capture detection morphology template.

Figure 20:
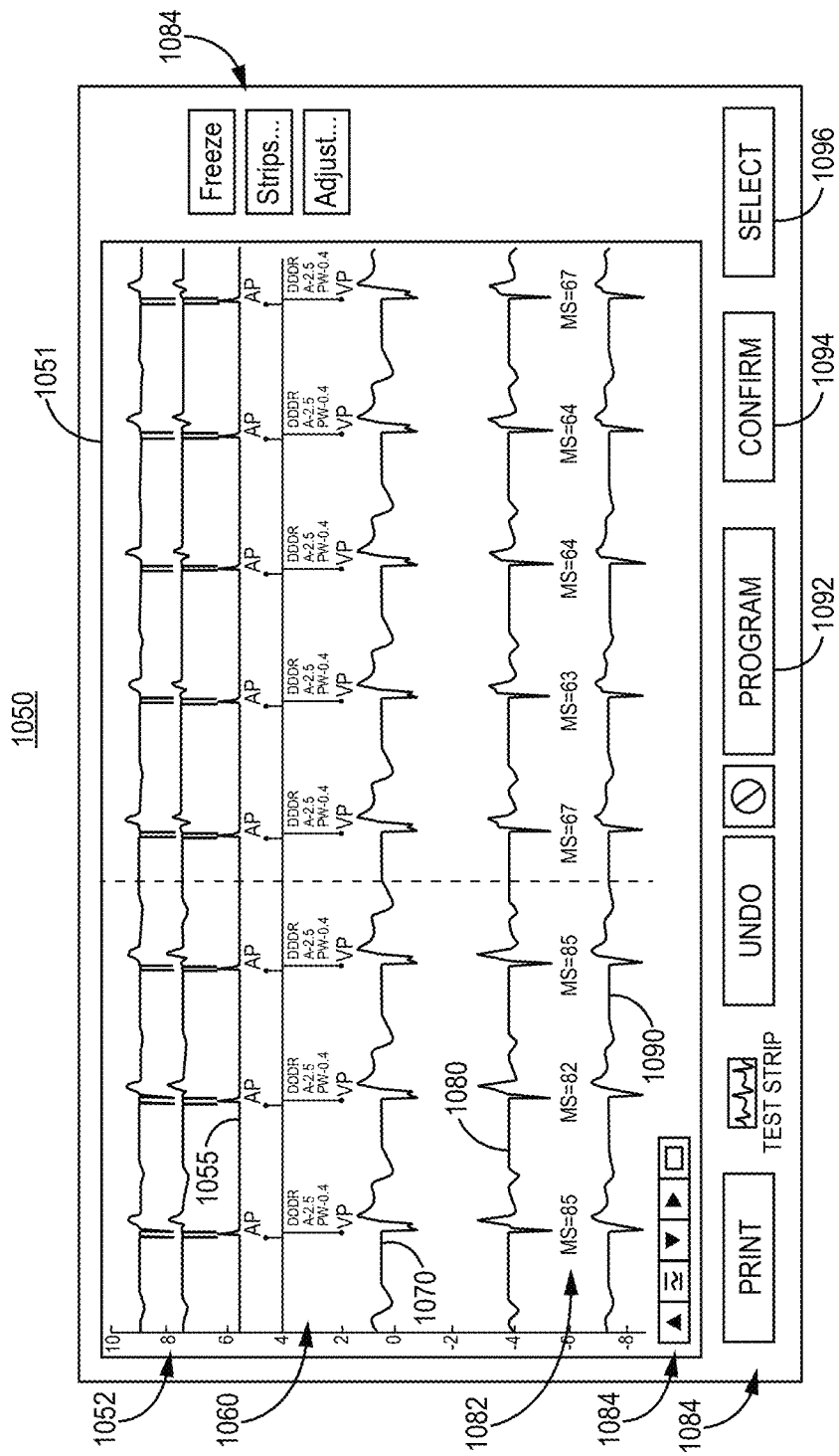
FIG. 20 is a diagram of a graphical user interface (GUI) that may be generated for display by an external device.

FIG. 20 is a diagram of a graphical user interface (GUI) 1050 that may be generated for display by display unit 54 of external device 50. Processor 52 of external device 50 may receive one or more surface ECG signals 1052 via interface 55 (shown in FIG. 13). Processor 52 may receive an atrial EGM signal 1055, marker channel signal 1060, far field EGM signal 1070, differential signal 1080 determined from the far field EGM signal 1070 and near field EGM signal 1090 via telemetry unit 58 from IMD 14 (or pacemaker 100) during a communication session. External device processor 52 may receive the morphology match scores 1082 from IMD 14 (or pacemaker 100) via telemetry unit 58 or determine morphology match scores 1082 from the received differential signal 1080.

Display unit 54 may receive the signals from processor 52 for generating a display of GUI 1050 including a signal window 1051 that includes a display of at least the differential signal 1080 and corresponding morphology match scores 1082 in some examples. In order to enable a user to clearly identify when pacing evoked QRS signals are occurring, signal window 1051 may include marker channel 1060 displaying markers indicating the timing of ventricular pacing pulses delivered to the His-Purkinje system and, depending on the pacing mode and intrinsic cardiac activity, atrial pacing pulse markers, atrial sense markers, and ventricular sense markers. Additional cardiac electrical signals, such as any of the ECG signals 1052, far field EGM signal 1070 and/or near field EGM signal may optionally be included in signal window 1051.

GUI 1050 may include one or more user input areas 1084 for a user to interact with the GUI for adjusting the display of signals in signal window 1051, e.g., for adjusting the vertical and/or horizontal scales, freezing, printing, storing, recording or saving information displayed in GUI 1050. In the example shown, GUI 1050 may include a program button 1092, a confirm button 1094 and a select button 1096 as examples of user interactions with GUI 1050 that may enable a user to select and program capture detection parameters such as morphology match thresholds, select segments of the differential signal used for establishing one or more capture detection morphology template(s), and/or confirming His-Purkinje system capture and/or a change in capture type.

User input received via GUI 1050 may be used by external device processor 52 and/or transmitted to IMD 14 or pacemaker 100 for use by control circuit 80 for establishing capture detection morphology templates, establishing morphology match thresholds, selecting or adjusting pacing pulse output, instructing IMD 14 or pacemaker 100 to perform a capture threshold search, or the like.

Accordingly, the techniques set forth herein provide specific improvements to the computer-related field of programming medical devices that have practical applications. For example, the use of the techniques herein may enable external device 50 to generate visualizations of the differential signal and/or morphology matching scores that are determined by IMD 14 or pacemaker 100 for performing capture management of the His-Purkinje system. Such visualizations may enable an external device, such as external device 50, to inform a user as to how the IMD 14 or pacemaker 100 is identifying capture of the His-Purkinje system so that a user can visually confirm correct capture detection or changes in capture and make any adjustments to programmed pacing parameters and/or capture management control parameters as needed.

By providing the GUI 1050 or other user interface for displaying the data relating to detecting capture of the His-Purkinje system or a change in capture type, the likelihood of human error in programming pacing control parameters such as pacing electrode vector and pacing pulse output for pacing the ventricles via the His-Purkinje system is reduced. The displayed data provides a higher confidence in the capture management performance of the IMD 14 or pacemaker 100 and provides confidence in safely programming pacing control parameters and capture management control parameters.

For example, a user may manually select beats (QRS waveforms) used for establishing the capture detection morphology template(s), manually enter a command to establish the capture detection morphology template(s) when a desired type of capture or desired improvement in the cardiac electrical signals is observed by the user and/or manually program the match threshold(s) based on the visual display of capture management data presented in GUI 1050. By providing a user with a visual representation of the differential signal and morphology matching scores, reliable His-Purkinje system pacing is promoted by enabling a user to confirm acceptable capture management performance by the IMD 14 or pacemaker 100 and/or manually program or select capture management control parameters when needed. Furthermore, the techniques disclosed herein may reduce the complexity of programming a medical device to perform His-Purkinje system pacing capture management. As such, the techniques disclosed herein may enable a medical device, such as IMD 14 or pacemaker 100, to be programmed to deliver His-Purkinje system pacing pulses and monitor and maintain His-Purkinje system capture in a manner that is simplified, flexible, and patient-specific.

Figure 21:
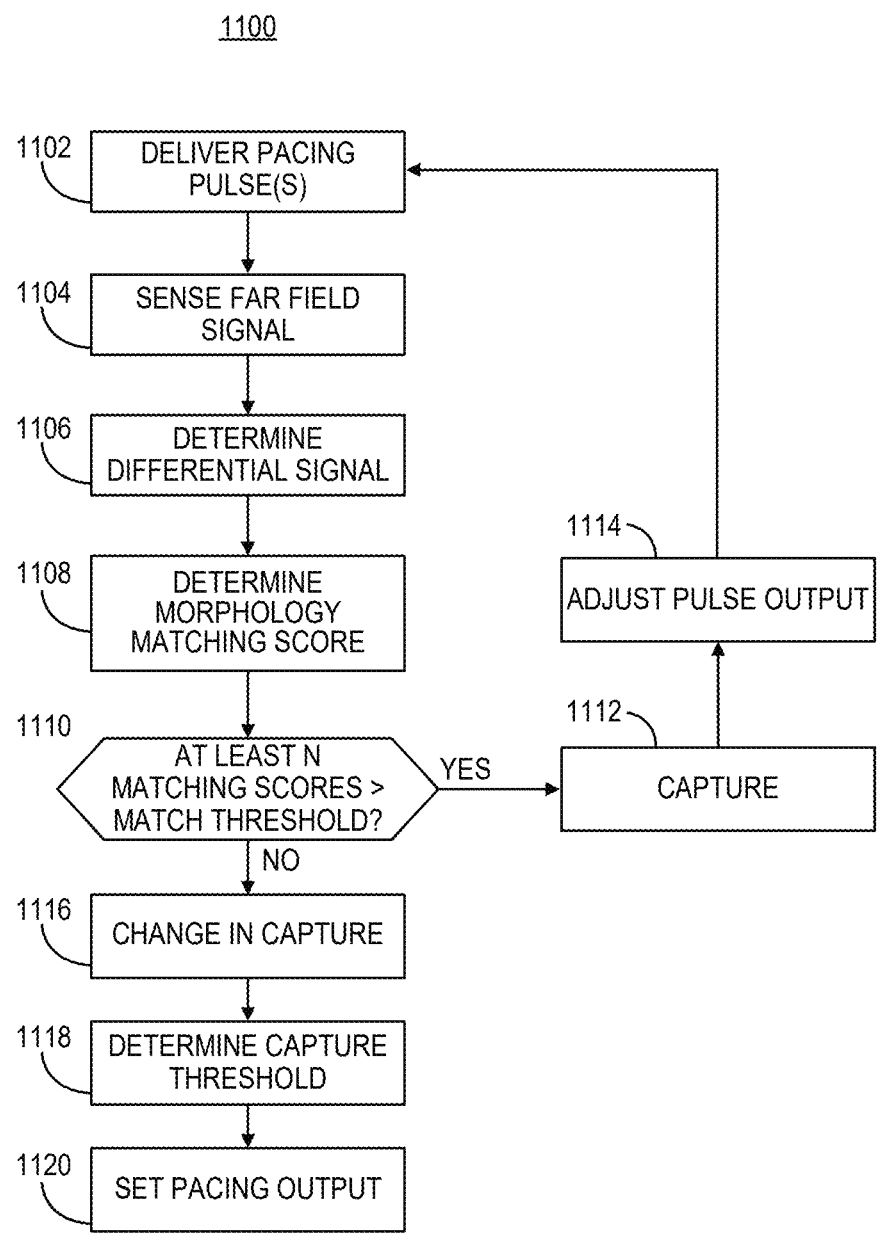
FIG. 21 is a flow chart of a method for performing a capture threshold test according to one example.

FIG. 21 is a flow chart 1100 of a method for performing a capture threshold test according to one example. The capture threshold test may be performed on periodic basis, e.g., once per hour, once per four hours, once per eight hours, once per twelve hours or once per day. The capture threshold test may be performed at a scheduled time of day, e.g., during the night while the patient is expected to be asleep. The capture threshold test may be performed in response to detecting a change in capture type during capture monitoring, e.g., as described in conjunction with FIG. 16.

At block 1102, control circuit 80 may control therapy delivery circuit 84 to deliver one or more pacing pulses according to a starting pacing pulse output. For the sake of illustration, in the capture threshold test of flow chart 1100, therapy delivery circuit 84 starts delivering pacing pulses having a relatively high pacing pulse output, e.g., at least 5.0 volts pulse amplitude with a pulse width of at least 0.25 to 1.0 ms, and progressively decreases the pacing pulse amplitude until a capture change is detected. In other examples, however, therapy delivery circuit 84 may deliver pacing pulses starting from a relatively low pacing pulse output and progressively increase the pacing pulse output until a capture change is detected. In still other examples, the pacing pulse output may be started at the most recent pacing pulse output and be increased and/or decreased until a capture change is detected. In other examples, the pacing pulse output may be varied randomly or according to a binary or other search algorithm to acquire morphology matching score data for identifying a capture threshold. Therapy delivery circuit 84 may deliver a predetermined number of pacing pulses at each pulse output setting, e.g., 3 to 8 pacing pulses or 5 pacing pulses in an example.

At block 1104, sensing circuit 86 senses a far field EGM signal, and control circuit 80 determines the differential signal from the far field EGM signal at block 1106, e.g., using the techniques described above. Control circuit 80 may buffer time segments of the differential signal, e.g., 150 to 350 ms time segments, following each pacing pulse delivered at the current pulse output setting. In some examples, a 180 to 200 ms time segment of the differential signal is buffered following each pacing pulse for use in determining a morphology matching score at block 1108 using a previously established capture detection morphology template, as described in conjunction with FIG. 15.

At block 1110, control circuit 80 determines whether the matching score is greater than a match threshold for at least a threshold number of the pacing pulses that are delivered at the current pacing pulse output. A morphology matching score greater than a match threshold for one pacing pulse may indicate capture corresponding to the capture detection morphology template. In some examples, however, a threshold number of X out of Y, e.g., at least 3 out of 5, 4 out of 5, or other threshold number or percentage of the morphology matching scores determined for the current pacing pulse output may be required to be greater than the match threshold in order to detect capture of the His-Purkinje system corresponding to the type of capture represented by the capture detection morphology template.

When at least the threshold number of morphology matching scores are greater than the match threshold ("yes" branch of block 1110), control circuit 80 detects His-Purkinje system capture corresponding to the capture detection morphology template at the current pacing pulse output settings at block 1112. In order to determine the capture threshold, control circuit 80 may adjust the pacing pulse output at block 1114 to a different pulse width or pulse amplitude so that the lowest pacing pulse output detected as capture based on the morphology matching scores can be identified. The process of blocks 1102 through 1114 may be repeated with the pacing pulse output, e.g., pulse amplitude, being decreased at block 1114 each time capture is detected at block 1112. For example, the pacing pulse amplitude may be decreased by 0.1 to 0.5 volt steps, or 0.25 volt steps in an example.

If fewer than the threshold number of morphology matching scores are greater than the match threshold at block 1110 ("no" branch), control circuit 80 detects a change in capture type at block 1116. As illustrated in FIGS. 17-19, the change in capture type may be a change from capturing the His-Purkinje system to capturing the ventricular myocardium. In other instances, the change in capture type may be a change from capturing both the His-Purkinje system and ventricular myocardium to capturing only the His-Purkinje system or only the ventricular myocardium. In still other instances, the change in capture type may be a change from capturing a first portion of the His-Purkinje system to capturing a different portion of the His-Purkinje system, e.g., capturing both the LBB and the RBB to capturing only the LBB or only the RBB. The change in capture type is a change from the type of capture corresponding to the capture detection morphology template that includes capture of at least a portion of the His-Purkinje system to a different type of capture that may or may not include capture of any portion of the His-Purkinje system.

At block 1118, control circuit 80 may identify the lowest pacing pulse output at which capture was detected at block 1112. When the pacing pulse output is progressively decreased, the most recent preceding pacing pulse output setting that resulted in capture detection at block 1112, prior to detecting the change in capture, may be identified as the capture threshold. Control circuit 80 may set the pacing pulse output at block 1120 to a safety margin (amplitude margin or pulse width margin) greater than the capture threshold, e.g., 0.25 to 1.0 volts higher than the capture threshold pulse amplitude.

In this example, the capture threshold test may be terminated when a change in capture type is detected based on the morphology matching scores determined between differential signal segments and the established capture detection morphology template. It is to be understood, however, that therapy delivery circuit 84 may continue to decrease the pacing pulse output until total loss of capture of both the His-Purkinje system and ventricular myocardium is detected, e.g., based on no evoked response detection from the near field EGM signal. In some examples, a minimum capture threshold may be determined by control circuit 80 for setting a pacing pulse output to a minimum level for achieving any type of ventricular capture, e.g., any type of His-Purkinje capture or ventricular myocardial capture. When the capture threshold determined at block 1118 is very high and could result in premature drain of the power source 98, reducing the useful life of the IMD 14 or pacemaker 100, a lower pacing pulse output may be selected to achieve capture of some type in order to provide ventricular rate support and prevent asystole, even if the resulting capture is less physiological than a desired His-Purkinje system type of capture.

Figure 22:
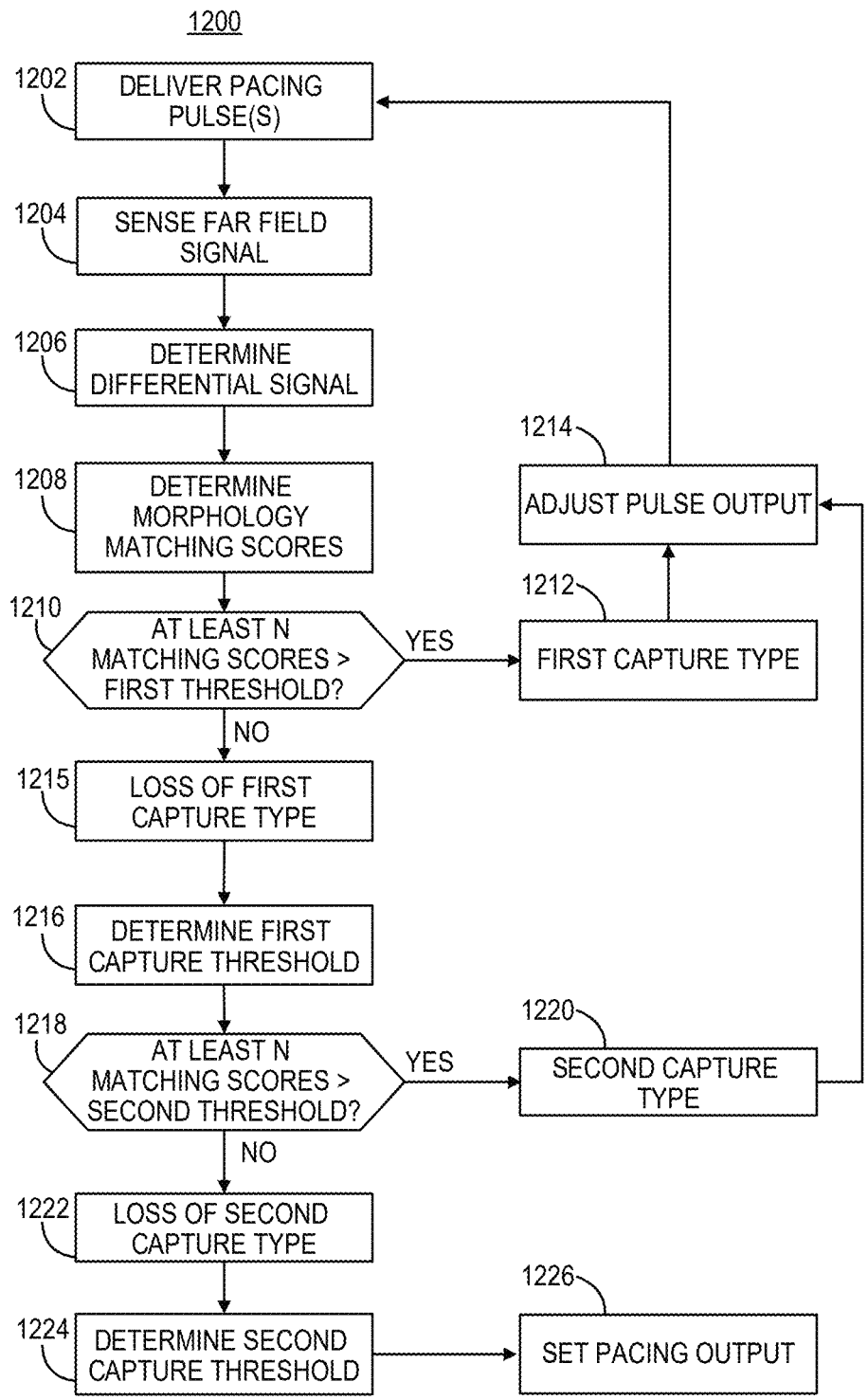
FIG. 22 is a flow chart of a method for determining the capture thresholds for more than one type of capture of the His-Purkinje system according to some examples.

FIG. 22 is a flow chart 1200 of a method for determining the capture thresholds for more than one type of capture of the His-Purkinje system according to some examples. For the sake of convenience, flow chart 1300 is described as being performed by control circuit 80 in collaboration with memory 82, sensing circuit 86 and therapy delivery circuit 84 of IMD 14 (or pacemaker 100). It is to be understood that at least some of the process of flow chart 1200 may be performed by external device processor 52 configured to receive the far field EGM signal or differential signal determined from the far field EGM signal and His-Purkinje pacing pulse timing markers from IMD 14 or pacemaker 100. In other examples, IMD 14 (or pacemaker 100) and external device processor 52 may perform some or all of the process of flow chart 1300 in a distributed manner. For example, IMD 14 may determine morphology matching scores during multiple pacing pulse outputs. External device processor 52 may receive the morphology matching scores and associated pacing pulse outputs from IMD 14 and use the received data for detecting changes in capture type and determining associated capture thresholds as described below.

At block 1202, therapy delivery circuit 84 delivers one or more pacing pulses at a selected pacing pulse output, e.g., starting from a relatively high pacing pulse amplitude. Control circuit 80 receives the far field EGM signal from sensing circuit 86 at block 1204 and determines the differential signal from the far field signal at block 1206 according to any of the examples described above. At block 1208, control circuit 80 determines morphology matching scores for at least one pacing pulse delivered at the current pacing pulse output using a previously established capture detection morphology template. The capture detection morphology template may be established using the techniques described above, e.g., in conjunction with FIG. 15.

At block 1210, control circuit 80 may compare the morphology matching score(s) to a first match threshold. The first match threshold may discriminate between a first type of capture of the His-Purkinje system corresponding to the type of capture associated with the capture detection morphology template and a second type of capture of the His-Purkinje system different than the first type of capture. When a threshold number of the morphology matching scores are greater than or equal to the first match threshold, control circuit 80 may detect the first type of capture of the His-Purkinje system corresponding to the type of capture associated with the capture detection morphology template at block 1212. Control circuit 80 may decrease the pacing pulse output at block 1214 to search for the first type of capture threshold.

The process returns to block 1202 and is repeated until less than a threshold number of morphology matching scores are greater than or equal to the first match threshold at block 1210. When this occurs, control circuit 80 may determine that the first type of capture is lost at block 1215. In response to detecting the loss of the first capture type at block 1215, control circuit 80 may determine and store a first capture threshold at block 1216 as the lowest pacing pulse output at which the first capture type was detected. The first capture threshold can be the lowest pacing pulse output at which the type of capture associated with the capture detection morphology template occurs based on the morphology matching scores.

When loss of the first capture type is detected, control circuit 80 detects a change in capture type. The change in capture type may still include capture of a portion of the His-Purkinje system, such as a change from NSHP capture to SHP capture, a change from bilateral BB capture to LBB capture, or a change from bilateral BB capture to RBB capture. Memory 82 may be configured to store at least two match thresholds for detecting a loss of the first capture type (and change to a second capture type) and for detecting a loss of the second capture type (and change to a third capture type or to total loss of capture). As such, in response to detecting loss of the first type capture, control circuit 80 may compare the morphology matching score(s) determined for the current pacing pulse output to a second match threshold at block 1218.

When at least a threshold number of the morphology matching scores are greater than or equal to the second match threshold ("yes" branch of block 1218), which is lower than the first match threshold, control circuit 80 may detect a second type of capture at block 1220. The second type of capture in this case may or may not include a portion of the His-Purkinje system. For example, when the first type of capture is NSHP capture and the SHP capture threshold is greater than the VM capture threshold, the second type of capture may correspond to VM capture when a loss of NSHP capture occurs due to loss of His-Bundle capture. In other instances, however, the ventricular myocardial capture threshold may be greater than the SHP capture threshold such that the second type of capture is SHP capture when loss of NSHP capture occurs due to loss of ventricular myocardial capture. In still other examples, the first type of capture may be bilateral BB capture that is lost when capture of one BB, either the RBB or LBB, is lost and capture of the second BB, LBB or RBB, is still occurring at the current pacing pulse output. These examples of a first type of capture of at least a portion of the His-Purkinje system that can be lost when a second type of capture, which may or may not include capture of a portion of the His-Purkinje system, occurs at a relatively lower pacing pulse output are illustrative in nature and not intended to be limiting. Other examples of a second type of capture of the His-Purkinje system and/or ventricular myocardium can occur when loss of a first type of capture of at least a portion of the His-Purkinje system occurs.

After detecting the second type of capture at block 1220, control circuit 80 may adjust the pacing pulse output at block 1214, e.g., by decreasing the pulse amplitude, and return to block 1202 to deliver pacing pulses and determine morphology matching scores from the differential signal determined from the far field EGM signal received during pacing at the adjusted pulse output. It is recognized that control circuit 80 may skip the comparison of morphology matching scores to the first threshold at block 1210 when the first capture threshold has already been determined and advance directly to block 1218 to compare the morphology matching scores to the second match threshold.

When control circuit 80 determines that less than a threshold number of the morphology match scores are greater than or equal to the second match threshold ("no" branch of block 1218), control circuit 80 determines loss of the second capture type at block 1222. The loss of the second capture type may correspond to a change from capturing a portion of the His-Purkinje system to VM capture, a change from VM capture to total loss of capture, or a change from capturing at least a portion of the His-Purkinje system to total loss of capture, as examples. In response to detecting loss of the second type of capture at block 1222, control circuit 80 may determine a second capture threshold at block 1224. The second capture threshold is the lowest pacing pulse amplitude at which the second capture type was detected (at block 1220) based on the morphology matching scores being greater than the second match threshold. Control circuit 80 may store the first capture threshold and the second capture threshold in memory 82.

In some examples, control circuit 80 may set the pacing pulse output at block 1226 based on one of the first capture threshold or the second capture threshold. In some instances, the first capture type is a desired or intended capture type. In this case, control circuit 80 may set the pacing output to be a safety margin greater than the first capture threshold. In other instances, the second capture type may be a desired or intended capture type. In this case, control circuit 80 may set the pacing output to be a safety margin greater than the second capture threshold (which may be less than the first capture threshold). The pacing output may be set based on the second capture threshold when the first capture threshold is determined to be greater than a pacing output limit that may be associated with premature drain of the power source 98. The pacing output may be set based on the second capture threshold when the improvement in the QRS signal toward a more physiological QRS signal, e.g., narrow QRS width and absence of a LBB block or RBB block type of morphology is acceptable during pacing that results in the second capture type.

Figure 23:
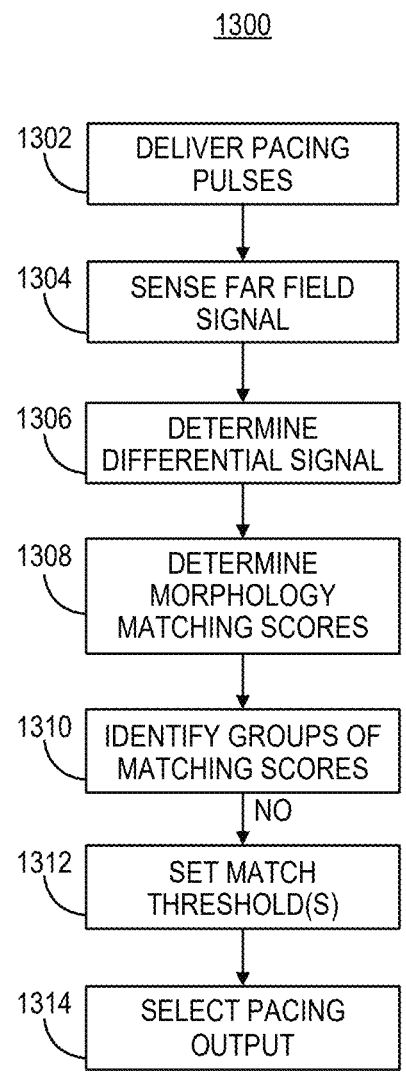
FIG. 23 is a flow chart of a method for establishing morphology match thresholds for detecting different types of capture during His-Purkinje system pacing according to some examples.

FIG. 23 is a flow chart 1300 of a method for establishing morphology match thresholds for detecting different types of capture during His-Purkinje system pacing according to some examples. For the sake of convenience, flow chart 1300 is described as being performed by control circuit 80 in collaboration with memory 82, sensing circuit 86 and therapy delivery circuit 84. It is to be understood that at least some of the process of flow chart 1300 may be performed by external device processor 52 configured to receive the far field EGM signal, or the differential signal determined from the far field EGM signal, and His-Purkinje pacing pulse timing markers from IMD 14 or pacemaker 100. In other examples, IMD 14 (or pacemaker 100) and external device processor 52 may perform at least some of the process of flow chart 1300 in a distributed manner. For example, IMD 14 may determine morphology matching scores during multiple pacing pulse outputs. External device processor 52 may receive the morphology matching scores and associated pacing pulse outputs from IMD 14 and use the received data for setting match thresholds as described below. The match thresholds may be transmitted to IMD 14 from external device 50 for use by IMD 14 during subsequent capture management functions and capture threshold searches, as generally described above, e.g., in conjunction with FIG. 16.

At block 1302, therapy delivery circuit 84 may generate pacing pulses according to multiple pacing pulse outputs. Therapy delivery circuit 84 may deliver a predetermined number of pacing pulses, e.g., 1 to 10 pacing pulses, at each pacing pulse output setting. In some examples, therapy delivery circuit 84 may decrease the pacing pulse amplitude from 5.0 volts to 1.0 volts (or less) or until an evoked response is no longer detected following the pacing pulses.

At block 1304, sensing circuit 86 senses the far field EGM signal, e.g., from pacing tip electrode 32 to IMD housing 15 or pacing ring electrode 34 to IMD housing 15 or from other available electrodes. Control circuit 80 receives the far field EGM signal during pacing pulse delivery to the His-Purkinje system and determines the differential signal at block 1306 using any of the techniques described above. Control circuit 80 determines morphology matching scores at block 1308 from time segments of the differential signal (following each pacing pulse) and a capture detection morphology template stored in memory 82. The capture detection morphology template corresponds to a type of cardiac pacing capture that includes at least a portion of the His-Purkinje system. The actual specific type of cardiac pacing capture may or may not be known by control circuit 80, e.g., SHP vs. NSHP capture, LBB vs. bilateral BB, etc. However, the capture detection morphology template may be previously established from the far field EGM signal sensed during pacing at a His-Purkinje system pacing site using a relatively high pacing pulse output expected or known to capture at least a portion of the His-Purkinje system.

The morphology matching scores may be determined at block 1308 from at least one differential signal segment determined from the far field EGM signal sensed during pacing pulse delivery at each pacing pulse output setting. In some examples, morphology matching scores are determined for each one of multiple differential signal segments obtained at each pacing pulse output setting. In this way, control circuit 80 may store a distribution of morphology matching scores in memory 82 by storing multiple morphology matching scores associated with each pacing pulse output setting.

At block 1310, control circuit 80 may identify groups of morphology matching scores from the distribution of the morphology matching scores determined at block 1308. For example, a first group of morphology matching scores may be determined that fall within a threshold difference or range of each other. A second group of morphology matching scores may be identified that fall within a threshold difference of each other and are all (or a threshold percentage are) less than the matching scores of the first group. In some examples, a third group of morphology matching scores may be identified that are all (or a threshold percentage are) less than the matching scores of the second group.

In some examples, control circuit 80 may store morphology matching scores in a histogram in memory 82 to obtain a frequency distribution of the morphology matching scores. Groups of morphology matching scores may be identified at block 1310 according to peaks in the frequency distribution of the morphology matching scores. For example, as seen in FIG. 19, a first group of morphology matching scores that are greater than 60 and a second group of morphology matching scores that are less than 40 could be identified.

At block 1312, control circuit 80 may set one or more match thresholds based on the identified groups of matching scores. A match threshold may be set between the matching scores of the first group and the matching scores of the second group. When a third group of matching scores is identified, a second match threshold may be set by control circuit 80 between the matching scores of the second group and the third group. The match thresholds may be used by control circuit 80 for detecting cardiac pacing capture types that are different than the type of capture associated with the capture detection morphology template. For instance, during capture management monitoring or a capture threshold test, control circuit 80 may detect a second type of capture different than the first type of capture in response to a threshold number of morphology matching scores being less than the first match threshold (but greater than a second match threshold if established) for a given pacing pulse output. Control circuit 80 may detect a third type of capture different than the first type of capture and the second type of capture when a threshold number of the morphology matching scores are less than the second match threshold for a given pacing pulse output.

After setting the match threshold(s), control circuit 80 may optionally set the pacing pulse output at block 1314 based on the lowest pacing pulse output associated with the first group of morphology matching scores identified at block 1308. The pacing pulse output may be set to a safety margin above the lowest pacing pulse output associated with the first group of morphology matching scores. In this way, therapy delivery circuit 84 can deliver His-Purkinje pacing pulses at an output expected to capture at least a portion of the His-Purkinje system corresponding to the first type of capture associated with the capture detection morphology template.

In other examples, a desired capture type may correspond to the second group of morphology matching scores. For instance, when the first type of capture associated with the first group of morphology matching scores corresponds to NSHP capture and the second type of capture associated with the second group of morphology matching scores corresponds to SHP capture, control circuit 80 may be configured to select the pacing pulse output based on a lowest pacing pulse output associated with the second group of morphology matching scores. Control circuit 80 may set the pacing pulse output to a safety margin greater than the lowest pacing pulse output associated with the second group of morphology matching scores. In this way, therapy delivery circuit 84 can deliver His-Purkinje pacing pulses at an output that is expected to capture at least a portion of the His-Purkinje system corresponding to the second type of capture associated with a different type of capture than the capture detection morphology template.

For example, when the ventricular myocardial capture threshold is higher than the His bundle capture threshold, the NSHP capture threshold is greater than the SHP capture threshold. The capture detection morphology template established at a relatively high pacing pulse output may correspond to NSHP capture in this example. A pacing pulse output that is expected to achieve SHP capture may be selected at block 1314 based on the pacing pulse outputs associated with the second group of morphology matching scores. Selecting a pacing output that is less than the NSHP capture threshold can promote physiological SHP pacing while conserving power source 98.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of circuits or components associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device system, comprising:
a memory configured to store at least a first capture detection morphology template corresponding to a first type of cardiac pacing capture that includes capture of a first portion of a His-Purkinje system; and
a processing circuit configured to:
receive a cardiac electrical signal;
determine a first plurality of morphology matching scores from the cardiac signal and the first capture detection morphology template; and
establish a first match threshold based on at least the first plurality of morphology matching scores by:
determining the first plurality of morphology matching scores from the cardiac signal associated with pacing pulse delivery at each of a plurality of different pacing pulse outputs;
determining a frequency distribution of the first plurality of morphology matching scores; and
establishing the first match threshold based on the frequency distribution of the first plurality of morphology matching scores;
determine a first morphology matching score from the cardiac electrical signal and the first capture detection morphology template;
determine that the first morphology matching score is less than the first match threshold;
detect a second type of cardiac pacing capture in response to the first morphology matching score being less than the first match threshold, the second type of cardiac pacing capture being different than the first type of cardiac pacing capture; and
select a pacing pulse output in response to detecting the second type of cardiac pacing capture; and
a therapy delivery circuit configured to generate pacing pulses according to the pacing pulse output selected by the processing circuit.

2. The medical device system of claim 1, wherein the processing circuit is further configured to:
determine a differential signal from the cardiac electrical signal; and
determine the first morphology matching score from the cardiac electrical signal and the first capture detection morphology template by determining a morphology matching score from the differential signal and the first capture detection morphology template.

3. The medical device system of claim 2, wherein the processing circuit is further configured to:
determine a low pass filtered signal from the cardiac electrical signal; and
determine the differential signal from the low pass filtered signal.

4. The medical device system of claim 2, wherein the processing circuit is further configured to determine the differential signal by determining each sample point of the differential signal using at least three points of the cardiac electrical signal.

5. The medical device system of claim 1, wherein the processing circuit is further configured to:
establish the first capture detection morphology template from the cardiac electrical signal sensed following pacing pulse delivery to at least a portion of the His-Purkinje system at a first pacing pulse output.

6. The medical device system of claim 5, wherein the processing circuit is further configured to:
receive the cardiac electrical signal sensed following pacing pulse delivery to at least the portion of the His-Purkinje system at a second pacing pulse output; and
establish a second capture detection morphology template from the cardiac electrical signal sensed following pacing pulse delivery at the second pacing pulse output, the second capture detection morphology template corresponding to the second type of cardiac pacing capture.

7. The medical device system of claim 6, wherein the processing circuit is further configured to:
determine a second morphology matching score from the cardiac electrical signal and the second capture detection morphology template;
determine that the second morphology matching score is less than a second match threshold; and
detect a third type of cardiac pacing capture different than the first type of cardiac pacing capture and the second type of cardiac pacing capture in response to the second morphology matching score being less than the second match threshold.

8. The medical device system of claim 1, wherein the processing circuit is further configured to:
determine the first morphology matching score from the first capture detection morphology template and the cardiac electrical signal sensed following pacing pulse delivery at a first pacing pulse output;
determine a second morphology matching score from the first capture detection morphology template and the cardiac electrical signal sensed following pacing pulse delivery at a second pacing pulse output different than the first pacing pulse output;
determine that the second morphology matching score is less than a second match threshold different than the first match threshold; and
detect a third type of cardiac pacing capture different than the first type of cardiac pacing capture in response to the second morphology matching score being less than the first match threshold.

9. The medical device system of claim 1, wherein the processing circuit is further configured to perform a capture threshold test in response to detecting the second type of cardiac pacing capture.

10. The medical device system of claim 1, further comprising:
an implantable medical device comprising:
a sensing circuit configured to sense the cardiac electrical signal; and
the therapy delivery circuit configured to generate pacing pulses according to the selected pacing pulse output.

11. The medical device system of claim 1, further comprising a telemetry circuit in communication with the processing circuit, wherein:
the processing circuit is further configured to:
determine a differential signal from the cardiac electrical signal; and
determine the first morphology matching score from the cardiac electrical signal and the first capture detection morphology template by determining a morphology matching score from the differential signal and the first capture detection morphology template; and
the telemetry circuit is configured to transmit at least one of the differential signal or the first morphology matching score.

12. The medical device system of claim 1, wherein the processing circuit is further configured to:
  detect the second type of cardiac pacing capture by detecting cardiac pacing capture that includes capture of a second portion of the His-Purkinje system different than the first portion of the His-Purkinje system.

13. The medical device system of claim 1, wherein the processing circuit is further configured to:
  detect the second type of cardiac pacing capture by detecting cardiac pacing capture that includes ventricular myocardial capture.

14. A non-transitory, computer-readable storage medium comprising a set of instructions which, when executed by a processing circuit of a medical device cause the medical device to:
  store a capture detection morphology template corresponding to a first type of cardiac pacing capture that includes capture of a first portion of a His-Purkinje system;
  receive a cardiac electrical signal;
  determine a plurality of morphology matching scores from the cardiac signal and the capture detection morphology template;
  establish a match threshold based on at least the plurality of morphology matching scores by:
    determining the first plurality of morphology matching scores from the cardiac signal associated with pacing pulse delivery at each of a plurality of different pacing pulse outputs;
    determining a frequency distribution of the first plurality of morphology matching scores; and
    establishing the first match threshold based on the frequency distribution of the first plurality of morphology matching scores;
  determine a morphology matching score from the cardiac electrical signal and the capture detection morphology template;
  determine that the morphology matching score is less than the match threshold;
  detect a second type of cardiac pacing capture in response to the morphology matching score being less than the match threshold, the second type of cardiac pacing capture being different than the first type of cardiac pacing capture;
  select a pacing pulse output in response to detecting the second type of cardiac pacing capture; and
  generate pacing pulses according to the selected pacing pulse output.

15. The non-transitory, computer-readable storage medium of claim 14, further comprising instructions that cause the medical device to:
  determine a differential signal from the cardiac electrical signal; and
  determine the morphology matching score from the cardiac electrical signal and the capture detection morphology template by determining a morphology matching score from the differential signal and the capture detection morphology template.

16. The non-transitory, computer-readable storage medium of claim 15, further comprising instructions that cause the medical device to perform a capture threshold test in response to detecting the second type of cardiac pacing capture.

17. A medical device system, comprising:
  a memory configured to store a capture detection morphology template corresponding to a first type of cardiac pacing capture that includes capture of a first portion of a His-Purkinje system;
  a processing circuit configured to:
    receive a cardiac electrical signal;
    determine a differential signal from the cardiac electrical signal;
    determine a plurality of morphology matching scores from the cardiac signal and the capture detection morphology template;
    establish a match threshold based on at least the plurality of morphology matching scores by:
      determining the first plurality of morphology matching scores from the cardiac signal associated with pacing pulse delivery at each of a plurality of different pacing pulse outputs;
      determining a frequency distribution of the first plurality of morphology matching scores; and
      establishing the first match threshold based on the frequency distribution of the first plurality of morphology matching scores;
    determine a morphology matching score from the differential signal and the capture detection morphology template;
    determine that the morphology matching score is less than the match threshold;
    detect a second type of cardiac pacing capture in response to the morphology matching score being less than the match threshold, the second type of cardiac pacing capture being different than the first type of cardiac pacing capture; and
    select a pacing pulse output in response to detecting the second type of cardiac pacing capture;
  a display unit configured to receive the morphology matching score from the processing circuit and generate a display of a graphical user interface including at least the morphology matching score; and
  a therapy delivery circuit configured to generate pacing pulses according to the selected pacing pulse output.

* * * * *